US006896881B1

(12) United States Patent
Russell et al.

(10) Patent No.: US 6,896,881 B1
(45) Date of Patent: *May 24, 2005

(54) THERAPEUTIC METHODS AND COMPOSITIONS USING VIRUSES OF THE RECOMBINANT PARAMYXOVIRIDAE FAMILY

(75) Inventors: Stephen James Russell, Rochester, MN (US); Kah-Whye Peng, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 419 days.

This patent is subject to a terminal disclaimer.

(21) Appl. No.: 09/667,947

(22) Filed: Sep. 22, 2000

Related U.S. Application Data

(60) Provisional application No. 60/155,873, filed on Sep. 24, 1999.

(51) Int. Cl.[7] .................. A01N 63/00; A61K 39/00; A61K 39/165; C12Q 1/68; C12N 15/00

(52) U.S. Cl. ................ 424/93.2; 424/93.21; 424/192.1; 424/212.1; 435/6; 435/320.1

(58) Field of Search ................ 424/93.2, 93.21, 424/192.1, 212.1; 435/6, 320.1, 4, 7.1, 810

(56) References Cited

U.S. PATENT DOCUMENTS

| | | | |
|---|---|---|---|
| 4,108,983 A | 8/1978 | Wallack | 424/89 |
| 4,500,512 A | 2/1985 | Barme | 424/89 |
| 4,985,244 A | 1/1991 | Makino et al. | 424/89 |
| 5,001,692 A | 3/1991 | Farla et al. | 369/48 |
| 5,137,727 A | 8/1992 | Eckenhoff | 424/422 |
| 5,175,099 A * | 12/1992 | Wills | 435/69.7 |
| 5,262,359 A | 11/1993 | Hierholzer | 435/235.1 |
| 5,304,367 A | 4/1994 | Biegon | 424/1.11 |
| 5,698,530 A * | 12/1997 | Schlom et al. | 514/44 |
| 5,713,858 A | 2/1998 | Heruth et al. | 604/93 |
| 5,714,347 A | 2/1998 | Haas et al. | 435/69.1 |
| 5,731,306 A | 3/1998 | Flynn et al. | 514/44 |
| 5,738,985 A | 4/1998 | Miles et al. | 435/5 |
| 5,773,222 A | 6/1998 | Scott | 435/7.1 |
| 5,980,508 A | 11/1999 | Cardamone et al. | 604/890.1 |
| 5,981,481 A | 11/1999 | Fearon et al. | 514/12 |
| 6,012,034 A | 1/2000 | Hamparian et al. | 705/2 |
| 6,022,683 A | 2/2000 | Poirier | 435/4 |
| 6,026,316 A | 2/2000 | Kucharczyk et al. | 600/420 |
| 6,054,273 A | 4/2000 | Housman | 435/6 |
| 6,077,519 A | 6/2000 | Storkus et al. | 424/277.1 |
| 6,083,751 A | 7/2000 | Feldhaus et al. | 435/372.3 |
| 6,095,976 A | 8/2000 | Nachtomy et al. | 600/443 |
| 6,110,461 A | 8/2000 | Lee et al. | 424/93.6 |
| 6,632,800 B1 * | 10/2003 | Russell et al. | 514/44 |

FOREIGN PATENT DOCUMENTS

| | | |
|---|---|---|
| EP | 0 700 995 A2 | 3/1996 |
| WO | WO 97/12032 | 4/1997 |
| WO | WO 00/76450 | 12/2000 |

OTHER PUBLICATIONS

Singh et al., Jan. 1999, Journal of General Virology, vol. 80, pp. 101–106.*

Bailly et al., "A Recombinant Human Parainfluenza Virus Type 3 (PIV3) in Which the Nucleocapsid N Protein Has Been Replaced by That of Bovine PIV3 Is Attenuated in Primates," *J. Virol.*, 2000, 74:3188–3195.

Schirrmacher et al., "Human tumor cell modification by virus infection: an efficient and safe way to produce cancer vaccine with pleiotropic immune stimulatory properties when using Newcastle disease virus," *Gene Therapy*, 1999, 6:63–73.

Tao et al., "Recovery of a Fully Viable Chimeric Human Parainfluenza Virus (PIV) Type 3 in Which the Hemagglutinin–Neuraminidase and Fusion Glycoproteins Have Been Replaced by Those of PIV Type 1," *J. Virol.*, 1998, 72:2955–2961.

Cathomen et al., "Measles Viruses with Altered Envelope Protein Cytoplasmic Tails Gain Cell Fusion Competence", (Feb. 1998), *Journal of Virology*, vol. 72, No. 2, p. 1224–1234.

Kao et al., "C–Peptide Immunochemiluminometric Assay Developed From Two Seemingly Identical Polyclonal Antisera", (1992) *Annals of Clinical and Laboratory Science*, vol. 22, No. 5, p. 307 350.

Radecke, et al., "Rescue of Measles viruses from cloned DNA", (1995), *The Embo Journal* vol. 14 No. 23, pp. 5773–5784.

Cathomen et al., "A Matrix–less Measles Virus is Infectious and Elicits Extensive Cell Fusion: Consequences for Propagation in the Brain", (1998), *The Embo Journal* vol. 17 No. 14 pp. 3899–3908.

(Continued)

Primary Examiner—Shin-Lin Chen
(74) Attorney, Agent, or Firm—Fish & Richardson P.C., P.A.

(57) ABSTRACT

The invention relates to compositions and methods for treating a patient having a tumor in order to reduce tumor size, comprising administering to the patient a replication-competent Paramyxoviridae virus comprising two or more of a) a nucleic acid sequence encoding a heterologous polypeptide, wherein upon administration the heterologous polypeptide is detectable in a biological fluid of the patient, and detection of the heterologous polypeptide is indicative of Paramyxoviridae virus growth in the patient and reduction in tumor size; b) a recombinant F protein, H protein, or M protein of Paramyxoviridae virus that increases fusogenicity of virus with cells; c) a nucleic acid sequence encoding a cytokine; and d) a Paramyxoviridae virus that is specific for cells of the tumor.

21 Claims, 29 Drawing Sheets

OTHER PUBLICATIONS

Figure 1:
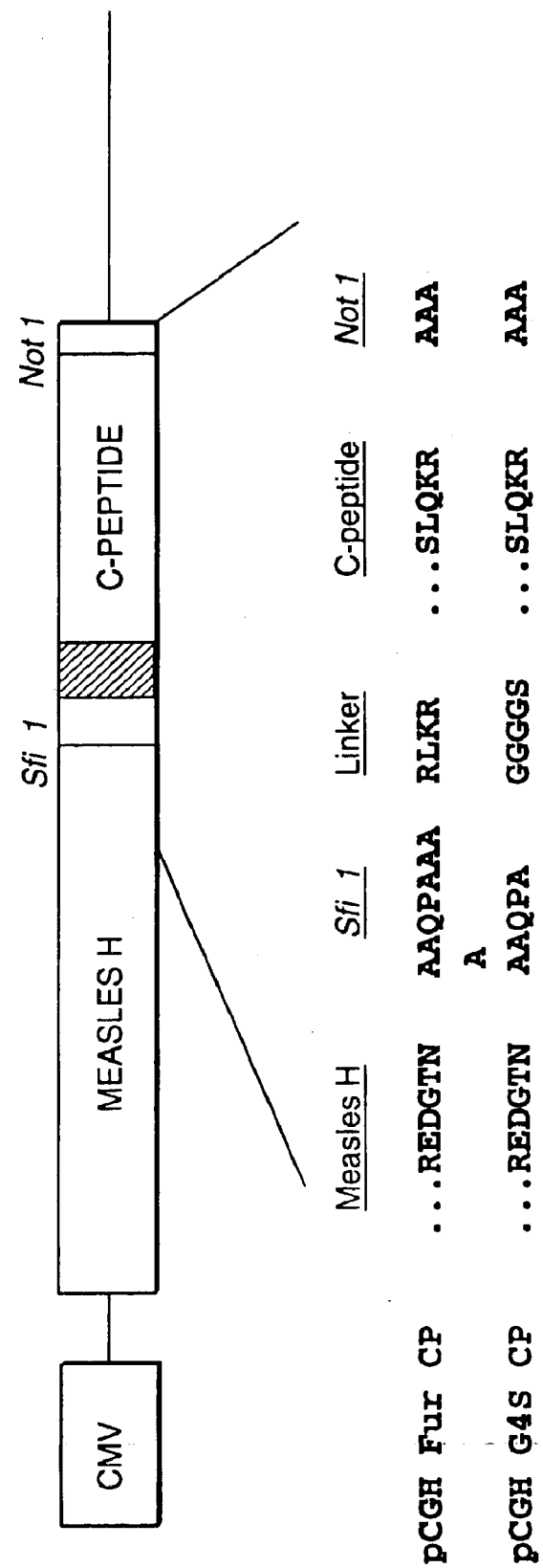

Asada, "Treatment of Human Cancer with Mumps Virus", (1974), *Cancer* 34:1907–1928.

Bennett et al., *Biotechniques*, 1998, 24(3):478–482.

Kirn et al., *Molecular Medicine Today*, 1996, 2(12):519–527.

Lorence et al., *Journal of the National Cancer Institute*, 1994, 86(16):1228–1233.

Sinkovics et al., *Medical Hypotheses*, 1995, 44:359–368.

GenBank Accession No. U60282.

Albonico et al., "Febrile infectious childhood diseases in the history of cancer patients and matched controls," *Medical Hypotheses*, 1998, 51:315–320.

Alemany et al., "Replicative adenoviruses for cancer therapy," *Nature Biotechnol.*, 2000, 18:723–727.

Andreansky et al., "The application of genetically engineered herpes simplex viruses to the treatment of experimental brain tumors," *Proc. Natl. Acad. Sci. USA*, 1996, 93:11313–11318.

Arbit et al., "Quantitative studies of monoclonal antibody targeting to disialoganglioside $G_{D2}$ in human brain tumors," *Eur. J. Nucl. Med.*, 1995, 22:419–426.

Bae et al., "Genomic Differences between the Diabetogenic and Nondiabetogenic Variants of Encephalomyocarditis Virus," *Virology*, 1989, 170:282–287.

Bateman et al., "Fusogenic Membrane Glycoproteins—A Novel Class of Cytotoxic Genes with Immunostimulatory Properties," *Gene Therapy*, 1999, 6(Suppl. 1):S6, Abstract #24.

Bateman et al., "Fusogenic Membranes Glycoproteins As a Novel Class of Genes for the Local and Immune–mediated Control of Tumor Growth," *Cancer Res.*, 2000, 60:1492–1497.

Berg et al., "Physiological functions of endosomal proteolysis," *Biochem. J.*, 1995, 307:313–326.

Bluming and Ziegler, "Regression of Burkitt's Lymphoma in Association with Measles Infection," *Lancet*, 1971, pp. 105–106.

Bolt and Pedersent, "The Role of Subtilisin–like Proprotein Convertases for Cleavage of the Measles Virus Fusion Glycoprotein in Different Cell Types," *Virology*, 1998, 252:387–398.

Chambers et al., "Comparison of genetically engineered herpes simplex viruses for the treatment of brain tumors in a scid mouse model of human malignant glioma," *Proc. Natl. Acad. Sci. USA*, 1995, 92:1411–1415.

Ch'ien et al., "Fatal Subacute Immunosuppressive Measles Encephalitis (SIME) in Children with Acute Lymphcytic Leukemia—Clinical, Electroencephalographic, and Computerized Tomographic Scan Features," *Clin. Electroencephalogr.*, 1983, 14(4):214–220.

Cohen et al., "Complete nucleotide sequence of an attenuated hepatitis A virus: Comparison with wild–type virus," *Proc. Natl. Acad. Sci. USA*, 1987, 84:2497–2501.

Crawford et al., "Thyroid volume measurement in thyrotoxic patients: comparison between ultrasonography and iodine–124 positron emission tomography," *Eur. J. Nucl. Med.*, 1997, 24:1470–1478.

Dai et al., "Cloning and characterization of the thyroid iodide transporter," *Nature*, 1996, 379:458–460.

de Felipe et al., "Use of the 2A sequence from foot–and–mouth disease virus in the generation of retroviral vectors for gene therapy," *Gene Ther.*, 1999, 6:198–208.

Delassus et al., "Genetic Organization of Gibbon Ape Leukemia Virus," *Virology*, 1989, 173:205–213.

De Swart et al., "Measles in a Dutch hospital introduced by an immuno–compromised infant from Indonesia infected with a new virus genotype," *Lancet*, 2000, 355:201–202.

Duechler et al., "Evolutionary relationships within the human rhinovirus genus: Comparison of serotypes 89, 2, and 14," *Proc. Natl. Acad. Sci. USA*, 1987, 84:2605–2609.

Duprex et al., "Observation of Measles Virus Cell–to–Cell Spread in Astrocytoma Cells by Using a Green Fluorescent Protein–Expressing Recombinant Virus," *J. Virol.*, 1999, 73(11):9568–9575.

Earle et al., "The Complete Nucleotide Sequence of a Bovine Enterovirus," *J. Gen. Virol.*, 1988, 69:253–263.

Eiselein et al., "Treatment of Transplanted Murine Tumors with an Oncolytic Virus and Cyclophosphamide," *Cancer Res.*, 1978, 38:3817–3822.

Evermann and Burnstein, "Immune Enhancement of the Tumorigenicity of Hamster Brain Tumor Cells Persistently Infected with Measles Virus," *Int. J. Cancer*, 1975, 16:861–869.

Flower et al., "Thyroid imaging using position emission tomography—a comparison with ultrasound imaging and conventional scintigraphy in thyrotoxicosis," *Br. J. Radiol.*, 1990, 63:325–330.

Flower et al., "Dose–response study on thyrotoxic patients undergoing positron emission tomography and radioiodine therapy," *Eur. J. Nucl. Med.*, 1994, 21:531–536.

Galanis et al., "Use of Fusogenic Membrane Glycorproteins as Novel Therapeutic Transgenes in Gliomas," *Gene Therapy*, 1999, 6(S1):S7, Abstract #28.

Gambhir et al., "Assay for Noninvasive Imaging of Reporter Gene Expression," *Nucl. Med. Biol.*, 1999, 26:481–490.

Greentree, "Hodkin's Disease: Therapeutic Role of Measles Vaccine," *Am. J . Med.*, 1983, 75:928.

Gromeier et al., "Intergeneric poliovirus recombinants for the treatment of malignant glioma," *Proc. Natl. Acad. Sci. USA*, 2000, 97(12):6803–6808.

Grote et al., "Live attenuated measles virus induces regression of human lymphoma xenografts in immunodeficient mice," *Blood*, 2001, 97(12):3746–3754.

Gura, "Systems for Identifying New Drugs Are Often Faulty," *Science*, 1997, 278:1041–1042.

Hook, *Proteolytic and Cellular Mechanisms in Prohormone and Proprotein Processing*, 1998, R.G. Landes Company, Austin, Texas (Table of Contents only).

Hooper et al., "Membrane protein secretases," *Biochem. J.*, 1997, 321:265–279.

Hughes et al., "The Complete Nucleotide Sequence of Coxsackievirus A21," *J. Gen. Virol.*, 1989, 70:2943–2952.

Iizuka et al., "Complete Nucleotide Sequence of the Genome of Coxsackievirus B1," *Virology*, 1987, 156:64–73.

Inchauspe et al. "Genomic structure of the human prototype strain H of hepatitis C virus: Comparison with American and Japanese isolates," *Biochem.*, 1991, 88:10292–10296.

Jackson, "Initiation without an end," *Nature*, 1991, 353:14–15.

Jenkins et al., "The Complete Nucleotide Sequence of Coxsackievirus B4 and Its Comparison to Other Members of the Picornaviridae," *J. Gen. Virol.*, 1987, 68:1835–1848.

Kato et al., "Molecular cloning of the human hepatitis C virus genome from Japanese patients with non–A, non–B hepatitis," *Proc. Natl. Acad. Sci. USA*, 1990, 87:9524–9528.

Kenney and Pagano, "Viruses as Oncolytic Agents: A New Age for "Therapeutic" Viruses," *J. Natl. Cancer Inst.*, 1994, 86(16):1185–1186.

Kirn and McCormick, "Replicating viruses as selective cancer therapeutics," *Mol. Med. Today*, 1996, 2(12):519–527.

Kirn, "Replication–selective microbiological agents: fighting cancer with targeted germ warfare," *J. Clin. Invest.*, 2000, 105(7):837–839.

Kirn, "Replication–selective oncolytic adenoviruses: virotherapy aimed at genetic targets in cancer," *Oncogene*, 2000, 19:6660–6669.

Kuzumaki and Kobayashi, "Reduced Transplantability of Syngenic Mouse Tumors Superinfected with Membrane and Viruses in Nu/Nu Mice," *Transplantation*, 1976, 22(6):545–550.

Linardakis et al., "Regulated Expression of Fusogenic Membrane Glycoproteins," *Gene Therapy*, 1999, 6(Suppl. 1):S4, Abstract #13.

Lorence et al., "Newcastle Disease Virus as an Antineoplastic Agent: Induction of Tumor Necrosis Factor–α and Augmentation of Its Cytotoxicity," *J. Natl. Cancer Inst.*, 1988, 80(16):1305–1312.

Macejak and Sarnow, "Internal Initiation of translation mediated by the 5' leader of a cellular mRNA," *Nature*, 1991, 353:90–94.

Mazzaferri, "Radioiodine and Other Treatments and Outcomes," *The Thyroid—a Fundamental and Clinical Text*, Braverman and Utiger (eds.), Seventh Edition, 1996, Lippincott—Raven Publishers, Philadelphia, pp. 922–945.

Mettler et al., "Virus Inoculation in Mice Bearing Ehrlich Ascitic Tumors: Antigen Production and Tumor Regression," *Infection and Immunity*, 1982, 37:23–27.

Mitus et al., "Attenuated Measles Vaccine in Children with Acute Leukemia," *Am. J. Dis. Childred*, 1962, 103:413–418.

Mota, "Infantile Hodgkin's Disease: Remission after Measles," *Br. Med. J.*, 1973, 2:421.

Murakami and Etlinger, "Degradation of Proteins with Blocked Amino Groups by Cytoplasmic Proteases," *Biochem. Biophys. Res. Comm.*, 1987, 146(3):1249–1255.

Neagoe and Stolan, "Methods of Active Immunotherapy and Viral Oncolysis in some Forms of Cancer," *Rev. Roum. Med.—Med. Int.*, 1986, 24(2):125–142.

Nemunaitis, "Oncolytic viruses," *Investigational New Drugs*, 1999, 17:173–386.

Ohara et al., "Molecular Cloning and Sequence Determintion of DA Strain of Theiler's Murine Encephalomyelitis Viruses," *Virology*, 1988, 164:245–255.

Okamoto et al., "Full–Length Sequence of a Hepatitis C Virus Genome Having Poor Homology to Reported Isolates: Comparative Study of Four Distinct Genotypes," *Virology*, 1992, 188:331–341.

Okuno et al., "Studies on the Use of Mumps Virus for Treatment of Human Cancer," *Biken J.*, 1978, 21:37–49.

Ott et al., "Measurement of radiation dose to the thyroid using positron emission tomography," *Br. J. Radiol.*, 1987, 60:245–251.

Paillard, "Bystander Effects in Enzyme/Prodrug Gene Therapy," *Human Gene Ther.*, 1997, 8:1733–1736.

Palmenberg et al., "The nucleotide and deduced amino acid sequences of the encephalomyocarditis viral polyprotein coding region," *Nucl. Acids Res.*, 1984, 12(6):2969–2985.

Parker et al., "Cancer Statistics," *CA Cancer J. Clin.*, 1997, 47:5–27.

Pasquinucci, "Possible Effect of Measles on Leukemia," *Lancet*, 1971, 7690:136.

Paul et al., "The entire nucleotide sequence of the genome of human hepatitis A virus (isolate MBB)," *Virus Res.*, 1987, 8:153–171.

Pentlow et al., "Quantitative imaging of I–124 using positron emission tomography with applications to radioimmunodiagnosis and radioimmunotherapy," *Med. Phys.*, 1991, 18(3):357–366.

Pentlow et al., "Quantitative Imaging of Iodine–124 with PET," *J. Nucl. Med.*, 1996, 37:1557–1562.

Peavear et al., "Analysis of the Complete Nucleotide Sequence of the Picornavirus Theiler's Murine Encephalomyelitis Virus Indicates That It Is Closely Related to Cardioviruses," *J. Virol.*, 1987, 61(5):1507–1516.

Racaniello and Baltimore, "Molecular cloning of poliovirus cDNA and determination of the complete nucleotide sequence of the viral genome," *Proc. Natl. Acad. Sci. USA*, 1981, 78(8):4887–4891.

Reichard et al., "Newcastle Disease Virus Selectively Kills Human Tumor Cells," *J. Surg. Res.*, 1992, 52:448–453.

Robbins, "Stimulation of Measles Virus Replication by Cyclic Guanosine Monophosphate," *Intervirology*, 1991, 32:204–208.

Robbins and Rapp, "Inhibition of Measles Virus Replication by Cyclic AMP," *Virology*, 1980, 106:317–326.

Rubin et al., "High–Resolution Positron Emission Tomography of Human Ovarian Cancer in Nude Rats Using $^{124}$I–Labeled Monoclonal Antibodies," *Gyn. Oncol.*, 1993, 48:61–67.

Russell et al., "Use of Fusogenic Membrane Glycroproteins as Novel Therapeutic Transgenes in Gliomas," *Proc. Am. Assoc. Cancer Res.*, 2000, 41:259, Abstract #1648.

Ryan et al., "The complete nucleotide sequence of enterovirus type 70: relationships with other members of the Picornaviridae," *J. Gen. Virol.*, 1990, 71:2291–2299.

Sato et al., "Attenuated mumps virus therapy of carcinoma of the maxillary sinus," *Int. J. Oral Surg.*, 1979, 8:205–211.

Schattner, "Therapeutic Role of Measles Vaccine in Hodgkin's Disease," *Lancet*, 1984, 8367:171.

Schattner et al., "Persistent Viral Infection Affects Tumorigenicity of a Neuroblastoma Cell Line," *Cell, Immunol.*, 1985, 90:103–114.

Schirrmacher et al., "Immunization With Virus–Modified Tumor Cells," *Sem. Oncol.*, 1998, 25(6):677–696.

Schumacher et al., "Comparative analysis of IRES efficiency of dicistronic expression vectors in primary cells and permanent cell lines," *Anim. Cell Tech.*, 1999, (Abstract only).

Segni and Curro, "Tolerability of the trivalent vaccine "Triviraten Berna" in atopical children and those with a history of febrile convulsions," *Giornale di Malatti Infettive e Parassitaric*, 1992, 44(11):839–846 (Summary in English).

Shoham et al., "Augmentation of Tumor Cell Immunogenicity by Viruses—An Approach to Specific Immunotherapy of Cancer" *Nat. Immun. Cell Growth Regul.*, 1990, 9:165–172.

Sinkovics, "Oncogenes—Antioncogenes and Virus Therapy of Cancer," *Anticancer Res.*, 1989, 9:1281–1290.

Sinkovics, "Viral Oncolysates as Human Tumor Vaccines," *Intern. Rev. Immunol.*, 1991, 7:259–287.

Sinkovics and Horvath, "Newcastle disease virus (NDV): brief history of its oncolytic strains," *J. Clin. Virol.*, 2000, 16:1–15.

Skern et al., "Human rhinovirus 2: complete nucleotide sequence and proteolytic processing signals in the capsid protein region," *Nucl. Acids Res.*, 1985, 13(6):2111–2126.

Smanik et al., "Cloning of the Human Sodium Iodide Symporter," *Biochem. Biophys. Res. Comm.*, 1996, 226:339–345.

Smanik et al., "Expression, Exon–Intron Organization, and Chromosome Mapping of the Human Sodium Iodide Symporter," *Endocrinology*, 1997, 138(8):3555–3558.

Smith et al., "Studies on the Use of Viruses in the Treatment of Carcinoma of the Cervix," *Cancer*, 1956, 9(6):1211–1218.

Smyth and Trapani, "Granzymes: exogenous proteinases that induce target cell apoptosis," *Immunol. Today*, 1995, 16(4):202–206.

Sonenberg and Meerovitch, "Translation of Poliovirus mRNA," *Enzyme*, 1990, 44:278–291.

Spitzweg et al., "Prostate–specific Antigen (PSA) Promoter–driven Androgen–inducible Expression of Sodium Iodide Symporter in Prostate Cancer Cell Lines," *Cancer Res.*, 1999, 59:2136–2141.

Spitzweg et al., "Analysis of Human Sodium Iodide Symporter Immunoreactivity in Human Exocrine Glands," *J. Clin. Endocrinol. Metab.*, 1999, 84:4178–4184.

Spitzweg et al., "Treatment of Prostate Cancer by Radioiodine Therapy after Tissue–specific Expression of the Sodium Iodide Symporter," *Cancer Res.*, 2000, 60:6526–6530.

Stanway et al., "Comparison of the complete nucleotide sequences of the genomes of the neurovirulent poliovirus P3/Leon/37 and its attenuated Sabin vaccine derivative P3/Leon 12a$_1$b," *Proc. Natl. Acad. Sci. USA*, 1984, 81:1539–1543.

Talanian et al., "Substrate Specificities of Caspase Family Proteases," *J. Biol. Chem.*, 1997, 272(15):9677–9682.

Taqi et al., "Regression of Hodgkin's Disease After Measles," *Lancet*, 1981, 8223:1112.

Thornberry et al., "A Combinatorial Approach Defines Specificies of Members of the Caspase Family and Granzyme B," *J. Biol. Chem.*, 1997, 272(29):17907–17911.

Tjuvajev et al., "Imaging Herpes Virus Thymidine Kinase Gene Transfer and Expression by Positron Emission Tomography," *Cancer Res.*, 1998, 58:4333–4341.

Torigoe et al., "Application of Live Attenuated Measles and Mumps Vaccines in Children with Acute Leukemia," *Biken J.*, 1981, 24:147–151.

Usonis et al., "Reactogenecity and immunogenicity of a new live attenuated combined measles, mumps and rubella vaccine in healthy children," *Pediatr. Infect. Dis. J.*, 1999, 18:42–48.

Von Hoegen et al., "Modification of tumor cells by a low dose of Newcastle Disease Virus," *Eur. J. Immunol.*, 1988, 18:1159–1166.

Weibel et al., "Combined live measles–mumps virus vaccine," *Archives of Disease in Childhood*, 1973, 48:532–536.

Werb, "ECM and Cell Surface Proteolysis: Regulating Cellular Ecology," *Cell*, 1997, 91(4):439–442.

Wolfsberg et al., "ADAM, a Novel Family of Membrane Proteins Containing A Disintegrin And Metalloprotease Domain: Multipotential Functions in Cell–Cell and Cell–Matrix Interactions," *J. Cell. Biol.*, 1995, 131(2):275–278.

World Health Organization Technical Report Series, "WHO Expert Committee on Biological Standardization," Forty–third Report, 1994, No. 840, pp. 102–120.

Wyde et al., "Infection of leucocytes by measles vaccine viruses Edmonston–Zagreb and Enders–Moraten has different consequences: potential mechanism for increased vaccine efficacy or aberrant activity in field trials," *Vaccine*, 1994, 12(8):715–722.

Zwitter, "Hodgkin's Disease: Therapeutic Role of Measles Vaccine," *Am. J. Med.*, 1984, 77:A49, A52, A64.

Zygiert, "Hodgin's Disease: Remissions after Measles," *Lancet*, 1971, 7699:593.

\* cited by examiner

Map of p(+)MPIrGFPV

Map of p(+)MIrGFPNV

α-CD38 MV 5.5 x 10$^6$ syncytial forming units/ml

α-CD52 MV

< 10 syncytial forming units/ml

Unmodified H ↓

MV – Edm

α-CD38 MV

α-CD52 MV

↑ Chimeric H

FIG. 7

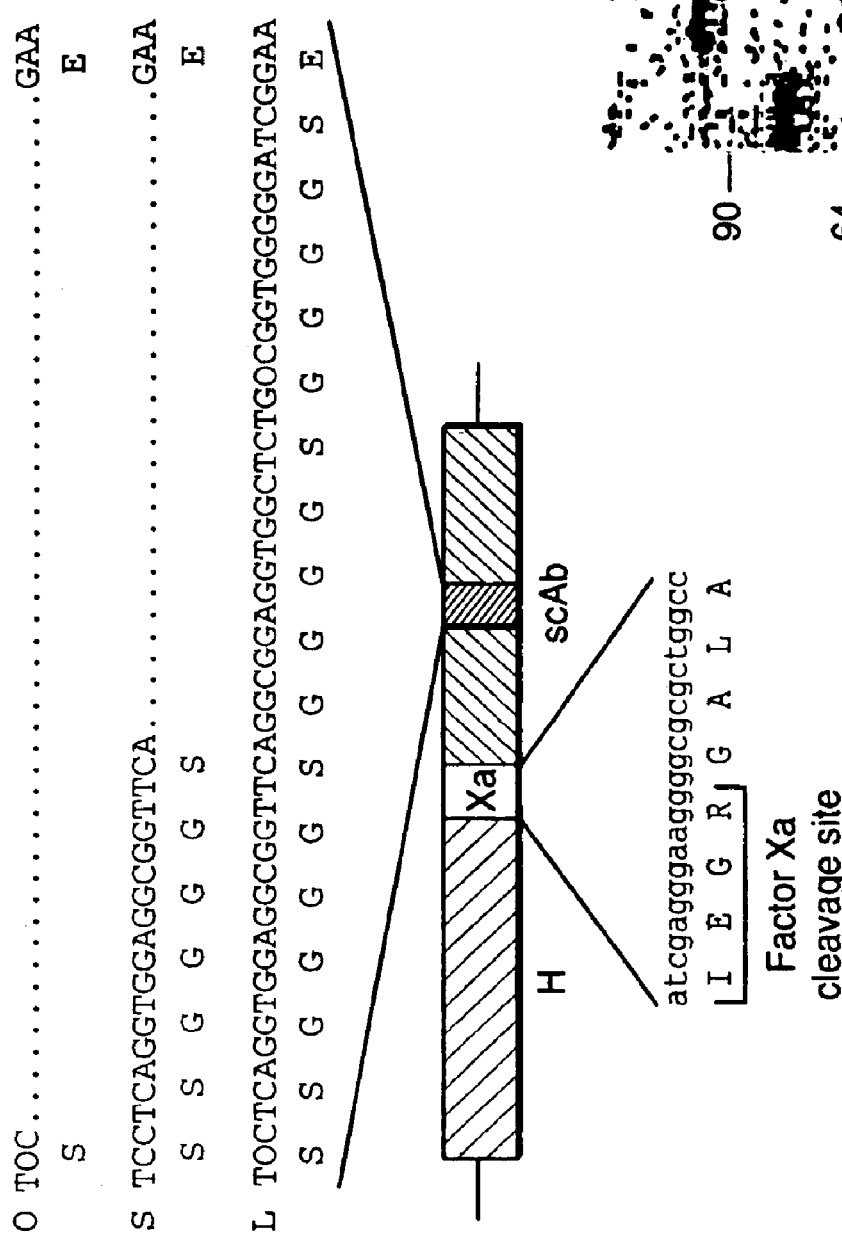
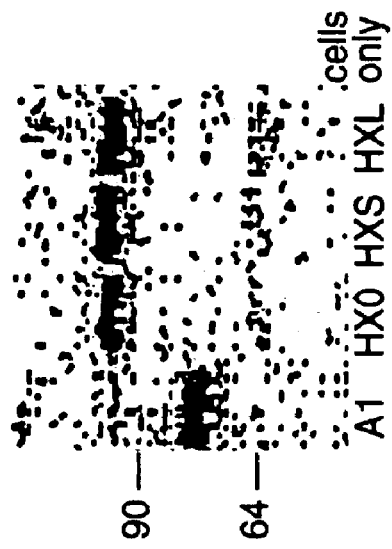
FIG. 8A
FIG. 8B

|       | MV | MV-HXL |     |
|-------|----|--------|-----|
| 98 —  |    | ▬      | HXL |
|       | ▬  |        | H   |
| 64 —  | ▬  | ▬      | N   |
| 50 —  |    |        |     |
|       | ▬  | ▬      | M   |

FIG. 11A

|       | MV    | MV-HXL |          |
|-------|-------|--------|----------|
|       |       | ▬      | HXL      |
| 98 —  | ▬ ▬   | ▬      | H        |
|       | − +   | − +    | Factor Xa |

FIG. 11B

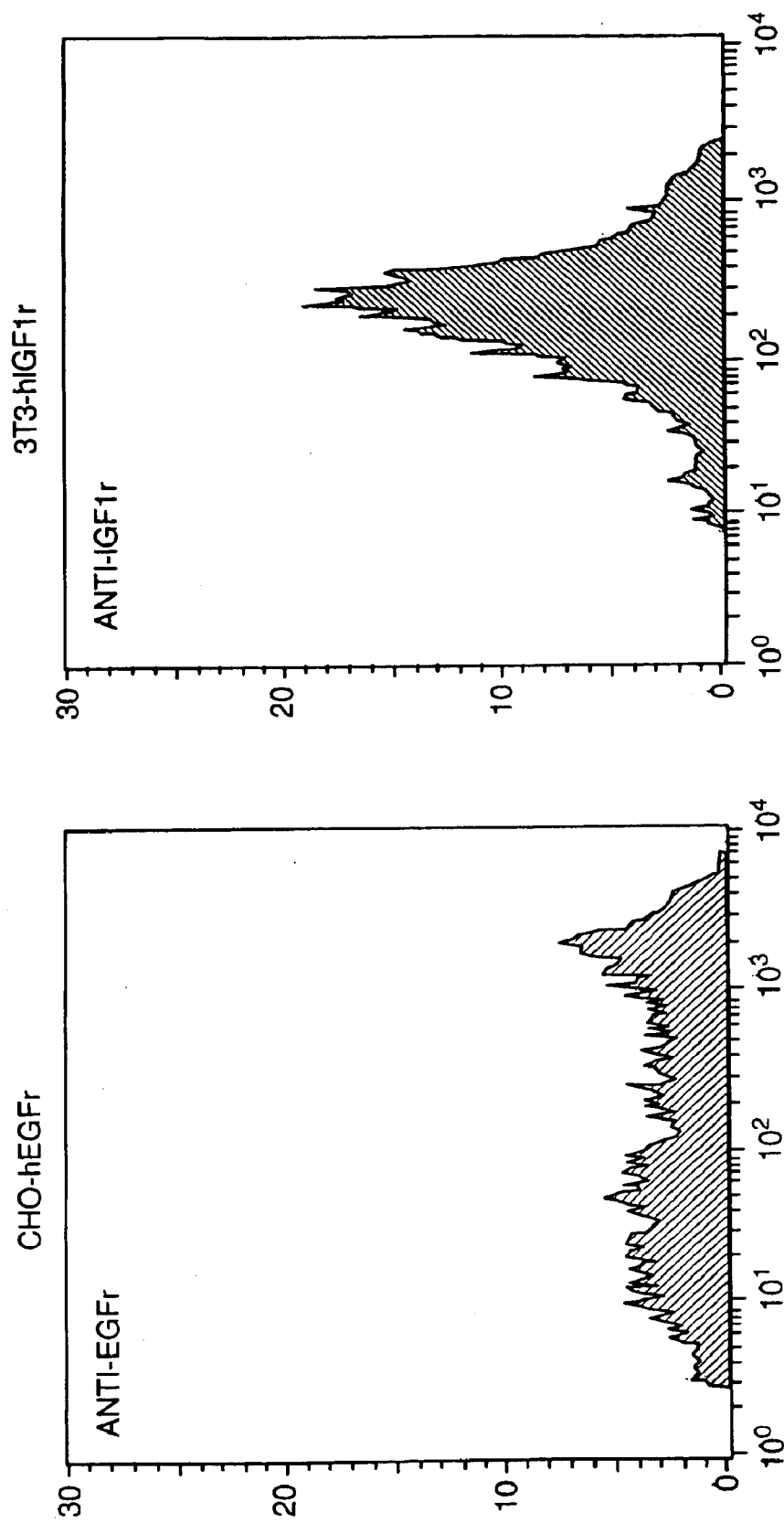

FIG. 18B

THERAPEUTIC METHODS AND COMPOSITIONS USING VIRUSES OF THE RECOMBINANT PARAMYXOVIRIDAE FAMILY

This application claims priority to U.S. Provisional Application Ser. No. 60/155,873, filed Sep. 24, 1999, the entirety of which is incorporated by reference herein.

FIELD OF THE INVENTION

The invention relates relates to methods for production and use of genetically altered paramyxoviruses for the treatment of cancer.

BACKGROUND

The family Paramyxoviridae are negative strand RNA viruses known to be responsible for a variety of human and veterinary diseases. The family contains four genera: (i) *Paramyxovirus* (Sendai virus; parainfluenza virus, types I and III; mumps virus), (ii) *Morbillivirus* (measles virus; rinderpest virus; phocine distemper virus; and canine distemper virus, (iii) *Rubulavirus* (Simian virus type V; Newcastle disease virus), and (iv) *Pneumovirus* (human respiratory syncytial virus; bovine respiratory syncytial virus).

Paramyxoviridae viruses are enveloped, so possess membrane 'spike' glycoproteins which are responsible for viral attachment to cell surfaces via a specific receptor and for mediating virus-cell membrane fusion. Subsequent to receptor binding, these viruses enter cells by direct fusion of the viral and host cell membranes. Viruses which fuse at the target cell membrane in a pH-independent manner are activated for fusion by the receptor binding event itself triggering conformational changes in the envelope glycoprotein. The ability of viruses to fuse directly with the target cell membrane is strongly associated with a tendency to trigger membrane fusion between infected and neighboring uninfected cells, the visible outcome of which is the formation of large multinucleated syncytia centering on a single infected cell.

Unmodified mumps virus administered as a tissue culture supernatant to 90 patients with terminal malignancies by intratumoral, oral, rectal or intravenous inoculation, or by inhalation, and resulted in significant tumor regressions (between 50 and 100%) in 37 of the patients treated, with minor responses in a further 42 patients (Asada 1974 Cancer 34 1907). The activity of mumps virus was not confined to a single tumor type, but was apparent in a range of different epithelial and nonepithelial malignancies.

Newcastle disease virus, an avian *Paramyxovirus*, has been used to infect cancer cells which have been removed from the patient, and are then irradiated and administered to the patient as a vaccine to elicit an antitumor immune response.

While certain Paramyxoviridae viruses have been used for cancer treatment, there is a need in the art for Paramyxoviridae viruses which are selectively cytotoxic for tumor cells such that the virus will spread rapidly and selectively through neoplastic tissues while sparing normal host tissues. There also is a need for a convenient and reliable method for monitoring the spread of the virus and the virus load in the treated patient.

SUMMARY OF THE INVENTION

In one aspect, the invention encompasses a method of monitoring a reduction in tumor size in a patient, comprising administering to a patient having a tumor a replication-competent Paramyxoviridae virus comprising a nucleic acid sequence encoding a heterologous polypeptide, wherein upon administration the heterologous polypeptide is detectable in a biological fluid of the patient, and detection of the heterologous polypeptide is indicative of Paramyxoviridae virus growth in the patient and reduction in tumor size. In one embodiment, the heterologous polypeptide is biologically inactive in the patient. In another embodiment, the Paramyxoviridae virus comprises a chimeric gene encoding a recombinant fusion protein comprising the heterologous polypeptide fused to an endogenous polypeptide. In still another embodiment, the recombinant fusion protein comprises an amino acid linker sequence between the heterologous polypeptide and the endogenous polypeptide, wherein the amino acid linker sequence comprises a protease cleavage site.

The invention also encompasses a method of increasing the fusogenicity on tumor cells of a Paramyxoviridae virus, comprising contacting tumor cells with a replication-competent Paramyxoviridae virus comprising one or more of a recombinant F protein, H protein, or M protein of the Paramyxoviridae virus that increases fusogenicity of the virus with the cells.

The invention also encompasses a method of reducing tumor size in a patient, comprising administering to a patient having a tumor a replication-competent Paramyxoviridae virus comprising one or more of a recombinant F, H, or M protein of the Paramyxoviridae virus having increased fusogenicity of the virus with cells of the tumor.

The invention also encompasses a method of reducing tumor size in a patient, comprising administering to a patient having a tumor a replication-competent Paramyxoviridae comprising a nucleic acid sequence encoding a cytokine, wherein the administration results in reduced tumor size.

The invention also encompasses a method of reducing tumor size in a patient, comprising administering to a patient having a tumor a Paramyxoviridae virus that is specific for cells of the tumor. Preferably, the Paramyxoviridae virus comprises a viral surface ligand that specifically binds to a receptor on a tumor cell. In one embodiment, the ligand is fused via an intervening amino acid linker to a Paramyxoviridae virus surface protein to form a ligand/virus recombinant protein such that the fusion protein specifically binds to the receptor on the tumor cell. In another embodiment, the amino acid linker of the fusion protein comprises a protease cleavage site for a protease produced by the tumor cell, such that cleavage of the cleavage site by the protease produced by the tumor cell permits infection of the tumor cell by the Paramyxoviridae virus.

Preferably, the virus surface protein is one of F protein or H protein.

Preferably, the ligand is a single chain antibody specific for carcinoembryonic antigen and the tumor cell receptor is carcinoembryonic antigen.

Preferably, the furin cleavage sequence of the Paramyxoviridae virus F protein is removed and replaced with a cleavage sequence of a protease produced by the tumor cell.

The invention also encompasses a method of producing a recombinant Paramyxoviridae virus comprising, in order, the steps of: 1) transfecting a eukaryotic cell line stably expressing T7 RNA polymerase with an infectious Paramyxoviridae viral genomic cDNA under the control of a 17 promoter; 2) infecting the transfected cells of step (1) with a helper virus expressing a selectable trait, and Paramyxoviridae viral N, P and L proteins; 3) contacting the infected, transfected cells of step (2) with cells that permit Paramyxoviridae virus infection and replication, under conditions permitting the infection and replication; 4) selecting syncytia formed on the cells that permit Paramyxoviridae virus infection and replication; 5) screening for and isolating the Paramyxoviridae lacking helper viral genetic material based upon the presence or absence of the selectable trait of the helper virus; and 6) expanding the Paramyxoviridae virus lacking helper viral genetic material to produce the recombinant Paramyxoviridae virus. In one embodiment, the selectable trait is deletion of F protein. In another embodiment, the selectable trait is expression of an F protein that is cleavable by a protease other than furin. In another embodiment, the selectable trait is expression of GFP.

The invention also encompasses a kit for treatment of a patient having a tumor, the kit comprising a replication-competent Paramyxoviridae virus comprising one or more of: a) a nucleic acid sequence encoding a heterologous polypeptide, wherein upon the administration the heterologous polypeptide is detectable in a biological fluid of the patient, and detection of the heterologous polypeptide is indicative of Paramyxoviridae virus growth in the patient and reduction in tumor size; b) a recombinant F protein, H protein, or M protein of the Paramyxoviridae virus that increases fusogenicity of the virus with the cells; c) a nucleic acid sequence encoding a cytokine; and d) a Paramyxoviridae virus that is specific for cells of the tumor.

The invention also encompasses a method of treating a patient having a tumor in order to reduce tumor size, comprising administering to the patient a replication-competent Paramyxoviridae virus comprising two or more of: a) a nucleic acid sequence encoding a heterologous polypeptide, wherein upon the administration the heterologous polypeptide is detectable in a biological fluid of the patient, and detection of the heterologous polypeptide is indicative of Paramyxoviridae virus growth in the patient and reduction in tumor size; b) a recombinant F protein, H protein, or M protein of the Paramyxoviridae virus that increases fusogenicity of the virus with the cells; c) a nucleic acid sequence encoding a cytokine; and d) a Paramyxoviridae virus that is specific for cells of the tumor.

In one embodiment, in any of the inventive methods and compositions, the Paramyxoviridae virus is selected from the group consisting of *Paramyxovirus, Morbillivirus, Rubulavirus* and *Pneumovirus*. In another embodiment, the *Paramyxovirus* is one of mumps virus, parainfluenza viruses type I or III, and Sendai virus. In still another embodiment, the *Morbillivirus* is one of measles virus, rinderpest virus, phocine distemper virus, and canine distemper virus. In a further embodiment, the *Rubulavirus* is one of Newcastle disease virus and Simian virus V. In still a further embodiment, the *Pneumovirus* is one of human respiratory syncytial virus and bovine respiratory syncytial virus.

BRIEF DESCRIPTION OF THE DRAWINGS

FIG. 1 shows a schematic diagram of the plasmid encoding MV H protein fused to a C peptide heterologous polypeptide that is either cleavable (pCGH FurCP) or non-cleavable (PCGH G4S CP).

FIG. 2 shows a schematic diagram of the construction of the plasmid p(+)MPGFPV from the plasmid p(+)MPCATV.

FIG. 3 shows a schematic diagram of the intermediate plasmid construct p(+)MPIrGFPV.

FIG. 4 shows a schematic diagram of the plasmid p(+) MIrGFPNV.

FIG. 5. Generation and characterization of recombinant MV with targeting specificity for CD38. Schematic representation of the genome of recombinant MV displaying single chain antibodies as C-terminal fusions to H glycoprotein. The scFvs are linked to H glycoportein via a Factor Xa protease cleavage (IEGR) site.

FIGS. 6A–D. recombinant MV displaying anti-CD38 antibody efficeintly infects CD38-expressing CH) cells. The CHO0CD38 target cells are infected with (A)- anti-CD38 MV or (B) anti-CD52 MV. The number of infectious centers (synctia with >20 nuclei) were counted and expressed as syncytial forming units/ml of virus. (C) Virus output from CHO-CD38 and (D) expressed as syncytial forming units/ml of virus. (C) Virus output from CHO-CD38 and (D) Vero cells, 48 hours following infection wih untreated (black histogram or Factor Xa protease treated (grey histogram) ti-CD38 or anti-CD52 viruses.

FIG. 7. Immunoblot to demostrate that the recombinant MV expresses hybrid glycoproteins.

FIGS. 8A–B: (A) Schematic Diagram Showing The Relative Positions Of MV H, Spacer Incorporating Factor Xa Cleavage Site And Appended Scab. The Linker Sequences Separating $V_H$ And $V_L$ In The Three Scab Forms, Indicated As 0, S And L, Are Also Given. (B) HαCEA Are Expressed At The Expected Molecular Weight. Western Blot Analysis Using An αFlag Ab Of Vero Cells Transfected With The Indicated H Constructs Or Mock Transfected. Numbers Correspond To MW In Thousands.

FIGS. 9A–B: (A) MV-HXL infects and induces cell-cell fusion in CD46-negative, CEA-positive cells. Representative fields of view were photographed 72 hours post-infection with MV, MV-HXL (MOI 3) or no virus. (B) MV-HXL replicates in CD46-negative, CEA-positive cells. Infectivities were quantified by $TCID_{50}$ titration using the indicated cell lines as targets.

FIGS. 10A–D: (A) HXL protein induces syncytia formation in CD46-positive cells. Syncytia were scored 48 hours post-co-transfection with MV F and the indicated H constructs. (B) Expression levels of CD46 and CEA on all cell lines used in this study. Grey shading, no primary Ab as negative control; thin line, CEA; thick line, CD46. (C) and (D) HXL protein induces syncytia formation in CD46-negative, CEA-positive cells. Syncytia were scored (C) and photographed (D) 48 hours post-co-transfection with F and the indicated H constructs. For syncytia scoring, H and HXL on Vero cells were not countable as >90% of cells were in syncytia. Black arrows indicate isolated syncytia.

FIGS. 11A–C: (A) MV-HXL expresses an H protein of the expected molecular weight. Western blot analysis of purified particles with an MV-specific antiserum, numbers refer to MW in thousands. (B) Cleavage of the displayed scAb from MV-HXL by Factor Xa protease treatment. Western blot analysis of purified particles with an aMV serum following Factor Xa treatment (10 μg/ml, 2 hours, 23° C.), numbers refer to MW in thousands. (C) MV-HXL binds the surface of CD46-negative, CEA-positive cells. Bound virus (MOI 3) was detected by FACS analysis using mAb 129. Grey shading, no virus; thin line, MV; thick line, MV-HXL.

FIG. 12: MV-HXL infectivity for MC38-CEA cells is inhibited by cleavage of the displayed scAb or antibody preadsorption of cell surface CEA. Cells were infected with MV or MV-HXL (MOI 1), untreated or pretreated with 10 μg/ml Factor Xa. Also, cells were pretreated with 10 μg/ml αCEA COL1 Ab, then infected with MV or MV-HXL (MOI 1). Virus released from the cells by freeze/thaw 72 hours post-infection was quantified by $TCID_{50}$ titration on Vero cells.

FIGS. 13A–C: (A) HαCEA proteins are as stable as unmodified MV H. Pulse chase analysis of Vero cells transfected with the indicated H constructs. Antigenic material was precipitated after the indicated chase times in minutes. (B) HXL protein dimerizes with itself and with unmodified H. Vero cells co-transfected with the indicated constructs were radiolabelled and lysed. Material immunoprecipitated with αflag mAb was dissolved under non-reducing conditions, numbers refer to MW in thousands. (C) HX0, HXS and HXL are localized at the cell surface. FACS analysis using mAb 129 of MC38 cells transfected with the indicated H constructs. Grey shading, no primary Ab.

FIGS. 14A–E. Genomic structure, protein composition and replication of recombinant MV. (A) Plasmid p(+)MV-NSe coding for the MV antigenome (top), PacI-SpeI fragments used for subcloning (center), and amino acid sequences (one letter code) of the junctions between the H protein ectodomain and the specificity domains (bottom). Coding regions of the six MV cistrons are represented by solid black boxes, the transmembrane segment of the F and H proteins by an horizontally lined box, the FXa cleavage site and the flexible linker by a hatched box and the ligand by a gray box. Arginine residues in brackets have been deleted. For details see text. (B) Protein composition of recombinant viruses. Viral particles were purified by centrifugation through a 20% sucrose layer onto a 60% sucrose cushion and subsequent pelleting. The viruses were titrated, 5000 pfu were subjected to lysis, and proteins were separated by SDS-PAGE. For immunodetection a MV-specific antiserum was used. (C) FXa protease sensitivity of hybrid H proteins. Purified viral particles (5000 pfu) were lysed and incubated for 1 hour without (−) or with (+) FXa protease at room temperature. Proteins were separated by SDS-PAGE and detected with a H-specific antiserum. (D) FACS analysis of CD46 (interrupted line), IGFlr (dotted line) and EGFr (continuous line) expression on Vero cells. Vertical axis: cell number. Horizontal axis: fluorescence intensity. The greyed profile represents incubation of the cells without the primary antibody. (E) Time course of released (right panel) and cell-associated (left panel) virus production in Vero cells infected with parental MV (diamonds), MV-H/XhEGF (squares) and MV-H/XhIGF1 (triangles). Cells were infected at a m.o.i. of 3 and incubated at 32° C. for the times indicated. Viral titers were determined by 50% end-point dilution. Indicated values are averages of three experiments.

FIGS. 15A–B. Binding of recombinant viral particles to (A) immobilized hEGF- and hIGF1-specific antibodies and to (B) rodent cells expressing a target receptor. (A) ELISA plates were coated either with anti-hEGF or anti-hIGF1 monoclonal antibodies. After blocking, the plates were incubated with different dilutions of MV-H/XhEGF and MV-H/XhIGF1. Bound virus was detected using an H-specific antiserum. (B) Expression levels of hEGFr in CHO-hEGFr cells (top left) and of hIGF1r in 3T3-hIGF1 cells (top right); cells incubated only with the secondary antibody showed background level of fluorence (mean 3.9 versus 466.5 for CHO-hEGFr cells and 5.7 versus 250.8 for 3T3-hIGF1 cells, data not shown). Binding of MV-H/XhEGF to CHO-hEGFr cells (bottom left) and of MV-H/XhIG1 to 3T3-hIGF1r cells (bottom right). Thick lines: incubations with the recombinant viruses. Thin lines: incubation with MV. Grey areas: control incubations without virus. Vertical axis: cells counted. Horizontal axis: fluorescence intensity.

FIGS. 16A–F. Infection of CHO-hEGFr cells, CHO-hEGFr.tr cells (G and H) and CHO cells (I and J) with $MV^{green}$-H/hEGF (A–D and G–J) or MV (E and F). Cells were infected at a m.o.i. of 1 and monitored by fluorescent- or phase-contrast microscopy 24 (A), 48 (B) or 72 (C–J) hours after infection.

FIGS. 17A–D. Infection of 3T3-hIGF1r cells with $MV^{green}$-H/XhIGF1r (A and B) or $MV^{green}$ (C and D). Cells were infected at a m.o.i. of 3 and infection was monitored by fluorescent- (A and C) or phase-contrast (B and D) microscopy 24 hours after infection.

FIGS. 18A–B. Competition of viral entry by soluble receptors (A) and effect of proteolytic cleavage of the specificity domain on entry (B). (A) Competition of viral infections by soluble EGF (sEGF, top panel) or soluble IGF1 (sIGF 1, bottom panel). CHO-hEGFr and Vero cells pretreated or not with sEGF were infected with $MV^{green}$ or $MV^{green}$-H/XhEGF at an m.o.i. of 0.3. 3T3-hIGFr and Vero cells pretreated or not with sIGF1 were infected with $MV^{green}$ and $MV^{green}$-H/XhIGF1 at an m.o.i. of 0.1. The percentage of infected cells was determined at 24 hours p.i. by counting GFP expressing cells in a standard area, and normalized to the number of GFP expressing cells in infections without added soluble receptor. Results obtained with MV Edmonston on Vero cells are indicated with gray columns. Results obtained with recombinant MV on Vero cells with white columns, and on rodent cells with black columns. (B) Effects of the treatment of recombinant viruses with FXa protease prior to infection. Vero, CHO-hEGFr or 3T3-hIGF1r cells were infected with $MV^{green}$-H/XhEGF or $MV^{green}$-H/XhIGF1 ($10^4$ pfi/well), respectively, pretreated with 0, 5 or 50 μg/ml FXa protease. The number of GEP expressing cells was determined 42 hours p.i. and normalized to untreated virus.

FIG. 19 shows that a heterologous polypeptide, CEA, can be used to track the replication of a therapeutic measles virus according to one embodiment of the invention.

DESCRIPTION

The invention is based upon the discovery that recombinant Paramyxoviridae viruses, containing modifications, either singly, or in combination, are advantageous for cancer therapy, in terms of safety, efficacy, and/or ability to monitor. The recombinant Paramyxoviridae viruses according to the invention enhance the therapeutic effect of a Paramyxoviridae virus relative to its unmodified counterpart.

Definitions

In order to more clearly and concisely describe and point out the subject matter of the claimed invention, the following definitions are provided for specific terms which are used in the following written description and the appended claims.

As used herein, the term "monitoring" refers to a process of determining the amount of viral replication or gene expression occurring in a host cell, tissue or organism.

As used herein, "Paramyxoviridae virus" refers to a negative strand RNA virus of the family Paramyxoviridae. The family Paramyxoviridae contains three genera: (i) *Paramyxovirus* (Sendai virus; parainfluenza virus, types I, II, III and IV; mumps virus; simian virus type V; Newcastle disease virus), (ii) *Morbillivirus* (measles virus; rinderpest virus; phocine distemper virus; and canine distemper virus, and (iii) *Pneumovirus* (respiratory syncytial virus, etc.).

As used herein, "reduction in tumor size" refers to any decrease in the size of a tumor following administration of a *paramyxovirus* relative to the size of the tumor prior to administration of the virus. A tumor may be considered to be reduced in size if it is at least 10% smaller, 25%, 50% up to 100% or no tumor remaining as measured by determination of tumor mass or size, either measured directly in vivo (i.e., by measurement of tumors directly accessible to physical measurement, such as by calipers) or by measurement of the size of an image of the tumor produced, for example by X-ray or magnetic resonance imaging.

By "patient" is meant an organism which is a donor or recipient of explanted cells or the cells themselves. "Patient" also refers to an organism to which viruses of the invention can be administered. Preferably, a patient is a mammal, e.g., a human, primate or a rodent.

As used herein, the term "replication-competent" refers to a virus that is fully capable of infecting and replicating in a host cell. A replication-competent virus requires no additional viral functions supplied by, for example, a helper virus or a plasmid expression construct encoding such additional functions.

As used herein, the term "conditions permitting the infection and replication" refers to the collection attributes of a cell or its surroundings that allow a given virus to infect (i.e., to insert its genetic material into the host, express proteins from the genetic material and replicate its genetic material), and assemble new infectious particles in, a host cell.

As used herein, the term "detectable" refers to a property of a polypeptide that allows one to determine the presence and/or amount of the polypeptide in a biological sample. The meaning of the term "detectable" is intended to encompasses detection of activities, for example, enzyme activity or fluorescence activity possessed by the polypeptide, in addition to detection of the polypeptide by other means, for example, immunoassay or mass spectroscopy.

As used herein, the term "biological fluid" refers to any extracellular bodily fluid, including but not limited to blood, urine, saliva, interstitial fluid, lymph, and cerebrospinal fluid.

As used herein, "Paramyxoviridae virus growth" refers to growth or replication of a virus of the Paramyxoviridae family as measured by viral propagation by successive rounds of infection and replication occurring in a host organism, or as measured by virus titer, or as measures by detection of a heterologous polypeptide, or as measured by a reduction in tumor size.

As used herein, the term "selecting syncytia" refers to the process of physically isolating or harvesting syncytia from a monolayer culture infected with a Paramyxoviridae virus in order to further propagate the particular form of the virus contained within a particular syncytium.

As used herein, the terms "wild-type" or "wild-type virus" refer to the characteristics of a virus of the family Paramyxoviridae as it is found in nature. The terms may be applied to any strain of a virus of the family Paramyxoviridae that occurs in nature, such as the Edmonston B strain of measles virus or other non-genetically engineered virus and can include point mutations.

As used herein, the term "recombinant" refers to a virus or polypeptide which is altered by genetic engineering, by modification or manipulation of the genetic material encoding that polypeptide or found in the virus such that it is not identical to the naturally occurring virus, or a naturally occuring variant of the virus, or polypeptide.

As used herein, the term "screening for and isolating" refers to a process whereby a particular virus is first identified on the basis of a particular characteristic or selectable trait, and then isolated or isolated and expanded from among a population of viruses.

As used herein, the term "based on the presence or absence of the selectable trait" refers to a selection process whereby a virus exhibiting a particular characteristic is selected from among a population of viruses not exhibiting that characteristic on the basis of selection for or against that characteristic. For example, if one wishes to select viruses that do not contain a fluorescent marker, one will select a virus based on the absence of fluorescence in infected cells. If, on the other hand, one wishes to select virus that has a fluorescent marker, one will select such a virus based on the presence of fluorescence in infected cells.

As used herein, the term "expanding" refers to the process whereby a particular virus is propagated in host cells in order to increase the available number of copies of that particular virus, preferably by at least 2-fold, more preferably by 5–10-fold, or even by as much as 50–100-fold relative to unexpanded cells.

As used herein, the term "heterologous polypeptide" refers to a polypeptide not found in nature in the *Paramyxovirus* strain that is modified to contain a sequence encoding the polypeptide.

As used herein, "biologically inactive" refers to the property of a polypeptide whereby the polypeptide does not influence the propagation or cytotoxicity of a Paramyxoviridae virus.

As used herein, "endogenous polypeptide" refers to a polypeptide that occurs in nature in the strain of Paramyxoviridae virus into which a heterologous polypeptide is inserted.

As used herein, the term "expression of GFP" refers to the production of green fluorescent protein, or a portion thereof retaining fluorescence activity, wherein such production is encoded by a virus that infects a cell.

As used herein, the term "amino acid linker sequence" refers to a sequence of amino acids that physically links and is located between two polypeptides or polypeptide regions. A linker is from 6 amino acids to 50 amino acids or from 10 amino acids to 30 amino acids and is preferably 15 amino acisd.

A "protease cleavage site" useful in the invention is a contiguous sequence of amino acids connected by peptide bonds which contains (i) a pair of amino acids which is connected by a peptide bond that is hydrolyzed by a particular protease.

As used herein, the term "deletion of F protein" refers to a helper virus that does not express an F protein capable of cooperating with H protein to induce virus-cell or cell-cell fusion.

As used herein, the term "F protein that is cleavable by a protease other than furin" refers to a Paramyxoviridae virus F protein requiring proteolytic cleavage by an enzyme other than furin for the ability to promote virus-cell or cell-cell fusion. Furin is a protease that cleaves F proteins of Paramyxoviridae viruses; therefore a method of selection dependent on proteolytic cleavage of F protein must exclude expression of furin-cleavable F protein by a helper virus. A protease used in selection against viruses containing helper viral genomic material is preferably one that may be added to or removed from cell culture medium.

As used herein, the term "increasing the fusogenicity" refers to a change in the rate or degree to which a particular modified virus induces cell-cell fusion in an infected host.

As used herein, the term "cytokine" refers to a protein that stimulates the immune response in a patient.

As used herein, the term "stimulates the immune response" means that a selected response against the tumor or antigens of the tumor is faster, more efficient, more easily induced, and/or greater in magnitude relative to the absence of administration of a virus according to the invention. The selected immune response can be stimulation or activation of a selected immune response, e.g., selective enhancement of an immune response to the tumor cells.

As used herein, the term "specific for" refers to a Paramyxoviridae virus that infects only host cells exhibiting a particular characteristic, such as a particular cell surface antigen or polypeptide, or refers to a specific interaction between a ligand and its cognate receptor to the exclusion of other interactions involving other ligands and receptors.

As used herein, the term "selectable trait" refers to a characteristic that allows one to retain or remove cells or viruses possessing and exhibiting that trait on the basis of that trait. A selectable trait may allow positive selection, wherein cells or viruses exhibiting that trait are selectively retained. Alternatively, a selectable trait may be a negative selectable trait, whereby cells or viruses exhibiting that trait are deleted or removed from a population.

Recombinant Paramyxoviridae Viruses According to the Invention

A. Modifications Allowing Monitoring of the Course of Infection and/or Treatment It is important to monitor the expression of a therapeutic virus during the course of treatment. In one embodiment, the invention provides a genetically engineered Paramyxoviridae viruses which encodes a heterologous polypeptide. The heterologous polypeptide is released from infected cells into a body fluid where its concentration can be monitored, making it a marker which provides an index of the total number of virus producing cells in the body.

I. Heterologous Polypeptides.

A heterologous polypeptide useful according to the invention is any polypeptide that is selected according any, or all, of the following criteria: (1) It is preferably small (e.g., having a molecular weight below 10 kilodaltons (kD)) and soluble in biological fluids so as to allow rapid equilibration between interstitial and intravascular fluid spaces in the body; (2) there should be a convenient, sensitive, specific, and accurate assay available for detection of the polypeptide; (3) the background level of expression of the heterologous polypeptide should be negligible in the biological fluid being tested or there should be a reliable method to discount background levels when interpreting an assay; (4) The biodistribution, metabolism and excretion of the peptide should be well characterized and its plasma half-life should be known; (5) the heterologous polypeptide should be relatively nonimmunogenic so that its half-life will not be influenced by a human immune response (e.g., the polypeptide is not be cleared from the body before it is monitored); and (6) the heterologous polypeptide preferably either lacks biological activity or only has a biological activity that is advantageous to the outcome of the therapy.

A heterologous polypeptide is used to monitor viral growth and is readily detectable in biological fluid samples. Preferably, the heterologous polypeptide is non-immunogenic, meaning that it is not likely to produce any significant immune response in the host organism undergoing gene therapy with the heterologous polypeptide. The heterologous polypeptide is also preferably non-functional, which means that it lacks any significant known biological activity other than that required to serve its use as a heterologous polypeptide (i.e., an activity that is detectable).

Both the properties of non-immunogenicity and non-functionality are merely intended to improve the performance of the heterologous polypeptide by preventing undesirable side effects in the host organism. The requirements of non-immunogenicity and non-functionality are not intended to be absolute, and it is understood that a heterologous polypeptide of the invention may possess an insignificant remnant of biological activity or immunogenicity in the host organism and may possess significant immunogenicity or biological activity in an organism other than the host organism.

i. Naturally Occurring Heterologous Polypeptides as Markers a. Cleavage Products as Markers Naturally occurring polypeptides with very low background levels of expression are ideally suited to be heterologous polypeptides since they are usually non-immunogenic. In one embodiment, a biologically inactive polypeptide is used which is a cleavage product of a prohormone processing reaction. In one embodiment, the heterologous polypeptide is C-peptide, which is the cleavage product of the prohormone proinsulin, which is found in plasma at levels of C-peptide, 170–900 pmol/l (proinsulin being found at 3–20 pmol/l, fasting insulin, being found at 43–186 pmol/l). Both endogenous insulin and C-peptide levels can be suppressed using somatostatin for improved background correction, and C-peptide peripheral kinetics have been extensively studied in both normal volunteers and diabetic patients. Patients with type I diabetes do not synthesize insulin and therefore have zero background levels of C-peptide (K. S. Polonsky et al., J. Clin. Invest. 77: 98–105 (1986)). An assay for quantifying C-peptide in human blood is described in P. C. Kao et al., Ann. Clin. Lab. Science 22: 307–316 (1992), the entirety of which is incorporated by reference herein.

Other polypeptide cleavage products encompassed within the scope of the invention, include, but are not limited to, proopiomelanocortin, preproenkephalin, preprodynorphin, preprovasopressin, preprooxytocin, preprocorticotrophin releasing factor, preprogrowth hormone releasing factor, preprosomatostatin, preproglucagon, preprogastrin, preprocalcitonin, preproepidermal growth factor, preprobradykinin, preprotachykinin, preangiotensinogen, preprovasoactive intestinal peptide and other peptide hormone precursors (J. Douglass et al., Ann. Rev. Biochem. 53: 665–715 (1984); D. H. Lynch and S. H. Snyder, Ann. Rev. Biochem. 55: 773–799 (1986); J. C. Hutton, Diabetalogia 37 (suppl. 2): S48–S56 (1994)).

b. Activation Peptides as Markers

In another embodiment of the invention, the activation peptides released during the proteolytic processing of zymogens to generate active enzymes (e.g., proteases) are used to provide heterologous polypeptides. In one embodiment, the activation peptide released by a pancreatic proenzyme during its trypsin-induced activation is used as a heterologous peptide. Most such peptides are small (less than 1 kDa) and rapidly excreted in the urine, enabling urine tests to be performed as a quick semi-quantitative assay for viral expression, such as the assay described in Mithofer, et al., Anal. Biochem. 230: 348–350 (1995).

In another embodiment, the activation peptide of procarboxypeptidase B which is about about 10 kD (K.K. Yamamoto et al., J. Biol. Chem. 267: 2575–2581 (1992)) is used as a heterologous protein, because it can be readily measured in serum or urine (see, e.g., Appelros, et al., Gut 42: 97–102 (1998)). In still another embodiment, the activation peptides derived from enzymatic cascade reactions (e.g., such as blood clotting are used) are used as heterologous proteins since they can be assayed be routine techniques (see, e.g., Philippou, Brit. J. Haem. 90: 432–437 (1995)).

c. Inactivation Peptides as Markers

In a further embodiment, heterologous polypeptides are used which are the fragments of hormones, proteases, or other biological molecules that have be proteolytically inactivated. In this embodiment, peptides are selected which are relatively non-immunogenic and non-biologically functional, as discussed above. Examples of such polypeptides include complement peptides C3b (iC3b), C4c and C4d (see, e.g., U.S. Pat. No. 5,981,481), the peptide fragments of endorphins, enkephalins, or atrial natriuretic peptide (ANP) (see, e.g., 5,731,306 and 5,714,347), and the inactivation peptides of thyrotropin-releasing hormone (TRH), substance P, neurotensin, and vasopressin (see, e.g., EP-A 468469), and the like.

d. Tumor Antigens as Markers

Convenient, sensitive assays have been developed to detect tumor antigens in the blood, and therefore, in one embodiment, the heterologous polypeptide is a tumor antigen which is produced in excessive amounts by a specific tumor subtype not found in the patient being treated. In one embodiment of the invention, the antigen is selected from the group consisting of CA125 (specific for ovarian cancer), alphafetoprotein (AFP, specific for liver cancer), carcinoembryonic antigen (CEA, specific for colon cancer), intact monoclonal immunoglobulin or light chain fragments (specific for myeloma), and the beta subunit of human chorionic gonadotrophin (HCG, specific for germ cell tumors).

Figure 19:
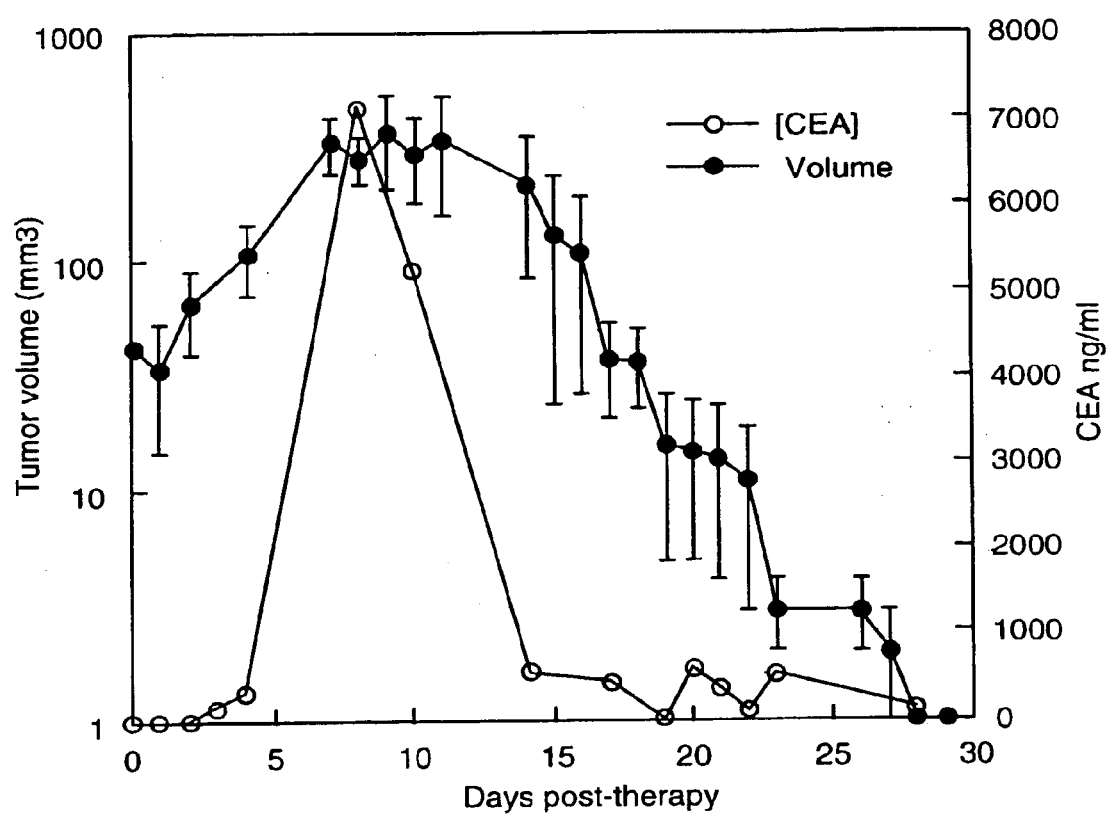

CEA is an example of a large polypeptide (its molecular weight is between 175 kD-200 kD) which can be used successfully as a heterologous marker polypeptide. Although the size of the polypeptide prevents it from being filtered by the kidney and excreted in the urine, CEA can be measured in the blood where its half life is approximately 5 days. Because CEA accumulates over time and equilibrates with the extracellular fluid compartment, total body CEA production can be calculated from a knowledge of its half-life and total body extracellular fluid volume. In the early stages after infection with a paramyxovirus bearing a CEA heterologous peptide, CEA accumulates in extracellular fluid at the site of release and diffuses only slowly into blood vessels. However, as shown in FIG. 19, taking this lag time into account the appearance of CEA correlates well with the replicative spread of virus in a tumor and tumor regression.

e. Inactive Variants as Markers

In another embodiment of the invention, heterologous polypeptides are inactive variants of naturally occurring peptides and are detected using variant specific antibodies. Methods of generating variant antibodies are well known in the art and are dislosed in, U.S. Pat. No. 6,077,519, U.S. Pat. No. 6,054,273, U.S. Pat. No. 6,022,683, and U.S. Pat. No. 5,773,222, the entireties of which are incorporated herein by reference.

In one embodiment, the fragment or sequence variant derived from the active portion of any polypeptide hormone is used as a marker. Polypeptide hormones encompassed within the scipe of the invention, include, but are not limited to, gastrin, renin, prolactin, adrenocorticotrophic hormone, parathyroid hormone, parathyroid hormone related polypeptide, arginine vasopressin, beta endorphin, atrial naturetic factor, calcitonin, insulin, insulin-like growth factor, glucagon, osteocalcin, erythropoietin, thrombopoietin, human growth hormone, and others.

Analogous hormones from other non-human species are also a source of peptide sequences which can be adopted or modified to serve as a marker polypeptide in the invention.

Many of the commercially available assays for such hormones have the power to detect biologically inactive, truncated, or point-mutated variants of the natural polypeptide. For example, deletion of the first six N-terminal amino acids of parathyroid hormone (an 84 residue polypeptide whose normal blood level is 1.0–5.2 pmol/l) destroys biological activity, but the truncated molecule is still detectable using a standard immunoassay.

An unprocessible variant of a naturally occurring precursor polypeptide can also serve as a heterologous marker polypeptide. For example, proinsulin is processed to insulin and C-peptide by cellular proteases that cleave the junctions between the C-peptide and the A and B chains. Processing can be inhibited by mutation of these cleavage sites, such that the inactive, point-mutated proinsulin (normal level 3–20 pmol/l) will be released from the cell and detected in the blood. Similarly, variants of naturally occurring polypeptides with prolonged circulating half-lives can be used as marker polypeptides. Peptide elimination can be reduced by modifications that increase size or anionic charge (reduced glomerular filtration), by mutations in the recognition sites for inactivating proteases, and by mutations that lead to loss of receptor binding activity (reduced receptor-mediated clearance) (C. McMartin, Biochem. Soc. Trans. 17: 931–934 (1989)).

ii. Synthetic Non-Human Peptide as Markers

A fully synthetic or a non-human peptide is also useful as a heterologous marker polypeptide. Such peptides have been used to monitor protein expression and to track synthetic proteins during purification (e.g., FLAG tag, myc tag, strep tag). Similar peptides can be designed which lack immunogenicity in humans. To design such a peptide, one may use a peptide derived from a protein not known to be immunogenic or use a peptide derived from a self protein not known for autoimmunity. As used herein, "relatively non-immunogenic" refers to a protein or peptide that does not elicit a deleterious immune response in a majority of treated individuals, that is an immune response that compromises the patients' health or that interferes with detection of the heterologous polypeptide or the reduction in tumor size that is achieved in the absence of the marker polypeptide. If there is an immune response to a selected peptide, it is preferred that the response is cell-mediated, rather than antibody-mediated, since the primary concern for the marker peptide is the half-life of the peptide.

2. Inserting Marker Polypeptide Encoding Sequences Within the Viral Genome

A sequence encoding a marker polypeptide according to the invention may be inserted into the Paramyxoviridae virus genome using a plasmid containing the Paramyxoviridae virus genome coding sequences, such as p(+)MV (Radecke et al., 1995, EMBO J. 14: 5773; EMBL Accession No. Z66517), and standard molecular cloning techniques (Sambrook et al., *Molecular Cloning: A Laboratory Manual*, Second Edition, 1989, (Cold Spring Harbor Press, Cold Spring Harbor, N.Y.); Ausubel et al., 1988, *Current Protocols in Molecular Biology*, (John Wiley and Sons, Inc., New York); Ausubel et al., 1992, *Short Protocols in Molecular Biology*, (John Wiley and Sons, Inc., New York).

Restriction enzyme cleavage sites occurring between the coding sequences of the MV genome include, but are not limited to BsiWI, SpeI and AatII (between the P and M coding units), NarI (between the M and F coding units), PacI (between the F and H coding units) and SpeI between the H and L coding units of the p(+)MV plasmid. Sequences may be engineered by one of skill in the art to be compatible with insertion into any of these cloning sites. Alternatively, any of these sites may be modified by insertion or deletion of sequences to generate other restriction sites useful for insertion of marker polypeptide coding sequences. In addition to modification of the Paramyxoviridae virus genome intergenic sequences in the plasmid to generate new restriction sites, regulatory elements may be introduced to the intergenic region to aid in the expression of the inserted sequences. For example, translation stop codons may be introduced upstream of the new restriction sites, as may be promoter sequences to drive expression of the marker polypeptide.

3. Expression of Heterologous Polypeptides as Protease Cleavable Fusions i. Protease Sensitive Linkers The heterologous marker polypeptide can be introduced into the viral genome either as a protease-cleavable fusion to a virally encoded protein or as an independent expression unit within the viral genome. In this way, a fixed stoichiometric relationship will exist between the expression of the viral gene products and the marker peptide. In one embodiment of the invention, the heterologous protein is fused to viral protein by an amino acid acid linker sequence comprising a protease cleavage site. A protease cleavage site may include one or more amino acids on either side of the peptide bond to be hydrolyzed, to which the catalytic site of the protease also binds (Schecter and Berger, Biochem. Biophys. Res. Commun. 27, 157–62, 1967), or the recognition site and cleavage site on the protease substrate may be two different sites that are separated by one or more (e.g., two to four amino acids).

The specific sequence of amino acids in the protease cleavage site depends on the catalytic mechanism of the protease, which is defined by the nature of the functional group at the protease's active site, as discussed above. For example, trypsin hydrolyzes peptide bonds whose carbonyl function is donated by either a lysine or an arginine residue, regardless of the length or amino acid sequence of the polypeptide chain. Factor Xa, however, recognizes the specific sequence Ile-Glu-Gly-Arg (SEQ ID NO: 1), but hydrolyzes peptide bonds between Arg-Thr and Arg-Ile. Thus, a protease cleavage site comprises at least 2, 3, 4, 5, 6, 7, 8, 9, or 10 or more amino acids. Optionally, additional amino acids can be present at the N-terminus and/or C-terminus of the recognition site.

The invention permits a great deal of flexibility and discretion in terms of the choice of the protease cleavable linker peptide. The protease specificity of the linker is determined by the amino acid sequence of the linker. Specific amino acid sequences can be selected in order to determine which protease will cleave the linker, this is an important indication of the location of cleavage within the cell or following secretion from the cell and can have a major effect on the release of the marker polypeptide and its transportation through the body of the patient. The size in the linker can generally be varied. In one embodiment, the linker sequence is between 3 and 50 amino acids in length. More preferably the linker is between 5 and 25 amino acids in length, and most preferably the linker is between 8 and 15 amino acids in length.

In one embodiment, the amino acid linker is linked by a peptide bond to the C-terminus of the N-terminal polypeptide of the recombinant fusion protein and via a peptide bond to the N-terminus of the C-terminal polypeptide of the recombinant fusion protein. In one embodiment, the N-terminal polypeptide of the fusion protein is heterologous, and thus the C-terminal polypeptide is the viral polypeptide, while in another embodiment, the N-terminal polypeptide is the viral polypeptide and the C-terminal polypeptide is the heterologous polypeptide.

ii. Proteases for Use with the Linkers

Some proteases useful according to the invention are discussed in the following references: V. Y. H. Hook, *Proteolytic and cellular mechanisms in prohormone and proprotein processing*, RG Landes Company, Austin, Tex., USA (1998); N. M. Hooper et al., Biochem. J. 321: 265–279 (1997); Z. Werb, Cell 91: 439–442 (1997); T. G. Wolfsberg et al., J. Cell Biol. 131: 275–278 (1995); K. Murakami and J. D. Etlinger, Biochem. Biophys. Res. Comm. 146: 1249–1259 (1987); T. Berg et al., Biochem. J. 307: 313–326 (1995); M. J. Smyth and J. A. Trapani, Immunology Today 16: 202–206 (1995); R. V. Talanian et al., J. Biol. Chem. 272: 9677–9682 (1997); and N. A. Thornberry et al., J. Biol. Chem. 272: 17907–17911 (1997). A variety of different intracellular proteases useful according to the invention and their recognition sequences are summarized in Table 1.

TABLE 1

Properties Of Some Proteases Associated With Post-Translational Processing

| Protease | Sub-cellular Localization | Tissue Distribution | Cleavage Signal |
|---|---|---|---|
| furin | Golgi | ubiquitous | RXKR (SEQ ID NO:2) |
| MMP-2 | Golgi | tumor cells | PLGLWA (SEQ ID NO:3) |
| MT1-MMP | plasma membrane | tumor cells | PLGLWA (SEQ ID NO:3) |
| caspase-1 | secretory pathway | ubiquitous | YEVDGW (SEQ ID NO:4) |
| caspase-2 | secretory pathway | | VDVADGW (SEQ ID NO:5) |
| caspase-3 | secretory pathway | | VDQMDGW (SEQ ID NO:6) |
| caspase-4 | secretory pathway | | LEVDGW (SEQ ID NO:7) |
| caspase-6 | secretory pathway | | VQVDGW (SEQ ID NO:8) |
| caspase-7 | secretory pathway | | VDQVDGW (SEQ ID NO:9) |
| alpha-secretase | secretory pathway | ubiquitous | amyloid precursor protein (APP) |
| proprotein convertase (subtilisin/kexin isozyme SK1-1) | endoplasmic reticulum | ubiquitous | brain neutrophic growth factor precursor (RGLT) (SEQ ID NO:10) |
| tumor associated typsin | | tumor cells | |
| foot and mouth disease virus, protease 2A | | | NFDLLKLAGDVESNPGP (SEQ ID NO:11) |

While not intending to limit the scope of the invention, the following describes known proteases which might also be targeted by the linker, and their location in the cell. Proteases involved in the secretory pathway (ER/Golgi/secretory granules) includes, but are not limited to: Signal peptidase; Proprotein convertases of the subtilisin/kexin family (furin, PC 1, PC2, PC4, PACE4, PC5, PC); Proprotein convertases cleaving at hydrophobic residues (e.g., Leu, Phe, Val, or Met); Proprotein convertases cleaving at small amino acid residues such as Ala or Thr; Proopiomelanocortin converting enzyme (PCE); Chromaffin granule aspartic protease (CGAP); Prohormone thiol protease; Carboxypeptidases (e.g., carboxypeptidase E/H, carboxypeptidase D and carboxypeptidase Z); and, Aminopeptidases (e.g., arginine aminopeptidase, lysine aminopeptidase, aminopeptidase B).

Cytoplasmic proteases include, but are not limited to: Prolyl endopeptidase; Aminopeptidase N; Insulin degrading enzyme; Calpain; High molecular weight protease; and, Caspases 1, 2, 3, 4, 5, 6, 7, 8, and 9. For cytoplasmic proteins, it is necessary to use cleavage signals that are recognized by cytoplasmic proteases and to use heterologous marker peptides which have an appropriate hydrophilic/hydrophobic balance so that they can escape across the plasma membrane. For marker peptides that must escape the cell via diffusion across the cell membrane, small molecular size (e.g., <10 kDa) will advantageously promote egress of the peptide to the interstitial space.

Cell surface proteases or those occurring in the pericellular space include, but are not limited to: Aminopeptidase N; Puromycin sensitive aminopeptidase; Angiotensin converting enzyme; Pyroglutamyl peptidase II; Dipeptidyl peptidase IV; N-arginine dibasic convertase; Endopeptidase 24.15; Endopeptidase 24.16; Amyloid precursor protein secretases alpha, beta and gamma; Angiotensin converting enzyme secretase; TGF alpha secretase; TNF alpha secretase; FAS ligand secretase; TNF receptor-1 and —II secretases; CD30 secretase; KL1 and KL2 secretases; IL6 receptor secretase; CD43, CD44 secretase; CD 16-I and CD 16-II secretases; L-selectin secretase; Folate receptor secretase; MMP 1, 2, 3, 7, 8, 9, 10, 11, 12, 13, 14, and 15; Urokinase plasminogen activator; Tissue plasminogen activator; Plasmin; Thrombin; BMP-1 (procollagen C-peptidase); ADAM 1, 2, 3, 4, 5, 6, 7, 8, 9, 10, and 11; and, Granzymes A, B, C, D, E, F, G, and H.

iii. Self-Cleaving Linkers

An alternative to relying on cell-associated proteases is to use a sequence encoding a self-cleaving linker. In one embodiment of the invention, the foot and mouth disease vius (FMDV) 2A protease is used as linker. This is a short polypeptide of 17 amino acids that cleaves the polyprotein of FMDV at the 2A/2B junction. The sequence of the FMDV 2A propeptide is NFDLLKLAGDVESNPGP (SEQ ID NO: 11). Cleavage occurs at the C-terminus of the peptide at the final glycine-proline amino acid pair and is independent of the presence of other FMDV sequences and cleaves even in the presence of heterologous sequences.

Insertion of this sequence between two protein coding regions (i.e., the two halves of the fusion) results in the formation of a self-cleaving chimera which cleaves itself into a C-terminal fragment which carries the C-terminal proline of the 2A protease on its N-terminal end, and an N-terminal fragment that carries the rest of the 2A protease peptide on its C-terminus (see, e.g., P. deFelipe et al., Gene Therapy 6: 198–208 (1999)). Thus, instead of using a cleavage signal recognizable by a cell-associated protease, in this embodiment, the self-cleaving FMDV 2A protease sequence links the heterologous marker polypeptide to the viral polypeptide resulting in spontaneous release of the marker polypeptide from the viral polypeptide.

iv. The Viral Polypeptide Portion of the Fusion

The measles virus offers 6 six target viral polypeptides from which to create a fusion protein, the N (nucleocapsid) protein, P proteins (polymerase cofactor phosphoprotein), M (matrix) proteins, F (fusion) proteins, H (hemaglutinin) protein and L (large; RNA polymerase) protein. The *Rubulaviruses* offer seven target viral polypeptides, while the *pneumoviruses* offer ten. Each virus (measles, rubulavirus, and pneumovirus) encode, in order, at least N, P, M, F, H, and L proteins.

Viral proteins which are particularly useful fusion partners for a heterologous marker peptide include the F and H proteins which are expressed on the surface of the viral particle. When F and H proteins are used, cleavable linkers are provide a way to introduce the marker polypeptide into bodily fluids without reducing the bioactivity of the F or H protein being used. This is especially important because the syncytium-inducing abilities of Paramyxoviridae viruses reside in its membrane glycoproteins, which are responsible for mediating binding and fusion. Thus, the therapeutic or oncolytic activities of the virus reside in the F and H protein. In one embodiment of the invention, the F or H proteins are used to create fusion proteins. Sequence information relating to F and H proteins from a variety of paramyxoviruses can be found in Morrison T. and Portner A. "Structure, function, and intracellular processing of the glycoproteins of Paramyxoviridae." In *The Paramyxoviruses*, Kingsbury, D. W. ed., Plenum Press, New York and London. (1991).

In one embodiment of the invention, a cleavable linker is provided comprising a protease site for the same protease that activates the F protein, the subtilisin-like endoprotease furin in the trans-Golgi network for cleavage activation of the F protein. In one embodiment of the invention, an H protein is fused to a marker heterologous polypeptide through a linker comprising a furin cleavable site. Furin-cleavable marker polypeptides are therefore useful according to the invention when fused to proteins, such as F and H proteins, that are processed through the Golgi network. Fusing to H protein has been done by fusing the linker sequence to the extreme C-terminal residue of the H-protein. However, it is also possible to remove a few of the C-terminal residues (e.g., 0–20) and fuse onto the truncated C-terminus.

Although describing fusions between F and H proteins and heterologous marker polypeptides, any Paramyxoviridae virus protein, may be used as a fusion partner for a cleavable polypeptide as long as the fusion does not disrupt functions necessary for the replication of the virus in a host cell. In this embodiment, the heterologous marker can be cleaved from its fusion partner either within the host cell or external to the cell following display on the cell surface.

3. Adding Marker Polypeptide Cistrons

An alternative to the expression of a marker polypeptide as a cleavable fusion protein is to link the marker polypeptide sequence to a viral protein transcript through an internal ribosome entry site sequence (IRES). IRESs (also called ribosomal landing pads) are sequences that enable a ribosome to attach to mRNA downstream from the 5' cap region and scan for a downstream AUG start codon, for example in polycistronic mRNA. See generally, Miles et al., U.S. Pat. No. 5,738,985 and N. Sonenberg and K. Meerovitch, Enzyme 44: 278–91 (1990). Addition of an IRES between the coding sequences for a viral gene product and the marker peptide can enable the independent translation of either the viral gene product or the marker peptide from a dicistronic or polycistronic transcript.

IRES sequences can be obtained from a number of RNA viruses (e.g., picornaviruses, hepatitis A, B, and C viruses, and influenza viruses) and DNA viruses (e.g., adenovirus). IRES sequences have also been reported in mRNAs from eukaryotic cells (Macejak and Sarnow, Nature 353: 90–94 (1991) and Jackson, Nature 353: 14015 (1991)).

Viral IRES sequences are detailed in the following publications: (a) Coxsackievirus: Jenkins, O., J. Gen. Virol. 68: 1835–1848 (1987); Iizuka, N. et al., Virology 156: 64–73 (1987); and Hughes et al., J. Gen. Virol. 70: 2943–2952 (1989); (b) Hepatitis A virus: Cohen, J. I. et al., Proc. Natl. Acad. Sci. USA 84: 2497–2501 (1987); and, Paul et al., Virus Res. 8: 153–171 (1987); (c) *Poliovirus*: Racaniello and Baltimore, Proc. Natl. Acad. Sci. USA 78: 4887–4891 (1981); and Stanway, G. et al., Proc. Natl. Acad. Sci. USA 81: 1539–1543 (1984); (d) *Rhinovirus*: Deuchler et al., Proc.

Natl. Acad. Sci. USA 84: 2605–2609 (1984); Leckie, G., Ph.D. thesis, University of Reading, UK; and Skern, T. et al., Nucleic Acids Res. 13: 2111 (1985); (e) Bovine enterovirus: Earle et al., J. Gen. Virol. 69: 253–263 (1988); (f) *Enterovirus* type 70, Ryan, M. D. et al., J. Gen. Virol. 71: 2291–99 (1989); (g) Theiler's murine encephalomyelitis virus: Ohara et al., Virology 164: 245 (1988); and, Peaver et al., Virology 161: 1507 (1988); (h) Encephalomyocarditis virus: Palmenberg et al., Nucl. Acids Res. 12, 2969–2985 (1984); and Bae et al., Virology 170, 282–287 (1989); (i) Hepatitis C Virus: Inchauspe et al., Proc. Natl. Acad. Sci. USA 88: 10293 (1991); Okamoto et al., Virology 188: 331–341 (1992); and Kato et al., Proc. Natl. Acad. Sci. USA 87: 9524–9528 (1990); and (j) Influenza virus, Fiers, W. et al., Supramol. Struct. Cell Biochem. (Suppl 5), 357 (1981).

4. Independent Translation of a Heterologous Marker Polypeptide

Another alternative to the expression of a marker polypeptide as a cleavable fusion protein is to insert the sequence coding for the marker polypeptide between the coding sequences of the virus, allowing expression of the marker as an independent translation product. For example, the sequence encoding the marker may be inserted between the H and L protein coding sequences of the Paramyxoviridae virus genome, for example the MV genome. In this embodiment, the stoichiometry of the marker expression would be fixed relative to the expression of viral genes. However, it is well known that transcripts derived from the promoter-proximal end of the MV genome are more abundant than those derived from the promoter-distal end of the genome due to a gradient in the expression of shorter versus longer transcripts from U) the viral promoter. That is, the further away a given coding unit is from the viral promoter, the lower will be the number of transcripts containing that unit. Therefore, while the relative amount of a marker translated from a sequence inserted into the Paramyxoviridae virus genome between viral coding units will be constant with regard to the expression of viral proteins, the absolute amount of the marker transcript, and hence the marker polypeptide, will be influenced by its placement in the genome relative to the viral promoter. The further the coding unit is from the viral promoter, the lower will be the expression of the marker.

5. Assays for Heterologous Marker Polypeptides

Once the viral construct has been introduced into the patient, the release of the peptide marker can be monitored to determine whether and how much viral replication is occurring. A sample of an appropriate biological fluid or secretion is obtained from the patient and the concentration of the marker polypeptide in the fluid or secretion is determined. Any biological fluid or secretion known to the art can be employed, e.g., blood, urine, saliva, cerebrospinal fluid, mucous, or feces, but the choice of sample is likely to be determined by the target location of the construct within the body and the expected route of release and excretion of the marker polypeptide. Samples of the biological fluid can be obtained at any desired time interval following administration of the viral construct in order to monitor the effectiveness of transfection, the regulation of infection and/or the progress of therapy.

The presence of the marker polypeptide in the biological fluid sample can be evaluated by any qualitative or quantitative method known in the art. Immunologic assays such as ELISA or radioimmunoassay are preferred because of their specificity, sensitivity, quantitative results, and suitability for automation. Such assays are readily available in most medical facilities for a number of possible marker polypeptides such as insulin C-peptide and beta-HCG. Chromatographic methods such as HPLC, optionally combined with mass spectrometry, can also be employed. Other analytic methods are possible, including the use of specific color reagents, thin layer chromatography, electrophoresis, spectroscopy, nuclear magnetic resonance, and the like. While it is generally preferred that the marker polypeptide itself be nonfunctional, i.e., that it not possess any significant biological activity which might interfere with the patient's Z physiology or therapy, in one embodiment the marker polypeptide possesses an enzyme activity is quantified and used as a means of detecting the marker in a biological fluid sample.

In embodiments where the marker polypeptide is a naturally occurring peptide, such as a cleavage fragment of a peptide hormone precursor, the background level of the peptide is determined prior to administration of the construct and is simply subtracted from the value determined after infection to provide a measure of marker polypeptide released through expression from the therapeutic virus. In the embodiment where the marker polypeptide is naturally present in the patient and fluctuates with physiological or pathological circumstances, the background rhythm or cycle of the marker is determined to estimate and subtract from values determined post infection. However, in another embodiment, the background level of the marker polypeptide or its fluctuations is suppressed through drugs, modification of the patient's diet, or other suitable measures.

Depending on the degree of accuracy required, the level of expression of the virus can either be inferred from the concentration of marker polypeptide determined in a biological fluid sample or can be determined more accurately by calibration. The level of expression of a virus protein is expressed as the amount of such protein, in moles or mg, synthesized by the cell, tissue, organ, or entire organism which was the target of the viral therapy per unit time. For example, the level of expression can be quantified as the number of nanomoles of a particular viral protein produced per gram of tissue per hour.

In one embodiment, calibration of the marker polypeptide is performed by quantifying both the marker polypeptide and a viral protein product itself (e.g., by extracting the tissue making the viral product and measuring the product directly using HPLC, ELISA, radioimmunoassay, Western blot, or other suitable method) over a sufficient time period to permit extrapolation or determination of the stoichiometry between measured marker polypeptide in a given biological fluid sample and actual tissue level of transgene product. Without calibration, a stoichiometry must be estimated or assumed in order to accurately determine expression of viral product. Even if an assumed stoichiometry is not 100% accurate, it t should allow at least qualitative or semi-quantitative tracking of viral activity.

B. Modifications to Enhance Cytotoxic Efficacy of a *Paramyxovirus*

The invention provides recombinant Paramyxoviridae viruses which have an enhanced ability to kill tumor cells. In one embodiment, a Paramyxoviridae virus is provided which has enhanced fusogenicity. In another embodiment of the invention, a virus is provided which delivers a cytokine to a tumor cell, creating an enhanced immune response against the tumor cell in addition to the direct cytotoxic effect of the virus.

i. Enhanced Fusogenicity

In the course of a natural Paramyxoviridae virus infection, viral spread and virus-mediated tissue damage proceed unchecked until the host immune system terminates the infection. Thus, one of the principles of cancer viral therapy is that there is a window of opportunity from the time of virus inoculation until the establishment of an effective immune response during which the extent of tumor destruction will be dependent on the speed of virus propagation and the intrinsic cytotoxic potential of the virus. Since the cytotoxic properties of Paramyxoviridae viruses reside largely in the ability of their surface glycoproteins to trigger cell-cell fusion and hence syncytium formation, the enhanced potency of induction of cell-cell fusion by a specified Paramyxoviridae virus should create an enhanced therapeutic effect.

The F (fusion) and H (hemagglutinin) proteins of Paramyxoviridae are responsible for triggering cell-cell fusion. In cultured cell lines, co-expression of paired membrane glycoproteins is required for syncytium induction, although some exceptions have been observed, such as SV5, whose F protein alone appears sufficient for syncytium induction. Paramyxoviridae virus F proteins are initially synthesized as polyprotein precursors $F_0$ which cannot be activated to trigger membrane fusion until they have been proteolytically cleaved, usually by a serine protease in the Golgi compartment. The protease cleaves the $F_0$ precursor to yield an extraviral $F_1$ domain and a membrane anchored $F_2$ domain, which remain covalently associated through disulphide linkage. Activation of this processed form of F to trigger membrane fusion is believed to result from binding of the attachment protein (hemagglutinin, H, for measles virus) to the cellular receptor, an interaction which induces conformational changes in H and in turn in F, thus exposing on it a hydrophobic fusion peptide which inserts into the cellular membrane, thereby initiating fusion.

The activity of F and H proteins has been shown to be regulated by the M (matrix) protein which interacts with their cytoplasmic tails. Measles viruses in which the interaction between the M and F&H glycoproteins has been disrupted, either by deletion of M or by the deletion of the cytoplasmic tails of F&H, have been shown to induce more potent cell-cell fusion (Cathomen 1998 EMBO 17 3899, Cathomen 1998 JV 72 1224).

Similarly, truncation of the cytoplasmic domains of a number of retrovirus and herpesvirus glycoproteins has been shown to increase their fusion activity, sometimes with a simultaneous reduction in the efficiency with which they are incorporated into virions (Rein et al., 1994, J. Virol. 68: 1773; Brody et al., 1994 J. Virol. 68: 4620; Mulligan et al., 1992, J. Virol. 66: 3971; Pique et al., 1993, J. Virol. 67: 557, Baghian et al., 1993, J. Virol. 67: 2396; Gage et al., 1993, J. Virol. 67: 2191). Viruses of the Paramyxoviridae family with destabilised matrix/envelope interactions display a marked reduction in their release from infected cells (Cathomen et al., 1998, EMBO J. 17: 3899), presumably reflecting a reduced ability to form orthodox viral particles. This modification thus imparts two distinct advantages for cancer therapy: firstly, increased local spread and hence cell killing, and secondly, reduced release concomitant with reduced systemic viral spread.

Thus, in one embodiment of the invention, Paramyxoviridae variants with modified fusogenicity are generated for use in cancer therapy by modification of any one, two, or all three of the H, F and M proteins; however, it is necessary to co-express H protein with F protein for Paramyxoviridae virus cell fusion activity.

a. Modified H Proteins

The H protein cytoplasmic tail comprises the aminoterminal 34 amino acids of the protein (sequence: $NH_2$-MSPQRDRINAFYKDNPHPKGSRIVINREHLMIDR-COOH) (SEQ ID NO: 12). Modification of H protein by removal of the 24 amino acids immediately follownig the initiator methionine (AA 2–25) results in a loss of fusogenic activity by the virus. In contrast, deletion of either 8 amino acids immediately following the initiator methionine (amino acids 2–9 deleted) or 14 amino acids between amino acids 2 and 17 (amino acids 3–16 deleted) enhance the fusogenic activity of the virus (Cathomen et al., 1998, J. Virol. 72:1224). These results indicate that membrane proximal amino acids 17 to 25 comprise a sequence necessary for fusion activity. The results also indicate that amino acids at least between those numbered 2–16 are involved in negative regulation of fusogenic activity. Therefore, in one embodiment, fusogenicity is enhanced by deletion of either amino acids 2–9, or 3–16. In a further embodiment of the invention, amino acids 2–16 are deleted. In still a further embodiment of the invention, amino acids 2–24 are deleted, and preferably 2–20. In one embodiment of the invention, the virus comprises a truncated H sequence comprising 8–14 fewer amino acids.

In a further embodiment of the invention, any or all of amino acids 2–16 are modified by systematically deleting and/or substituting amino acids and assaying for mutations which increase the fusogenicity of the virus (as measured by determining an increase in the number of cells having greater than 20 nuclei per cell after infection at a given multiplicity of infection with a modified or unmodified virus). In one embodiment of the invention, substitutions are selected which do not disrupt the size, charge, and/or hydrophobic character of the H protein relative to the wild-type sequence.

b. Modified F Proteins

In one embodiment, the F protein is modified by alteration of its cytoplasmic tail, which comprises the carboxyterminal 33 amino acids of the protein (sequence: $NH_2$-RGRCNKKGEQVGMSRPGLKPDLTGTSKSYVRSL-COOH) (SEQ ID NO: 13). Modifications of the F protein found to increase the fusogenic activity of the virus include addition of unrelated sequences to the C-terminus (for example, by alteration of the normal stop codon, or other means), and deletion of 16 or 24 C-terminal amino acids (Cathomen et al., 1998, J. Virol., supra). Viruses incorporating these changes include faster formation of syncytia, with a concomitant enhancement in the rate of cell killing. In another embodiment of the invention, a modified virus is provided which comprises a C-terminal tail comprising at least one deletion and/or substitution and which has enhanced fusogenic activity and/or cell killing effects. The addition or exchange of sequences have also been demonstrated to enhance the fusogenicity of the virus. Therefore, in a further embodiment of the invention, the F protein is modified by the addition of 28 amino acids, while in still a further embodiment, the C-terminal tail of the F protein is exchanged with the C-terminal tail of a Sendai virus.

In another embodiment of the invention, the virus comprises mutations in both the F and H protein. Viruses which have been generated comprising an H protein mutant (animo acids 3–16 deleted) and an F protein comprising either 28 amino acids of extraneous sequence, a deletion of 24 C-terminal amino acids or a replacement of the tail with a cytoplasmic tail derived from Sendai virus all exhibited enhanced fusogenic activity relative to wild-type virus.

c. Modified M Proteins

In another embodiment of the invention, a Paramyxoviridae family virus is provided having an altered or deleted M protein to obtain a virus having enhanced fusogenicity. The alteration of the M protein according to this aspect of the invention may be either wholesale deletion of the protein, or alternatively, one may delete or substitute amino acids necessary for the association of F and H glycoproteins. This may be accomplished by techniques known in the art for systematic site-directed mutagenesis. Clones of Paramyxoviridae virus bearing mutations in the M protein are monitored for enhanced fusogenic activity according to methods known in the art or described herein below.

In order to assess the effect of a modification to the F, H and/or M proteins on the fusogenic activity of the virus, cells are infected in culture and monitored for the formation of syncytia over time relative to syncytia formation occurring with wild-type virus or a reference virus lacking modified F, H and/or M proteins. In another embodiment, mice are infected intracerebrally (see, e.g., Cathomen et al., EMBO J. 17: 3899, 1988) and monitored for viral penetration by in situ hybridization or immunohistochemistry to detect viral RNA or proteins.

d. Assays for Fusogenic Activity

Fusogenicity is said to be increased or enhanced if the number of nuclei/per syncytium is greater by about 10%, preferably by 20%, 35%, 50%, 100%, 200% up to 500% or more than the number of nuclei per syncytium observed at a given time after infection with an unmodified virus of the same strain as the modified virus when the infection is performed at the same multiplicity of infection. Measurement of the number of nuclei in a syncytium or the number of syncytia is most easily accomplished via in vitro (or ex vivo) assays, as described herein.

A culture assay for fusogenic activity may be performed as follows by isolating infectious virus particles by rescue from transfected cells expressing helper functions. One method known in the art for rescuing infectious MV variants from transfected cells expressing helper functions was described by Radecke et al. (1995, EMBO J. 14: 5773, incorporated herein by reference). In this method, recombinant viruses are generated by co-transfecting a recombinant viral (RNA) genome, encoded on a plasmid under the direction of a T7 phage promoter, with a plasmid encoding full length L protein into a human embryonic kidney cell line (293 cells) stably expressing T7 RNA polymerase and MV N and P proteins (the construction of such a helper cell line (293–346) is described in detail by Radecke et al., 1995, supra). Transcription of the plasmid-borne viral genome by T7 polymerase produces viral genomic RNA that is encapsidated by the viral proteins stably (N and P) or transiently (L) expressed in the transfected helper cells. The L protein is expressed transiently, rather than stably since high levels of L expression can impair the rescue of virus; transient expression allows titration of the L protein as needed.

The Paramyxoviridae virus genomic plasmid has the following characteristics. The T7 promoter allows the production of Paramyxoviridae virus antigenomic RNA starting precisely with the first Paramyxoviridae virus nucleotide. The hepatitis delta virus ribozyme follows the Paramyxoviridae virus genomic sequences such that the ribozyme cleaves the RNA at the Paramyxoviridae virus 3' terminus. Following the ribozyme sequence is a T7 polymerase termination sequence to ensure that adjacent vector sequences do not interfere with ribozyme cleavage activity. One important factor for the proper assembly and function of recombinant viruses is that the total number of nucleotides in the genomic replicons should be a multiple of six, to adhere to the so-called "rule of six", originally identified in Sendai virus replication (Calain and Roux, 1993, J. Virol. 67: 4822). The construction of the p(+)Paramyxoviridae virus plasmid is described in detail by Radecke et al. (1995, supra), as is the generation of the P, N and L plasmids that supply the helper functions.

For the rescue of recombinant viruses, 293-3-6 cells are transfected in 35 mm dishes with 8 ug of a plasmid encoding a modified Paramyxoviridae virus genome (derived, for example, from the Paramyxoviridae virus genomic plasmid p(+)Paramyxoviridae virus) in the presence of 5 ng of plasmid encoding the Paramyxoviridae virus L polymerase (for example, pEMC-La; Radecke et al., 1995, supra). Two days after transfection, cells are expanded from 35 mm to 90 mm dishes and cultured another two days before scraping and adsorption to Vero cell monolayers. Infected Vero cells are monitored for syncytia formation, and syncytia are picked and propagated further on Vero cell cultures. Virus is harvested from Vero cell syncytia by scraping cells from the dishes and subjecting them to two rounds of freeze/thaw. The cleared supernatants represent "plaque purified" virus. Viral stocks are produced by infection of Vero cell monolayers (adsorption for 1.5 hours at 37° C.), followed by scraping of infected cells into the medium and freeze/thaw lysis. Viral stocks are aliquotted, frozen and stored at −80° C.

In another embodiment, a second, novel method of rescuing infectious viral variants is provided. In this embodiment, susceptible cells are infected and monitored for the formation of syncytia. Modified viruses isolated as in step (a) above are assayed for enhanced fusogenicity by infection of cultured African green monkey kidney (Vero) cells, which grow on Dulbecco's Modified Eagle's Medium (DMEM) supplemented with 5% fetal calf serum (FCS). Recombinant viral titers are assayed for by infecting Vero cells in 35 mm culture dishes. After 2–3 hours of viral adsorption, the inoculum is removed and cells are overlaid with 2 ml DMEM containing 5% FCS and 1% SeaPlaque agarose. After 3 to 5 days, cultures are fixed with 1 ml of 10% trifluoroacetic acid for 1 hour, then UV cross-linked for 30 minutes. After removal of the agarose overlay, cell monolayers are stained with crystal violet and plaques are counted to determine viral titer.

In one embodiment, enhanced fusogenicity of recombinant viruses is assayed for by infection of separate cultures of Vero cells with either the recombinant or the wild-type virus (or any modified viral reference strain used as the starting point in generating a particular recombinant) at the same multiplicity of infection (MOI). Cell fusion activity of the virus is evaluated by monitoring the number and size of syncytia (number of nuclei per syncytium) over time. Similarly, cytotoxic activity of the viruses can be monitored by following the death of cells over time. A particular recombinant is said to exhibit enhanced fusogenicity according to the invention if the engineered virus yields greater than about 125%, preferably 135%, 150%, 200%, or up to as high as 500% or more of the number of nuclei per syncytium observed with wild-type or reference virus at a given time after infection relative to that observed with the appropriate control virus. Similarly, the cytotoxicity of a particular recombinant or engineered virus is said to be enhanced if the rate of cell death is about 125%, preferably 135%, 150%, 200%, or up to as high as 500% or more of the rate observed with wild-type or reference virus at a given time after infection relative to that observed with the appropriate control virus.

ii. Viral Expression of Immunomodulatory Proteins.

In another embodiment of the invention, host antitumor activity is stimulated by providing a virus capable of expresssing an immunostimulatory virus (e.g., a cytokine). Because it has been demonstrated that exogenous genes may be introduced to the Paramyxoviridae virus genome (e.g., by insertion between viral protein coding sequences or by expression as protease-cleavable fusion proteins, as described above), Paramyxoviridae virus variants expressing exogenous proteins that potentiate the killing of tumor cells are useful to enhance the efficacy of anti-tumor activity. Proteins able to potentiate the killing of tumor cells include those cytokines or other immunostimulatory proteins that stimulate a cell-mediated anti-tumor immune response by recruiting immune cells to the site of cytokine production.

Cytokines or immunostimulatory proteins useful according to this aspect of the invention include, but are not limited to, the following (the number following each cytokine is the GenBank Accession No. for the sequence encoding the cytokine): IL-1, M28983; IL-2, S77834; IL-3, M14743; IL4, M13982; IL-5, J03478; IL-6, M54894; IL-7, J04156; IL-12, AF101062; IFN-γ, U10360; and TNF-, M16441 and any other protein that stimulates the immune response (e.g., a costimulatory molecule).

The expression of immunomodulatory protein by a modified Paramyxoviridae virus according to the invention may be assessed in infected cell cultures by means known in the art for assaying the presence of the particular protein. For example, expression of immunomodulatory protein may be evaluated by Western (immunoblot) analysis using antibodies recognizing the specific protein. Other immunoassays, such as ELISAs may be used, or, alternatively, cell-based assays for the activity of the protein may be used as known in the art.

An enhanced immune response is assessed by assays for, e.g., antibody production, lymphocyte proliferation, cell-mediated cytotoxicity, or cytokine production which is significantly higher in an organism treated with the modified virus when compared to an organism treated with the unmodified virus (to within 95% confidence levels) and/or has aa reduced incidence of tumor formation (e.g., from 100% to 10%) in a mammal receiving the modified virus.

C. Modifications that Enhance the Selectivity of Viral Infection

Improvements in the selectivity of Paramyxoviridae virus infection enhance its usefulness as a vector for oncolytic therapy since such improvements minimize damage to surrounding, non-tumor tissue. In one embodiment, to prevent collateral damage to normal host tissues, modifications that serve to limit virus spread and viral cytotoxicity to the microenvironment of the neoplastic cells may be introduced to the Paramyxoviridae virus genome. In one embodiment, the infective activity of the virus is made dependent upon an activity, such as a protease, associated with the tumor microenvironment. In a second embodiment, the virus is targeted to a tumor-specific protein.

1. Restricting Paramyxoviridae Viral Infectivity by Making it Dependent on Activities Associated with the Tumor Microenvironment The F glycoprotein of Paramyxoviridae viruses is critical for triggering of both virus-cell and cell-cell fusion. As discussed above, the protein is synthesized as a precursor, $F_0$, which is proteolytically cleaved into $F_1$ and $F_2$ components by a ubiquitous Golgi compartment protease (furin). This cleavage is necessary for activation of the fusion function of the protein, and hence for the infectivity of the virus.

In one embodiment, the infectivity of the virus is restricted largely to tumor cells by making its proteolytic activation dependent on a tumor-associated protease. Proteases such as matrix-metalloproteinases (MMPs), plasminogen activator/plasmin system, p65, cathepsins, trypsin-like proteases, human kallikrein 2 and prostate specific antigen are intimately involved in cancer invasion and metastasis and in complement resistance, and tumors therefore provide a protease-rich microenvironment.

The invention thus contemplates the introduction of selected cancer-associated protease cleavage sites into viruses. The cleavage of the $F_0$ precursor may be made dependent on a protease other than furin by replacement of the furin cleavage signal R-R-H-K-R (SEQ ID NO:14) at amino acids 108 to 112 of the measles virus (MV) or the corresponding residues of the other Paramyxoviridae viruses with that of another protease. Cleavage by furin occurs after arginine 112. Correct cleavage at this site is essential, because changing arginine 112 to leucine has been shown to result in aberrant cleavage and loss of fusion ability (Alkathib et al., 1994, J. Virol. 68:6770).

Proteases with sites useful for restricting the infectivity of a therapeutic virus according to the invention include, but are not limited to those listed in Table 1. The cloning of the Paramyxoviridae virus F protein into an expression vector, pCG, under control of the CMV early promoter to generate the plasmid pCG-F was described by Cathomen et al. (1995, Virology 214: 628). Site-directed mutagenesis to convert the furin cleavage site to a site for another protease may be accomplished by one of skill in the art using any of a number of site-directed mutagenesis methods known in the art. One example of a site-directed mutagenesis approach is that embodied by the QuikChange Site-Directed Mutagenesis Kit (Stratagene, La Jolla, USA), which uses two complementary mutagenic primers and a double-stranded plasmid template.

Paramyxoviridae viruses modified to restrict infectivity by changing the $F_0$ protease cleavage site may be assessed for restricted infectivity by infecting cultured cells in the presence and absence of the protease, if it is an extracellular protease. For an intracellular protease associated with a given tumor cell type, cells either expressing or not expressing the protease are infected with recombinant virus. In one embodiment, the infectivity of the virus is considered to be modified if the virus infects (i.e., causes the formation of syncytia or plaques, monitored as described for viral titer assays) cells either in the presence of or expressing the specific protease more efficiently than it infects cells either not expressing or in the absence of the specific protease. As used in this context, "more efficiently" or "to a greater degree" refers to a number of syncytia or plaques formed in a given amount of time that is at least 1.25-fold, and preferably 10-fold, 100-fold, 1000-fold or greater in the cells expressing or cultured in the presence of the protease, relative to cells not expressing or not cultured in the presence of the protease.

Another means of evaluating modified viruses for restriction of host specificity is to perform infections of cultured cells expressing the protease activity used to re-target the specificity in the presence and absence of inhibitor(s) of the targeting protease. A recombinant virus that only infects or that infects to a greater degree in the absence of the inhibitor may be said to be restricted in its host specificity according to the invention. The most efficiently that a virus may be targeted is the situation where it is completely dependent upon the presence of the targeting protease for infection and does not infect at all in the absence of the protease.

The invention also contemplates generating Paramyxoviridae viruses expressing F proteins activatable by cancer-specific proteases through the production of a randomized cleavage signal library and selection of functional protease-activatable viruses bearing F protein mutations in a variety of tumor cells. In order to generate a randomized cleavage library, PCR primers (an F primer and a random sequence primer) are used to amplify an $F_0$ plasmid template.

The F primer should have sequences complementary to the $F_0$ template sequence 3' of the nucleotides encoding the furin cleavage sequence (i.e., complementary to $F_1$ sequence adjacent to the cleavage site), preceded by (i.e., 3' of) a randomized stretch of 12 bases corresponding in position to those encoding the furin cleavage site RHKR (SEQ ID NO: 15). In order to avoid restoring furin cleavage, the "randomized" stretch of nucleotides should not be truly random, but rather be designed such that positions 1, 2 and 3 cannot be lysine or arginine (see Example 5).

The "random" sequence primer and the downstream sequence PCR primer should also incorporate restriction sites allowing the sub-cloning of the fragments generated into a retroviral transfer vector. Following amplification using the $F_0$ template, the library of PCR products is digested with the appropriate enzyme(s) and cloned into the retroviral transfer vector (for example pMFGnlsLacZ, wherein the nlsLacZ sequences are removed by BamHI digestion) to generate a library of F protein cleavage site retroviral expression constructs. The library is transfected into a panel of tumor cell lines. By co-transfection of an H expressing plasmid, such as pCG-H (Cathomen et al., 1998, J. Virol., supra), cells in which F is properly cleaved to expose the amino-terminal amino acids of $F_1$ are identified by their ability to form syncytia, which can then be picked to isolate the particular cleavage site mutant activatable by a protease expressed by that tumor cell line.

In one embodiment, the paramyxoviral library is used to infect a panel of human cell lines which are subsequently observed for the formation of multinucleated syncytia, expected to be maximal 24 to 72 hours after infection of the cells. The cell lines are grown to near-confluency before infection. Examples of cell lines that can be used for this assay, include but are not limited to, A431 (epidermoid carcinoma), HT1080 (fibrosarcoma), EJ (bladder carcinoma), C175 (colon carcinoma), MCF7 (breast carcinoma), HeLa (cervical carcinoma), K422 (follicular lymphoma), U266 (myeloma).

DNA is extracted from each syncytium formed in a tumor cell line, followed by PCR amplification of the F sequence and sequencing to identify the cleavage signal sequence. Further selective pressure may be applied to the system by transfecting the cells in the presence of particular protease inhibitors. By the nature of their selection process, clones isolated from the cleavage library will be known to have modified selectivity of host cell type.

2. Restricting Paramyxoviral Infectivity by Targeting to a Specific Cell-Surface Protein.

An alternative strategy to limit collateral damage to normal tissues is to engineer the binding specificity of the Paramyxoviridae virus membrane glycoproteins to restrict the specificity of virus-cell and cell-cell fusion. In such a case, virus propagation and virus-mediated cytotoxicity will be confined to neoplastic tissues expressing the targeted cell surface marker. Any tumor-specific cell-surface protein is useful according to this targeting method, although it is preferred that the protein not be sequestered from potentially binding ligands. It has been demonstrated that polypeptide binding domains can be displayed on the surface of Paramyxoviridae viruses or Paramyxoviridae virus-infected cells as C terminal extensions of the H glycoprotein.

In one embodiment the displayed ligand positively retargets the virus to cancerous cells via the specific targeted cell surface marker, mediating both viral attachment and entry. Paramyxoviridae family viruses are modified using bispecific antibodies which prevent attachment to the viral receptor and instead confer new binding specificities, resulting in target cell transduction. Successful attachment and infection has been demonstrated for adenoviruses targeted to EGF (Watkins et al., 1997, Gene Ther. 4: 1004), folate receptor (Douglas et al., 1996 Nature Biotech. 14: 1574), and FGF-2 (Goldman et al., 1997, Cancer Res. 57: 1447).

Alternatively, the invention contemplates Paramyxoviridae viruses engineered such that targeted attachment of the virus to the cell does not lead to gene delivery, unless protease cleavage occurs.

For Paramyxoviridae viruses, the choice of targeted receptor plays a role in determining the success of gene transfer. A receptor which sequesters the virus away from the cell surface will not permit fusion, precluding gene delivery. Attempts to extend the host range of ecotropic MLV through the display of polypeptides such as stem cell factor (SCF, Yajima et al., 1998, Hum. Gene Ther. 9: 779, Fielding et al., 1998, Blood 91: 1802), human MHC-I (Marin et al., 1996, J. Virol. 70: 2957), erythropoetin (Kasahara et al., 1994, Science 266: 1373), EGF (Cossett et al., 1995, J. Virol. 69: 6314), anti-CD3 antibody (Ager et al., 1996, Hum. Gene Ther. 7: 2157), anti-colon carcinoma antibody (Ager et al., 1996, Hum. Gene Ther. 7: 2157) and anti-human LDLR single chain antibody (Somia et al., 1995, Proc. Natl. Acad. Sci. USA 92: 7570) on or as part of the envelope glycoprotein have resulted in recombinant viruses which can bind the targeted receptors but which give very low levels of transduction in the target cells. For Paramyxoviridae viruses, direct entry at the cell surface occurs, and this is believed to be triggered by receptor binding which induces conformational changes in the envelope glycoproteins such that a hydrophobic domain on the fusion protein is exposed.

The present invention circumvents this limitation, through the use of protease activatable viruses. In one embodiment, a (preferably tumor-specific) protease cleavage site is placed between the envelope glycoprotein and the displayed ligand, such that subsequent to targeted attachment, cleavage of the displayed ligand fully exposes the envelope glycoprotein and allows virus-cell membrane fusion to proceed. In this strategy, the degree of selectivity may be enhanced by the dependence on two tumor-specific targets: the cell surface ligand and the protease (see Table I for a non-limiting list of proteases useful for targeting).

In one embodiment, ligands that bind tumor-specific cell surface proteins are expressed as cleavable fusions with Paramyxoviridae virus H proteins using the same approach as used to generate Paramyxoviridae virus H protein tagged with a marker peptide described above (also see Example 1). For example, an SfiI site in the MV H protein or another restriction site in about the same region of the gene can be engineered by means well known in the art to create a site for introduction of the sequence of a cleavable ligand. One of skill in the art may modify the SfiI site as necessary to accommodate a given ligand coding sequence. Any ligand known to bind a tumor specific antigen may be fused to H protein and displayed on the surface of the modified virus. In one embodiment, the ligand is fused to H protein by a linker that is sensitive to a tumor-associated protease. Ligands for tumor cell-specific surface proteins include, but are not limited to, single-chain antibodies that recognize a given tumor antigen. Sequences encoding a single chain antibody can be introduced as fusions with the H protein in the same manner as sequences for other ligands.

In one embodiment, the effect of the display of a targeting ligand as an H fusion on the selectivity of a modified Paramyxoviridae virus is assessed by infection of cells either expressing or not expressing the tumor-specific protein bound by the ligand. A modified virus is said to have increased specificity or selectivity if it infects cells expressing the specifically targeted tumor protein more efficiently than it infects cells lacking the specifically targeted tumor protein. The most specific a targeted infection may be is when the virus is completely dependent on the presence of the tumor-specific protein on the cell surface for infection.

D. Modifications of Paramyxoviridae Viruses that Reduce Transmissibility of the Virus for Oncolytic Viral Therapy For safety reasons, it is desirable that an engineered Paramyxoviridae virus used for oncolytic viral therapy should not be transmitted from the treated patient to care givers, relatives or sexual partners. To this end, engineered vaccine strains of Paramyxoviridae viruses which are known to have low transmissibility compared to their more highly pathogenic counterparts are suitable for use according to the invention. In addition, the previously described Paramyxoviridae virus modifications that disrupt the interaction between M and F and H and enhance the potency of cell-cell and virus cell fusion, are associated with a reduction in the efficiency with which virus is released from infected cells. Hence, modifications of this kind appear to enhance local spread of virus between neighboring cells while simultaneously reducing the risk of systemic spread and transmissibility between hosts. Naturally existing strains of virus which have low transmissibility are also encompassed within the scope of the invention, and encompass the Edmonston strain and the Moraten strain of measles virus.

E. Production of Genetically Altered Paramyxoviridae Viruses

A convenient and reliable method for the generation of Paramyxoviridae virus recombinants for oncolytic viral therapy is disclosed to introduce any, some, or all of the modifications described above. In this improved method, the desired modifications (e.g., those providing marker expression, enhanced syncytium formation, enhanced cell-mediated immunostimulation, enhanced selectivity of infection and/or reduced transmissibility) are engineered into a plasmid comprising an infectious molecular clone of the Paramyxoviridae virus genome sequence. Expression of the antigenomic viral RNA is under the direction of the T7 RNA polymerase promoter. A helper virus is then used to provide all of the complementing functions required to rescue the infectious clone into viable Paramyxoviridae virus particles. Elimination of the helper virus genome is facilitated by its unique characteristics. Namely, that the helper virus may be deleted for, or expresses no F protein capable of cooperating with H protein to promote virus-cell or cell-cell fusion. Alternatively, the helper virus may carry a trypsin activatable F glycoprotein or it may carry sequences encoding a tag, such as GFP, for identification. Repeated passage of recombinant virus in the appropriate selection system, i.e in the absence of trypsin or by selecting non-fluorescing syncytia, respectively, results in the isolation of virions containing only the rescued genome with no contamination from helper virus genomes.

Helper viruses necessary for this approach provide N, P and L proteins for the replication and encapsidation of the modified virus into infectious particles. The helper virus must also be either deleted in F (and thus previously produced on F expressing cells), express a trypsin-activatable F (as described herein), or encode GFP (green fluorescent protein) expression. Following transfection of the modified genomic Paramyxoviridae virus plasmid into cells expressing T7 polymerase (e.g., 293 cells stably transfected with a T7 polymerase encoding plasmid; construction of a T7-Neo plasmid, pSC6-T7-NEO is described by Radecke et al., 1995, supra), cells are infected with the helper virus. N and P proteins coat the antigenomic, T7-transcribed RNA, which is then replicated by the viral polymerase L to produce a genomic RNA which is the template for subsequent mRNA transcription and production of viral proteins. The plasmid encoding the antigenomic RNA must also encode a ribozyme, such as the hepatitis delta ribozyme, situated at the end of the transcript such that the proper ends of the virus are generated.

Helper virus encoding a GFP tag is constructed as follows. The Plasmid pMeGFPNV includes the antigenome of MV with an insertion containing the open reading frame of enhanced green fluorescent protein (eGFP) flanked by the 3' and 5' untranslated regions of the N gene. The cloning strategies used in the generation of pMeGFPNV are as follows.

Figure 2:
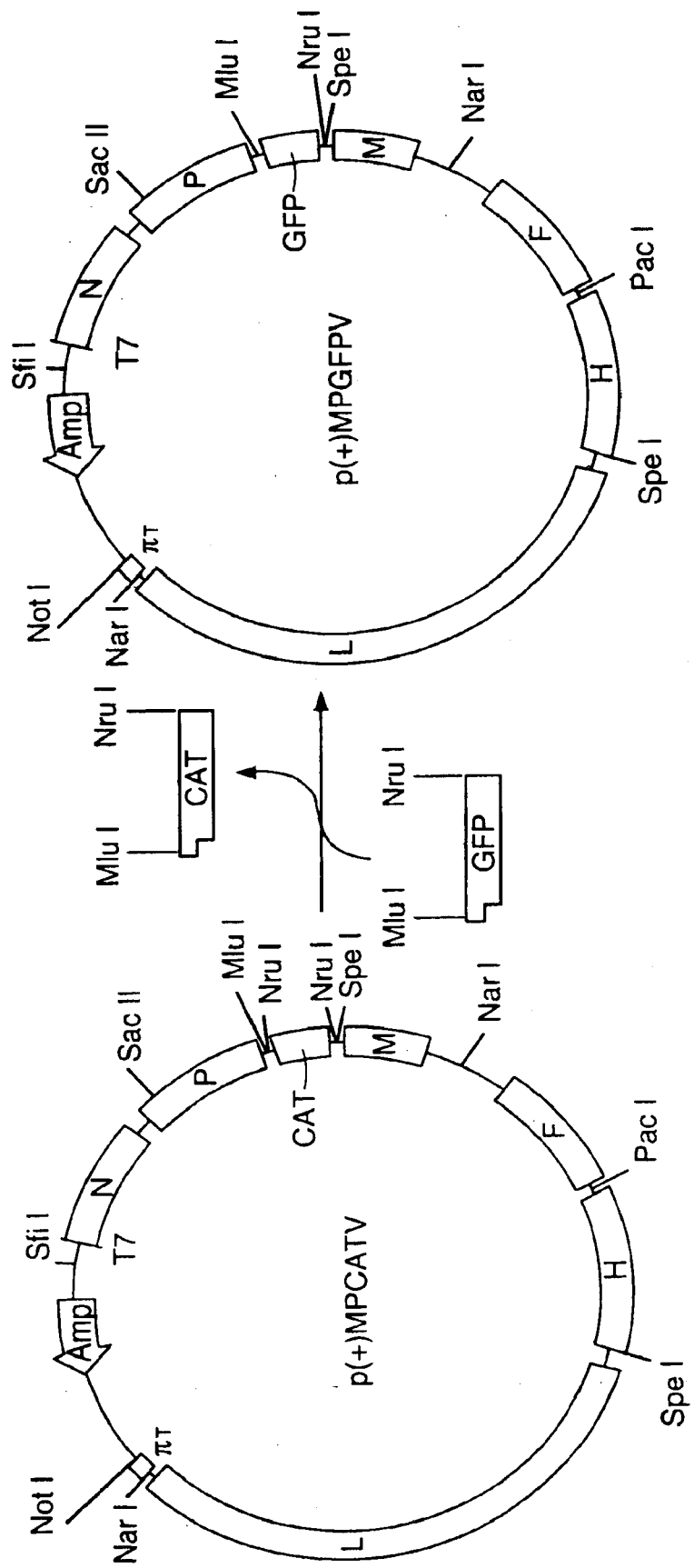

1. P(+)MPCATV#32 (see FIG. 2) is cleaved with Nru 1 in a one fold digestion. After sodium acetate/EtOH precipitation, the linearized plasmid is digested with Mlu 1 and dephosphorylated. The plasmid backbone is then separated form the excised CAT insert by agarose electrophoresis. pBLoT(+)GFP14 is digested in the same way as p(+)MPCATV#32. The excised GFP fragment was then isolated by agarose gel electrophoresis and ligated with the backbone of p(+)MPCATV#32. Positive clones are identified by Hpa 1 digestion of miniprep DNA and growth to obtain maxiprep DNA. Correct insertion of the GFP fragment is then confirmed by restriction analysis and sequencing. The resulting plasmid is designated as p(+)MPGFPV11.

Figure 3:
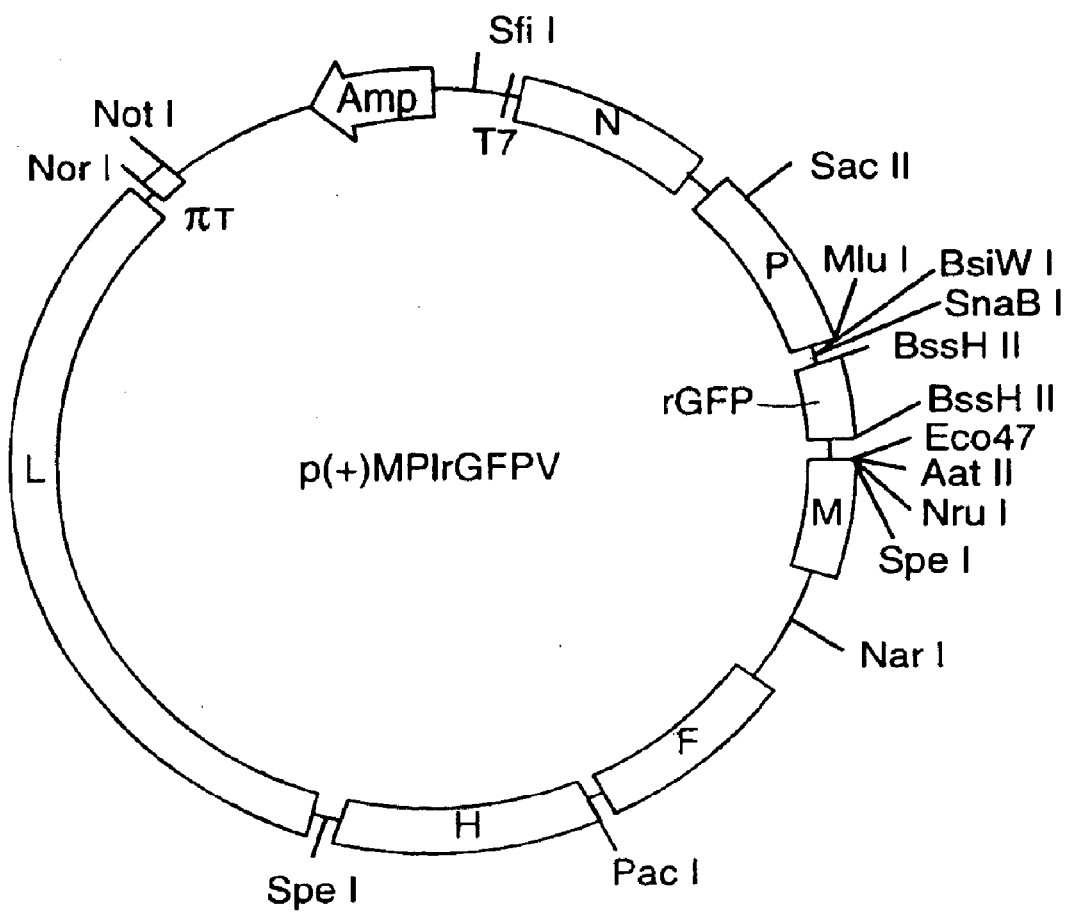

2. The plasmid p(+)MPGFPV11 is digested with Nru 1, precipitated and cleaved with Mlu 1. After dephosphorylation of the 5' ends, the backbone DNA is isolated by extraction from an agarose gel. The IrGFP cassette is excised from the plasmid pBLoT(+)IrGFP6 by digestion with Mlu 1 and EcoR V. After isolation from an agarose gel, it isligated to the previously digested p(+)MPGFPV11 backbone. The minipreps of this ligation are then screened by digestion with HpaI, and two clones, designed as p(+)MPIrGFPV1 and 7 (FIG. 3) are grown for DNA maxipreparation. Sequencing over the cloning sites is done to confirm the results obtained by the analytical digestions.

The Sfi 1×Sac II cassettes of the plasmids p(+)MV-2A#12 (by F. Radecke) and p(+) MpIrGFPV7 (see above) are exchanged for the same fragment excised from p(+) MIrGFPNP 3. For this purpose, all three plasmids are completely digested with both enzymes. In addition, the 5' ends of the full-length plasmids are desphosphorylated before all fragments of interest are purified by agarose gel electrophoresis. After ligation and transformation, minipreps are grown and screened for positives by digestion with Hpa 1.

Figure 4:
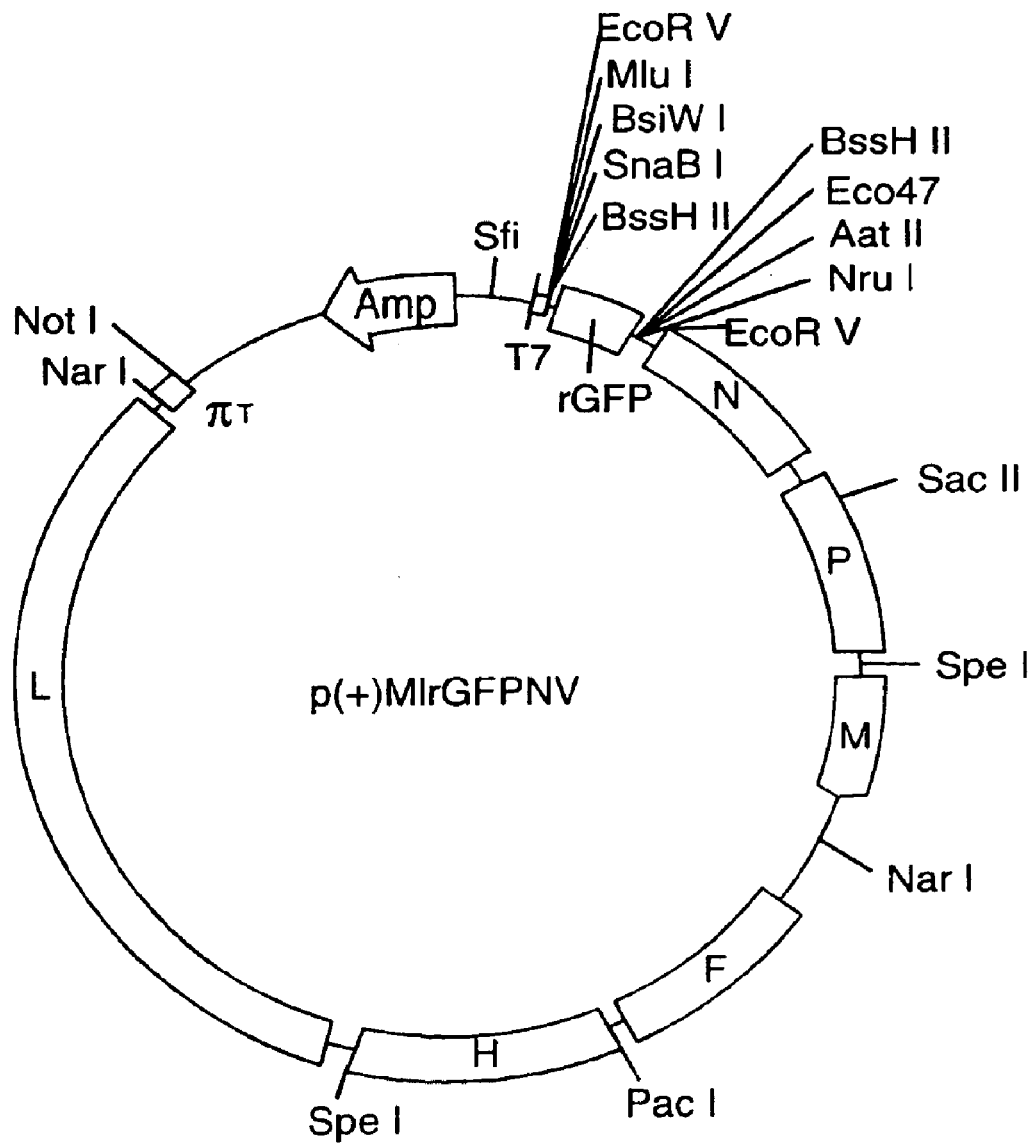

Depending on the backbone used, the newly generated plasmids carry one or two additional transcription units (ATUs) designed as p(+)MlrGFPNV14 and 23 (NATU in front of the N gene) and p(+)M2xlrGFPV 38 and 45 (N- and P-ATU), respectively (FIG. 4).

The additional transcription unit (ATU) encoding GFP is comprised of 852 nucleotides, and pMeGFPNV conforms to the rule of six. The insertion was made into the full length infectious clone of measles virus, p(+)MV (EMBL Accession No. Z66517) between the 3' end and the gene encoding the nucleocapsid protein. Recombinant virus is recovered from this plasmid using the 293-3-46 rescue cell line (Radecke et al., 1995, supra). The cell line is transfected with pMeGFPNV (5 ug) and pEMCLa (10 ng), which expresses the MV polymerase protein under the control of the T7 promoter, using a calcium phosphate transfection procedure. Cell monolayers are monitored microscopically for the appearance of syncytia each day. Autofluorescence with these syncytia, indicating eGFP expression, is verified using an inverted UV microscope (Leica). Virus stocks are produced following plaque-purification and titers of approximately $5 \times 10^5$ TCID$_5$/ml are obtained.

Viruses produced from the 293-T7 cells are heterogeneous, containing either rescued or helper virus genomes, or both. To separate rescued virus from helper in the case of the trypsin-activatable helper virus, the virus is serially passaged in the absence of trypsin. After about 10 sequential passages in the absence of trypsin, virus will generally be free of helper.

In order to separate rescued virus from helper in the case of the F deleted helper virus, transfected 293-T7 cells are overlaid onto Vero cell monolayers, syncytia are picked and the process repeated for several rounds of infection.

In order to separate rescued virus from helper in the case of the GFP-tagged helper virus, transfected 293-T7 cells are overlaid onto Vero monolayers and syncytia that do not fluoresce are picked and re-passaged on fresh cells. Repeated passage of non-GFP-expressing viruses selects for those viruses that contain only the rescued genome.

Following selection for viruses not carrying helper viral sequences, stocks of modified Paramyxoviridae virus are generated by infection of Vero cells, followed by scraping in medium, freeze/thaw, and frozen storage as elsewhere herein.

F. Dosage, Administration, and Pharmaceutical Formulation

For in vivo treatments, a recombinant Paramyxoviridae virus according to the invention is administered to the patient, preferably in a biologically compatible solution or a pharmaceutically acceptable delivery vehicle, by ingestion, injection, inhalation or any number of other methods. The dosages administered will vary from patient to patient; a "therapeutically effective dose" will be determined by the level of enhancement of function of the transferred genetic material balanced against any risk or deleterious side effects. Monitoring levels of gene introduction, gene expression and/or the presence or levels of the encoded product are used selecting and optimize the dosages administered. In one embodiment, a composition including a recombinant virus will be administered in a single dose in the range of $10^{3-10^{12}}$ pfus.

Ex vivo treatment is also contemplated within the present invention. Thus, in addition to direct administration of virus to patients or to their tumors, in one embodiment, therapeutic virus is administered by introducing virus-infected cells (preferably, but not necessarily taken from the same patient or tumor) to the patient or their tumor by the same routes of administration described for virus alone. Cell populations, for example, tumor cells, can be removed from the patient or otherwise provided, infected with a recombinant Paramyxoviridae virus according to the invention, then reintroduced into the patient. The infection conditions ex vivo are identical to virus infection conditions disclosed herein; the number of cells infected ex vivo which are reintroduced into the patient are about $10^4$ to $10^{10}$ cells per day over a time course of about 1 minute to 6 hours.

In one embodiment, the course of therapy is monitored by evaluating changes in clinical symptoms (known in the art for each particular type of tumor) or by direct monitoring of tumor size. Oncolytic viral therapy using modified Paramyxoviridae viruses is effective if tumor size and/or clinical symptoms are reduced following administration of virus. A reduction in tumor size of at least 10% within a given time period, such as one to four weeks, is desirable, and higher levels of reduction, for example, 25%, 50% 75% and even 100% are even more desirable. In one embodiment, in the case of a therapeutic virus modified to express a marker, the level of viral expression, and therefore the degree of viral activity, is monitored by assays of appropriate body fluids. Alternatively, a tissue biopsy is performed in order to observe syncytium formation via direct visualization. A composition according to the invention also is determined to be useful according to treatment methods of the invention where syncytium formation is observed to the extent that multinucleate areas of cytoplasm are observed in a tissue biopsy during the course of treatment.

In another embodiment of the invention, dosing is repeated. Repeat dosing is indicated in cases in which observations of clinical symptoms or tumor size or monitoring assays indicate either that the tumor has stopped shrinking or that the degree of viral activity is declining while the tumor is still present. Repeat doses (using the same, or further modified virus) may be administered by the same route as initially used or by another route.

Suitable pharmaceutical formulations, in part, depend upon the use or the route of entry, for example oral, transdermal, or by injection. Such forms should not prevent the composition or formulation to reach a target cell (i.e., a cell to which the virus is desired to be delivered to). For example, pharmacological compositions injected into the blood stream should be soluble. Other factors are known in the art, and include considerations such as toxicity and forms which prevent the composition or formulation from exerting its effect.

EXAMPLE 1

Paramyxoviridae Virus Expressing a Marker Polypeptide

Two different MV cDNA clones were generated that express C-peptide linked to MV H protein via either a furin-cleavable or a non-furin-cleavable linker sequence. Initially, C-peptide linked to the cleavable and non-cleavable linkers were cloned into a pCG vector as a C-terminal extension of H protein to generate vectors pCGHFurCP and pCGHG4SCP, respectively (See FIG. 1 for a schematic diagram).

To produce pCGHFurCP, primers Fur CP1.Nf and SfurinCP were used in a PCR reaction with pro-insulin template (ATCC) for 18 cycles at 94° C. 1 min, 55° C. 1 min and 72° C. for 1 min. The resulting PCR fragment, tagged with Sfi-CP-Not was gel purified and digested with ScfiI and NotI restriction enzymes. The pCGH backbond pCGH EGFr-was also digested with SfiI and NotI, and ligated with the prepared insert. Ligation reactions were transformed into competent *E. Coli*, and resulting colonies screened by PCR for the presence of C-peptide insert. Successful transformants were grown to large scale and the DNA isolated.

```
FurCP1.Nf
ttt tcc ttt tgc ggc cgc ttt cat caa cgc ttc tgc agg gac ccc tc      (SEQ ID NO:16)
SFurinCP
```

-continued

```
gtc cat gcg gcc cag ccg gcc CGA TTA AAG AGA gag gca gag gac ctg cag gtg gg    (SEQ ID NO:17)
V  H   A A Q P   R   L   K   R   E   A   E   D   L   Q   V                    (SEQ ID NO:18)
```

To produce pCGHG4SCP, primers G4SCP1.Nf and SG4SCP.b were used in a PCR reaction as described above.

```
G4SCP1.Nf
ttt tcc ttt tgc ggc cgc ttt cat cat caa cgc ttc tgc agg gac ccc tc            (SEQ ID NO:19)
SG4SCP.b
gtc cat gcg gcc cag ccg gcc GGT GGA GGC GGT TCA gag gca gag gac ctg cag gtg gg (SEQ ID NO:20)
V  H   A A Q P   G G G G S   E   A   E   D   L   Q   V                        (SEQ ID NO:21)
```

The DNA fragments encoding H-linker-CP were digested from the pCG constructs using enzymes PacI and SpeI, and transferred into the MV cDNA clone p(+)MV-Nse by ligation with PacI/SpeI digested DNA. The resulting full length cDNA constructs encoding H linked to C-peptide via a furin cleavable or non-cleavable sequence were named p(+)MV-HFurCP and p(+)MV-HG4SCP, respectively.

To recover replicating chimeric measles viruses, 5 µg of each construct was transfected into 293–346 cells with 5 ng pEMCL (expressing the MV polymerase, L) using calcium phosphate. Following transfection, the cells were overlaid onto Vero cells which were observed for the formation of syncytium. Syncytia were picked and transferred to fresh cells to expand the virus stock, which was then prepared by freeze/thaw and titered using a conventional TCID50 assay.

To check whether the viruses produce C-peptide, T75 tissue culture flasks with confluent monolayers of Vero cells were infected with 105 pfi of virus for 2 h at 37° C. The media was replaced with 5 ml of 5% FCS-DMEM for 16 h and then harvested for C-peptide assay. Results are tabulated below, and show that the CP expressed by the furin sensitive linker is secreted into the extracellular media.

| MV Clone   | C-Peptide in Medium |
|------------|---------------------|
| MV-NSe     | <33 pM C-peptide    |
| MV-H/FurCP | 7000 pM             |
| MV-H/G4SCP | 74 pM               |

EXAMPLE 2

Paramyxoviridae Viruses with Enhanced Fusogenicity

Fusogenicity of Paramyxoviridae viruses may be enhanced by modification of the F, H or M proteins.

A. Modification of Fusogenicity by Modification of Measles Virus F Protein

F protein cytoplasmic tail mutations have been introduced to plasmids encoding full length measles virus genomic RNA (e.g., p(+)MV, Radecke et al., supra) as follows. Plasmids peFHLP, peFHLF and peFHLI (described in Schmid et al., 1992, Virology 188: 910) and plasmid peF (cSeV)HL were used as starting material for generation of full length measles virus plasmids encoding the following F mutants, respectively: mutant Fc+28, resulting from a stop codon mutation, comprises 28 amino acids of extraneous sequence appended to the C-terminus of the wild-type F protein (Fc+28 also has an additional Glu relative to the Edmonston B strain of the virus at position 27 relative to the transmembrane domain); mutant FcΔ16 lacks the 16 C-terminal amino acids of the F cytoplasmic tail (remaining sequence of the cytoplasmic tail is RGRCNKKGEQaGM-SRPG (SEQ ID NO:22), where the lower case "a" also differs from the sequence of the Edmonston B strain of measles virus); mutant FcΔ24 lacks 24 C-terminal amino acids relative to the wild-type virus (remaining sequence of the cytoplasmic tail is RGRCNKKGE (SEQ ID NO:23)); and mutant FcSeV has the measles virus F protein cytoplasmic tail replaced by the F cytoplasmic tail from Sendai virus. Plasmid pcF (cSeV)HL was generated by subcloning a PstI-PacI PCR fragment encoding the SeV F cytoplasmic tail into peFHL. PCR was performed with pGem4-SVG$_0$ (described in Vidal et al., 1989, J. Virol. 63: 892) as the template and primers 5'-AAAACTGCAGACTCAAAGGTCAATGC-3' (SEQ ID NO:24) and 5'-CCCTTAATTAATATACAGATCTCAACGGAT-3' (SEQ ID NO:25).

The genomic measles virus plasmids comprising the F cytoplasmic tail mutations were generated by three-way ligations of a NarI-PacI fragment carrying the mutated F gene coding region from plasmid peFHLP, peFHLF, peFHLI or peF(cSeV)HL, respectively, with a PacI-SacII fragment and a SacII-NarI fragment of p(+)MV. All full length plasmids coding for mutated antigenomic RNA conform to the rule of six.

Infectious viruses comprising the F protein mutations were rescued from transfected cells according to the method of Radecke et al. (1995, supra) and used to infect Vero cells at an MOI of 3. Cytopathic effects, including syncytia formation, were monitored over time by microscopic examination. All F mutant viruses tried produced syncytia. Viruses encoding the F mutants Fc+28, and FcΔ24 produced syncytia that grew faster than those induced by infection with wild-type virus.

B. Modification of Fusogenicity by Modification of Measles Virus H Protein

H protein mutant plasmids peHcΔ8 (lacking amino-terminal amino acids 2–9), peHcΔ14 (lacking amino terminal acids 3–16), and peHcΔ24 (lacking amino-terminal amino acids 2–25) were constructed by subcloning a ClaI-EcoRI PCR fragment into peH5. peH5 is a shuttle vector for subcloning into the full-length p(+)MV (Cathomen et al., J. Virol., supra). peH5 contains a single ClaI site in the 5' untranslated region of the H protein and a single EcoRI site at the border between the transmembrane domain and the ectodomain, both sites introduced by silent mutations. PCR was performed with peH5 DNA as template and forward primers 5'-CCATCGATAATGGCCTTCTACAAAGATAACC-3' (peHcΔ8) (SEQ ID NO:26), 5-CCATCGATAATGAGCCATCCCAAGGGAAGTAGG-3' (peHcΔ14) (SEQ ID NO:27), and 5'-CCATCGATAATGAACAGAGAACATCTTATGATT-3' (peHcΔ24) (SEQ ID NO:28). The reverse primer annealed downstream of the H protein coding region in the plasmid.

To construct the H mutant in which the measles virus cytoplasmic tail was replaced with the Sendai virus H cytoplasmic tail, fusion PCR was performed. The SeV H-tail encoding region was amplified from the pGem4-SVHN plasmid template (described by Vidal et al., supra) with primers 5'-CCATCGATAATCATGGATGGTGATAGGGG-3' (SEQ ID NO:29) and 5'-GCAAAACATAAGGGGTGTCAACTTTACTTGA-3' (SEQ ID NO:30). The primer 5'-GACACCCCTTATGTTTTGCTGGC-3' (SEQ ID NO:31) and a primer annealing downstream of the region coding for the H transmembrane domain were used to amplify the MV H transmembrane encoding region. In the fusion step, the isolated PCR fragments with an overlapping sequence of 19 nucleotides (underline) were mixed and amplified with the external primers. The resulting fragment was digested with ClaI and EcoRI and then subcloned into peH5.

The various peH5 subclones carrying the H mutant coding sequences were digested with ClaI and EcoRI and the H mutant fragments inserted into p(+)MV. Infectious viruses comprising the H protein mutations were rescued from transfected cells according to the method of Radecke et al. (1995, supra) and used to infect Vero cells at an MOI of 3. Cytopathic effects, including syncytia formation, were monitored over time by microscopic examination. Viruses encoding the H mutants HcA8, HcA14, and HcSeV produced syncytia, while HcΔ24 did not. HcA8 and HcA14 produced extensive syncytia (greater than 90% of nuclei in syncytia).

C. Combination of F and H Mutations.

Measles viruses encoding both mutated F and mutated H proteins were generated by replacing the PacI-SacII fragment encoding the H protein of the p(+)MV-Fc+28, p(+)MV-FcΔ24 and p(+)MV-FcSeV plasmids, with the PacI-SacII fragment encoding HcA14.

Double mutant viruses were rescued from cells transfected with the genomic plasmids as b above and used to infect Vero cell monolayers. All double mutants tested induced cell fusion more rapidly and more extensively than wild-type virus. At 36 hours post-infection, almost all of the cells infected with double mutant viruses were fused in large syncytia (>100 nuclei per syncytium), as compared to nearly no syncytia at the same time in cells infected with wild-type virus.

D. Modification of Measles Virus Fusogenicity by Alteration of M Protein

An M protein-less mutant of measles virus was constructed by removal of a 960 nucleotide BglII-BclI fragment containing the M protein coding sequences from the p(+)MV plasmid, to generate p(+)MV-M (Cathomen et al., EMBO J, supra). The M-less genomic plasmid was transfected into 293-3-46 helper cells (Radecke et al., 1995, supra). After 3–5 days, syncytia were observed, indicating rescue of infectivity.

Infection of Vero cell monolayers with M-less measles virus showed that at any given time after infection, the MV-ΔM syncytia were larger than those induced by wild-type reference virus. Quantitation of the extent of cell fusion after infection with a MOI of 0.01 revealed that after 4 days approximately 75% of the nuclei of an MV- M-infected cell monolayer were in syncytia, compared with approximately 25% of the nuclei of MV infected cells. After 6 days, >90% of the cells in both cultures were involved in syncytia, and cell mortality was substantial. These data indicate that the M-less virus is more efficient than the standard MV at inducing cell-cell fusion.

EXAMPLE 3

Paramyxoviridae Virus Expressing a Cytokine

A Paramyxoviridae virus modified to express IL-12 is constructed as follows. IL-12 is comprised of two subunits, p35 and p40. The sequences for both subunits are encoded by plasmid pBsIL-12, separated by an IRES from encephalomyocarditis virus (plasmid is described in Hemmi et al., 1998, Hum. Gene Ther.). pBsIL-12 was digested with NotI/XhoI and blunted, and the resulting 2306 bp fragment was ligated into the NruI site of peFHaigrL (described in Singh and Billeter, 1999, J. Gen. Virol. 80; 101) to obtain peFHLIL-12. A PacI-Spe fragment of peFHLIL-12 was placed in p(+)MVNSe (containing the antigenomic MV tag-Edmonston B sequence, slightly modified from p(+)MV (Radecke et al., 1995, supra) to exhibit unique NarI and SpeI sites) to obtain plasmid p(+)MVIL-12. This locates the IL-12 sequences between the H and L coding regions as an additional cistron.

The MV-IL 12 virus is rescued using the method of Radecke et al. (1995, supra). Syncytia developing in the rescue cultures are picked and used to infect Vero cell monolayers to expand the virus.

Expression of IL-12 directed by the virus is demonstrated by Western blotting protein from infected cells using antibodies specific for IL-12. IL-12 produced by virus-infected cells is tested by monitoring induction of IFN-γ secretion from peripheral blood mononuclear cells (PBMCs); see Singh and Billeter, 1999, J. Gen. Virol. 101.

EXAMPLE 4

Paramyxoviridae Virus Modified to Alter Protease Sensitivity

A Paramyxoviridae virus dependent on trypsin cleavage, rather than furin cleavage, for activation of infectivity is generated as follows.

A. Modification of Measles Virus F Protein

Measles virus F protein was modified by changing the arginine position 109 and the lysine at position 111 to asparagine. Cloning of the viral glycoprotein (H and F protein) genes into the expression vector pCG under the control of the CMV early promoter has been described by Cathomen et al., 1995, supra. The F cleavage mutant (pCG-Fcm) with substitutions in the furin recognition motif was prepared by introduction of site-specific mutations (underlined) with the complementary primers Fcm1 (5'-GCTTCAAGTAGGAACCACAACAGATTTGCGGG-3') (SEQ ID NO:32) and Fcm2 (5'-CCCGCAAATCTGTTGTGGTTCCTACTTGAAGC-3') (SEQ ID NO:33) into the double-stranded pCG-F plasmid using the QuikChange Site-Directed Mutagenesis Kit (Stratagene). After dideoxy sequencing of the complete F gene, the mutagenized plasmid was used for transfection of 293 and Vero cells.

For the generation of recombinant MV, a derivative (p(+)MVNSe; Singh et al., 1999, J. Virol. 73: 4823) of the cDNA clone containing the full length MV Edmonston B based genome described by Radecke et al. (1995, supra) was used. To construct a full length MV genome with a mutated F protein, the F protein was mutagenized in the shuttle vector peF1 (Radecke et al., 1995) using the primer pair Fcm1 and Fcm2. A NarI-PacI fragment containing the F gene with the mutated cleavage site was subcloned into p(+)MVNSe and completely sequenced by the dideoxy method using an automatic sequencer (Perkin Elmer). The standard cDNA clone (p(+)MVNSe) as well as the mutated clone (p(+)MV-Fcm) were used to generate recombinant MV.

B. Virus Rescue and Preparation of Recombinant Virus Stocks

Transfection and rescue of MV were performed mainly as described by Radecke et al., 1995, supra). Briefly, 293-3-46 helper cells mediating both artificial T7 transcription and NP and P functions were transfected with 8 µg either p(+)MVNSe or p(+)MV-Fcm in the presence of 5 ng of plasmid encoding the MV polymerase (pEMC-La).

At two days posttransfection, cells were expanded. To induce syncytium formation in p(+)MV-Fcm transfected cells, cells were washed and activated for 2 h at 37° C. with DMEM/trypsin. After activation, cell growth was allowed to proceed in DMEM supplemented with 10% FCS. At 4 d posttransfection, transfected cells were scraped in OptiMEM (GIBCO-BRL) with trypsin (1 µg/ml) and adsorbed to Vero cell monolayers. After washing, infected Vero cells were kept in DMEM/trypsin because they tolerate a trypsin concentration up to 1.2 µg per ml of medium without detaching (in contrast to 293 cells). At 5 d posttransfection, multiple syncytia indicated the successful rescue of p(+)MVNSe (MV-Edm). First syncytia in the p(+)MW-Fcm rescue appeared 7 to 8 d posttransfection.

Single syncytia were picked for infection of a Vero cell monolayer in the presence of trypsin. When the cytopathic effect (CPE) reached 90%, the cells were scraped into 1 ml of the cell culture medium and subjected to two rounds of freezing and thawing. The cleared supernatants were considered as "plaque purified" recombinant virus (Mv-Edm, MV-Fcm). To produce virus stocks, cleared supernatants were taken to infect subconfluent Vero cell monolayers. During infection at 33° C., the cells were kept in DMEM/trypsin. Infected cells showing 90 to 100% CPE were scraped into the medium, frozen and thawed, aliquotted and stored at −80° C. Infectivity was determined by 50% endpoint dilution assay (TCID50, see Cathomen et al., 1998, J. Virol., supra).

C. Fusion Assay

Because of the sensitivity of 293 cells to trypsin, fusion activity was analyzed in transiently transfected or infected Vero cells, respectively. For syncytium formation, Vero cells were cotransfected with standard or mutant F gene (pCG-F, pCG-Fcm) and standard H protein gene (pCG-H). At 16 h posttransfection, the cells were washed twice with PBS to remove the FCS containing medium and were further incubated with DMEM. To one monolayer from each set of duplicate samples TPCK-treated trypsin (Sigma) at a concentration of 1 µg per ml media was added. At 24 h posttransfection, the transiently expressing cells were fixed with ethanol and stained with 1:10 diluted Giemsa's staining solution (Merck, Darmstadt, Germany). To analyze the biological activity of recombinant MV with a mutated F protein, subconfluent Vero cells were infected with standard (MV-Edm) or mutant MV (MV-Fcm) at a multiplicity of infection (MOI) of 0.01-0.1. The infected cells were cultivated at 37° C. in DMEM in the absence or presence of 1 µg trypsin per ml media. At 24 h postinfection, the infected cells were fixed and stained as described.

D. Immunostaining

Subconfluent Vero cells (1×105 cells) were grown on coverslips and infected with MV-Fcm at an MOI of 5 for 2 h at 37° C. The cells were intensively washed with PBS overlaid with DMEM or DMEM/trypsin and incubated for 28 h at 33° C. to allow one step growth in the presence or absence of trypsin. To quantify the amount of infected cells, immunostaining was performed. After fixation and permeabilization at −20° C. with methanol/acetone (1:1), MV positive cells were detected with a polyclonal rabbit antiserum raised against purified MV and a FITC-labeled goat anti-rabbit IgG (DAKO, Denmark). The samples were mounted in mowiol and 10% triethylendiamine. For quantification of infectious cell-free virus, the cell supernatant was collected before immunostaining of the infected cells (28 h p.i.). The supernatant (300 µl) was directly used to infect fresh Vero cells grown to subconfluency on coverslips.

To activate cell-free virus grown in the absence of trypsin, 1 µg TPCK-treated trypsin per ml supernatant was added. As a control, 300 µl of the supernatant without trypsin addition was used for infection. Virus adsorption in the absence or presence of trypsin was allowed to proceed for 4 h at 37° C. Then, the cells were washed several times with PBS overlaid with DMEM and incubated at 33° C., To quantify the amount of infected cells, the cells were fixed at 42 h p.i. and immunostaining was performed as described.

E. Mice Infections

The Ifnartm-CD46Ge mice used in this study have a targeted mutation (tm) inactivating the interferon receptor type I (Ifnar). Since a yeast artificial chromosome covering about 400 kilobases of human genome surrounding the CD46 gene (CD46Ge) was transferred to mice, these animals express CD46 with human-like tissue specificity (Mrkic et al., 1998, J. Virol. 72: 7420). Age-matched mice were used for infections at the age of 6 to 7 weeks. For intranasal inoculation a total volume of 50 µl of appropriate virus stocks was administered into both nares. Intracerebral inoculations were done along the midline by using a 27-gauge needle. The inoculum consisted of 30 µl of stock virus diluted in PBS.

F Histology and In Situ Hybridization Assay

Assays were basically performed as described previously (Mrkic et al., 1998). Briefly, mice were euthanized with $CO_{22}$, the lungs were removed and fixed in 4% PBS-buffered formaldehyde. Paraffin-embedded tissues were cut at 2–3 µm sections. For general histological analysis the sections were stained with hematoxylin/eosin (HE) staining solution. Detection of MV N mRNA in situ was performed with a digoxigenin (DIG)-labeled N RNA probe (30 pg/µg) followed by immunological staining with a DIG-nucleic acid detection kit (Boehringer Mannheim). The sections were counterstained with hematoxylin solution.

Transient transfection of the recombinant expression plasmids pCG-F and pCG-Fcm into 293 cells was used to monitor the effect of the alterations to the furin cleavage site on the cleavage of the protein. Western blot analysis of transfected lysates under non-reducing conditions indicated that the alteration of the furin cleavage site resulted in complete loss of cleavage of the F0 protein in the absence of trypsin.

The effect of the furin cleavage site modification on cell-cell fusion was tested by transfecting either wild-type or mutant F plasmids into Vero cells with a wild-type H gene expression plasmid (pCG-H). To activate uncleaved F protein on the cell surface, 1 ug of trypsin per ml was added to one of each set of duplicate samples at 16 hours posttransfection. Cells were fixed and stained at 24 hours posttransfection. Cotransfection of standard MV glycoproteins (H+F) induced syncytium formation in the absence and presence of trypsin. Coexpression of standard H protein and mutant F protein (H+Fcm) only induced cell fusion in the presence of trypsin, indicating that mutated F protein was transported to the cell surface where it could be biologically activated by trypsin cleavage to cause syncytium formation.

In order to rescue Fcm mutated virus, the Radecke method was used, except that trypsin was required. Therefore, the modification to the furin cleavage site renders the virus dependent on trypsin for activation of infectivity.

Vero cells infected with MV-Edm (wild-type strain) or Mv-Fcm at a multiplicity of infection of 0.01 to 0.1 in the presence and absence of trypsin were analyzed by Western blot at 24 h postinfection. About 95% of F protein was found as the F1 subunit in cells infected with standard or wild-type virus, regardless of whether trypsin was included in the medium. In contrast, 100% of the F protein migrated as precursor F0 when the mutant virus was used in the absence of trypsin. Only when mutant F protein was synthesized in infected cells cultivated in the presence of trypsin was a significant amount of the cleavage product F1 detected. This indicates that virus-derived mutant F protein, in contrast to standard F protein, was not susceptible to intracellular cleavage by trypsin. For these experiments, control probing of protein blots with anti-H antibodies indicated no difference in H expression between cells infected with mutant or wild-type virus, indicating that infection by MV-Edm and MV-Fcm was comparable and that H protein expression was not influenced by trypsin addition during 24 h of infection.

Similarly, cell fusion in infected cultures was not observed unless trypsin was included in the medium. In order to test for cell fusion activity of standard MV versus MV-Fcm, Vero cells were infected and cultivated in the absence and presence of trypsin and tested for syncytium formation at 24 h postinfection. MV-Edm cells showed trypsin-independent cell fusion activity. Cells infected with MV-Fcm did not show any syncytium formation when cultivated in the absence of trypsin, but cultivation in the presence of trypsin resulted in cell fusion activity.

As both MV-Fcm and MV-Edm are released from infected cells and do not significantly differ in the protein composition of viral particles, it was important to demonstrate that MV-Fcm grown in the absence of trypsin is actually noninfectious and activation of cell-free virus completely depends upon extracellular proteases. Subconfluent Vero cells were infected at an MOI of 5 for 28 h in the presence or absence of trypsin. To monitor the efficiency of infection, the infected cells were stained with an antiserum raised against purified MV. As expected, all cells were MV positive, and cells infected in the presence of trypsin showed almost complete fusion, whereas cells infected in the absence of trypsin did not show any syncytium formation.

To test if infectious virions were released into the culture media, supernatants were used to infect fresh Vero cells. The supernatant of MV-Fcm grown without trypsin was either used untreated or complemented with trypsin to a final concentration of 1 ug/ml. The supernatants were allowed to adsorb for 4 h at 37° C. and the removed by extensive washings. Since further infection was performed without trypsin, no virus spread occurred, and the amount of MV-infected cells directly reflects the amount of infectious particles. At 42 h postinfection, MV positive cells were detected by immunostaining. No MV-Fcm positive cell was detected after infection with supernatant of cells infected in the absence of trypsin. Addition of trypsin to this "noninfectious" supernatant during virus adsorption resulted in the infection of about 30% of the cells, clearly demonstrating that the supernatant contained cell-free MV-Fcm particles that could be activated by trypsin.

To examine the effect of the furin to trypsin alteration of MV-Fcm cleavage in vivo, a mouse model was used. A group of eight Ifnartm-CD46Ge mice were infected intranasally with 3×105 PFU to study the pathogenic effects of MV-Fcm replication after uptake through the respiratory route. As a control, six mice were infected with MV-Edm. The lungs were removed for histological analysis and in situ hybridization at 4 days postinfection when high levels of standard virus replication was observed. Standard MV-Edm infection causes acute lung inflammation, extensive hyperemia and diffuse hemorrhage in large areas of the lung (Mrkic et al., 1998, supra). Although less pronounced than in standard virus infection, mutant MV also caused pathological effects.

MV-Fcm infected mice revealed an increased cellular density and infiltration of inflammatory cells, particularly in the perivascular regions. To demonstrate virus replication, MV-infected cells were detected by MV N-specific in situ hybridization assay. After standard virus infection, MV positive cells were mainly found close by or in the alveolar epithelium, often in cell groups indicating virus spread by cell-cell fusion. In MV-Fcm infected mice, single virus-positive cells were distributed all over the whole lung tissue, but the majority was found in the alveolar walls. Cells of the bronchiolar epithelium were occasionally infected. No virus-positive cells were detected, indicating that virus spread by cell-cell fusion probably did not occur. The amount of virus-positive cells was rather small, suggesting that MV-Fcm replication was not as efficient as replication of parental MV-Edm. However, MV-Fcm was able to induce lymphatic infiltration in the lung. These findings support the notion that the F protein is activated in the lung by secreted proteases, resulting in productive infection in the lung.

The sensitivity of IfnarTM-CD46Ge mice to intracerebral infection with MV-Fcm was also tested. When infected with MV-Edm, 5 of 6 animals showed clinical signs of neural disease and died within one week after infection. In contrast, all mice infected with MV-Fcm survived and did not develop any signs of disease. Thus, MV-Fcm was not pathogenic in mice when inoculated in the brain, probably due to the lack of activating proteases in this organ.

EXAMPLE 5

Generation of a Library Containing Partially Ramdomized Sequence Between F1 And F2 (F Library)

In this example, the standard MV F cleavage signal RHKR (SEQ ID NO: 15), recognised by furin, is mutated using random primers to genearte a library with potentially novel cleavage specificities. To avoid restoring furin sensitivity, primers are designed such that positions 1,2,3, cannot be arginine or lysine.

```
                 Furin Cleavage  ▼
              1    2    3    4    5    6    7
   MV F0      R    H    K    R    F    A    G    (SEQ ID NO:34)
         Furin sensitive site        Beginning of F1 polypeptide
                                          ▲
```

Arginine is coded by (single amino acid codes):

```
   AGG
   AGA
   CGG
   CGA
   CGC
   CGT
```

Lysine is coded by:

```
   AAG
   AAA
```

The possible permutations of bases (as a result possible amino acids) are as shown:

```
Furin Cleavage  ▼
          1    2    3    4    5    6    7
          R    H    K    R    F    A    G    (SEQ ID NO:35)
                              L    I    A
Primer:
XAT XAT XAT XXX TTC GCA GGT
XCC XCC XCC XXX TTA ATA GCT (SEQ ID NO:36)
XTX XTX XTX XXX
```

To eliminate R or K from positions 1,2,3, the possible permutation of bases are as shown above (where X=Any base). Thus for position 1, the first base can be A, T, C or G), 2nd base can be A, C or T and 3rd base can be T or C.

To make the library of F cleavage mutants, a PCR fragment of measles F is first generated. Through introduction of BamHI sites in the PCR primers, the PCR fragment is made flanked by restriction sites for BamH1, facilitating cloning into the transfer vector (containing retroviral LTR elements) pMFG. pMFG is derived from pMFG nlsLac Z, by removal of the nlsLacZ fragment by BamH1 digest.

After introduction to the transfer vector, the plasmid library is co-transfected with retroviral gag-pol and envelope expression plasmids into AM12 viral producer cells. The retroviral library is harvested and used to infect Vero cells which have been previously transfected with pCGH plasmid. Infection may be performed in the presence or absence of protease/protease inhibitors. Syncytia are picked, or balls of multinucleated syncytia which have floated into the supernatant are picked and sorted according to size of the floating balls. The F fragment is amplified by PCR from picked syncytia and sequenced to determine the linker sequence between F1 and F2.

EXAMPLE 6

Attenuated Measles Virus Targeting Specificity for CD38

A. Generation of Recombinant Viruses Displaying Single Chain Antibody Fragments

Figure 5:
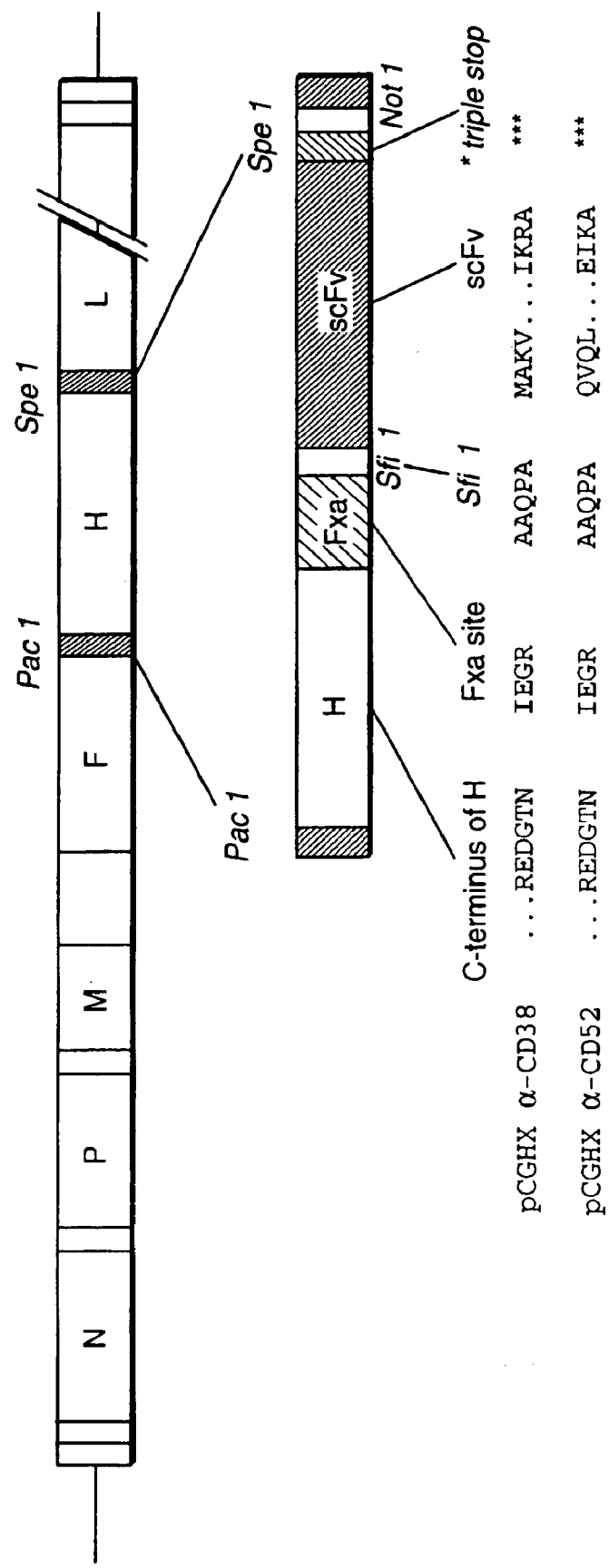

In one embodiment of the invention, the targeting specificity of an attenuated virus was altered by displaying a single chain antibody (ScFv) on the surface of the virus. In this embodiment, cDNAs coding for scFvs against a human lymphocyte differentiation antigens CD38 and CD52 were ligated into a full length infectious clone of MV-Edm (FIG. 5). The genes were inserted as in-frame fusions linked to the C-terminal codon of the H glycoprotein through a linker sequence encoding an IEGR (single amino acid code) (SEQ ID NO:37) factor Xa protease cleavage signal. MV-Edm recombinant viruses were recovered from these constructs and were amplified in CD46 receptor-positive Vero cells in which they replicated as efficiently as unmodified MV-Edm. Correct expression of the scFV domains was confirmed on immunoblots of cell lysates of infected Vero cells, and probed with an antibody against the H glycoprotein (FIGS. 6A–D).

B. Targeted Cell Entry and Cytotoxicity of MV-Edm Displaying an Antibody to CD38

Figure 6A:
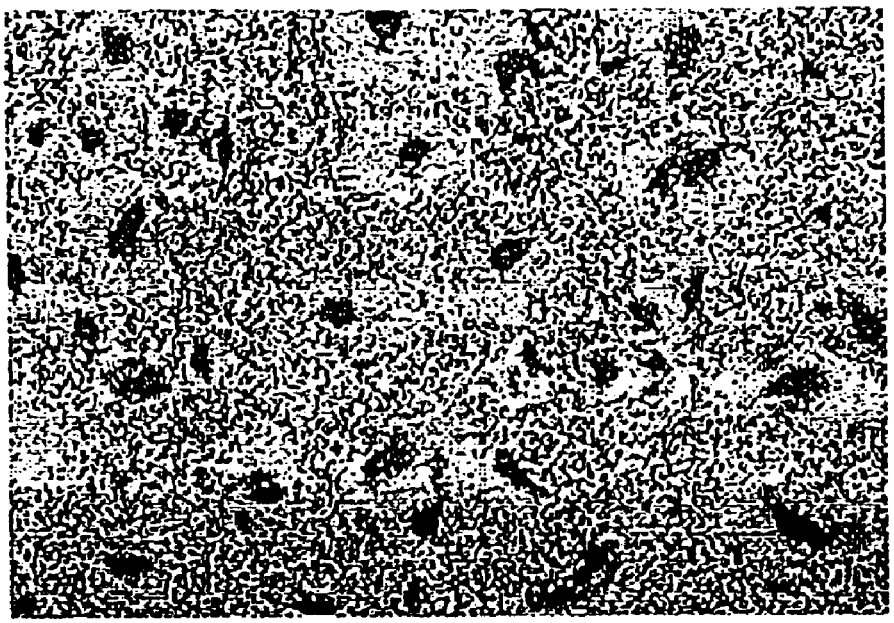
Figure 6B:
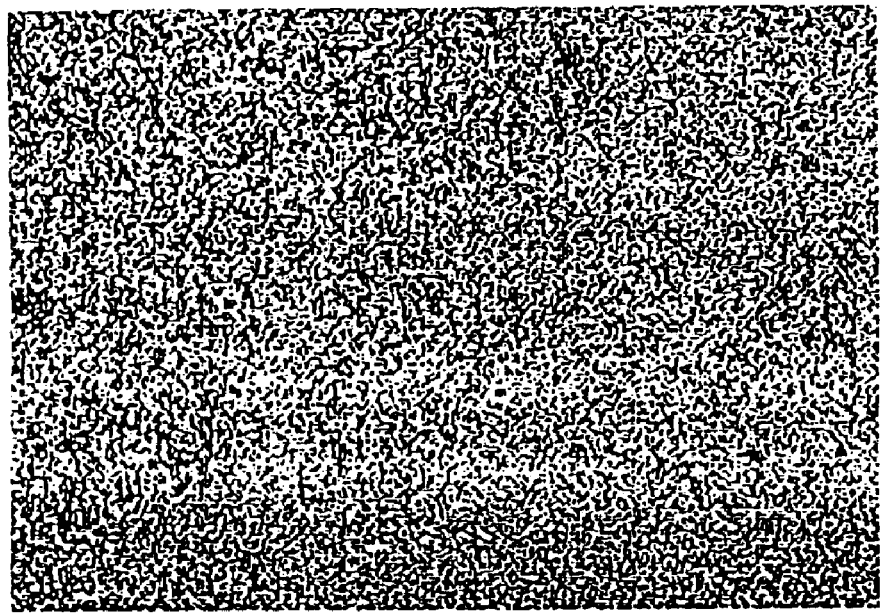
Figure 6D:
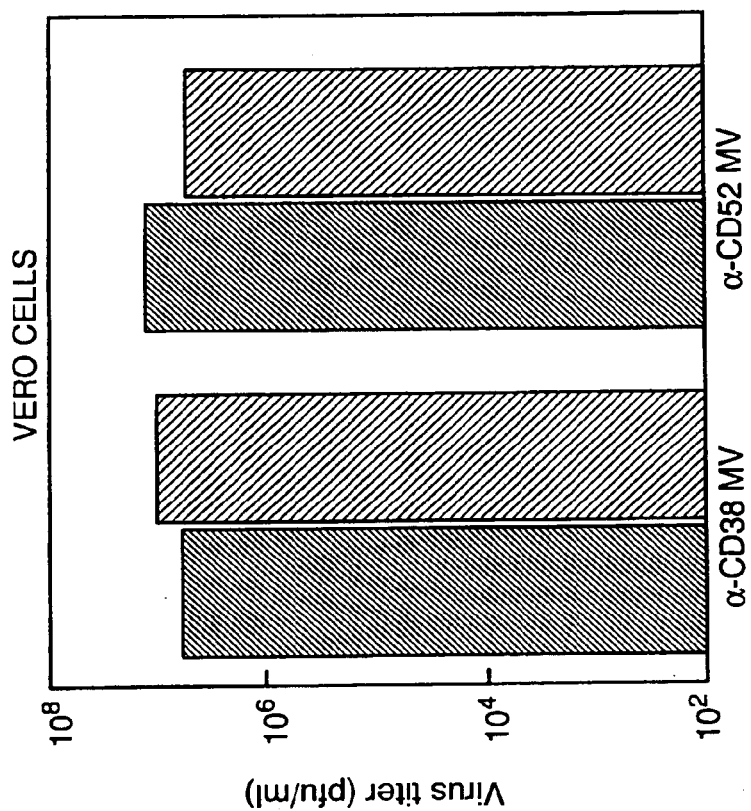
Figure 6C:
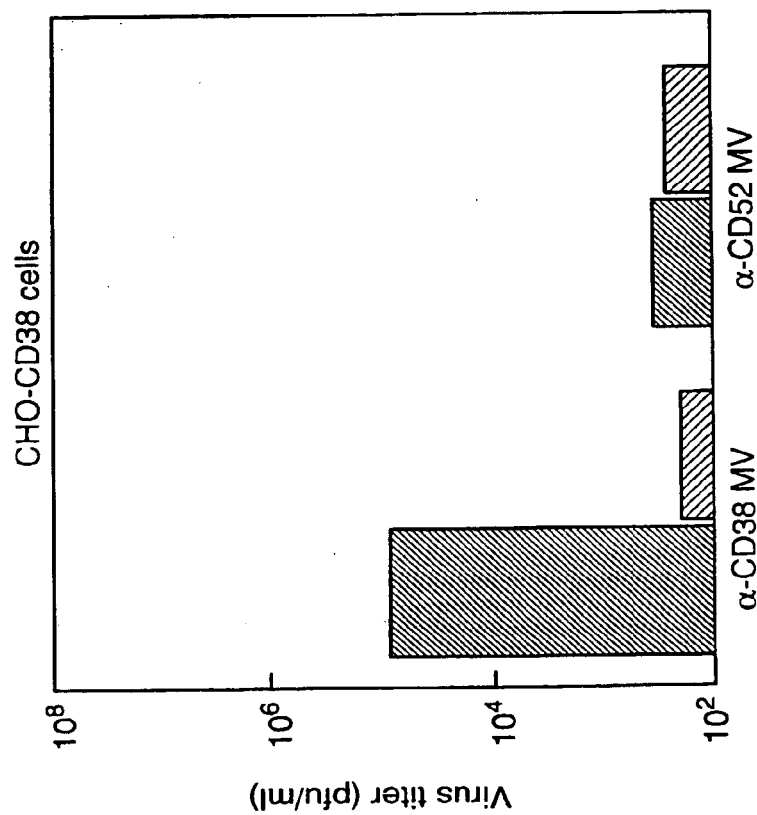
Figure 7:
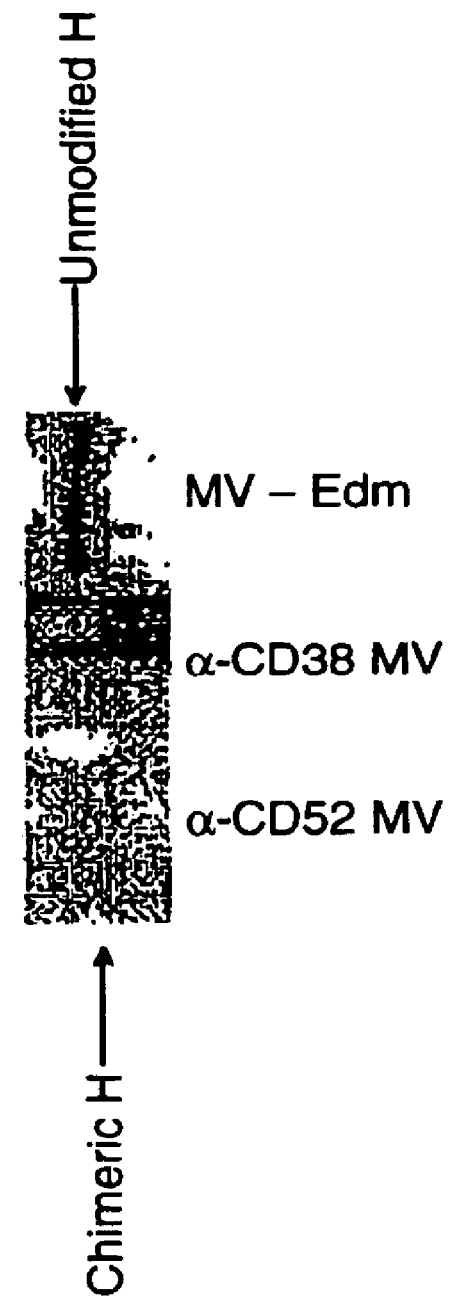

To determine whether the displayed anti-CD38 scFv could redirect virus attachment and entry, MV-Edm and scFv-displaying MV-Edm were titrated on CD46-negative Chinese Hamster Ovary (CHO) cells expressing human CD38 cells and control CHO cells. Infectious centers, defined as multinucleated syncytia containing more than 20 nucleic were counted 36 hours after invention. MV-EdM displaying an scFV against CD38 readily infected CD38-expressing CHO cells but was unable to infect unmodified CHO cells or CHO cells stably expressing human EGF-receptor (FIGS. 6A–D). Unmodified and CD52 scFv-displaying MV-Edm were not infectious on the CHO cells, irrespective of CD38 status (FIGS. 6A–D). Cleavage of the anti-CD38 antibody protion from the MV-Edm recombinant virus using Factor Xa protease ablated the infectivity of anti-CD38 scFv displaying virus on CD38-expressing CHO cells (FIGS. 6A-7). The virus was still able to infect CD46-expressing cells after protease cleavage, indicating that the functional integrity of the underlying H glycoprotein was not compromised by exposure to Factor Xa protease (FIG. 7).

EXAMPLE 7

Recombinant Measles Virus with Targeting Specificity for CEA

To redirect the tropism of measles virus (MV) to a targeted cell population, a single chain antibody (scAb) specific for the tumor associated carcinoembryonic antigen (CEA) was displayed on the viral hemagglutinin (H). The targeted antigen, CEA, is highly over-expressed on the surface of a number of cancerous cells, particularly of colorectal, gastric, lung, pancreatic and breast carcinomas. Its expression in normal adult tissue is restricted to selected epithelial cells, and the anti-CEA (αCEA) scAb used, MFE-23, has little cross-reactivity to non-malignant human tissue.

Constructs were generated expressing three forms of the αCEA MFE-23 scAb as C-terminal fusions of H (FIG. 8A). The scAb forms differed in the length of the linker separating the VH and VL domains, and were designated zero (0), short (S) and long (L), corresponding to linker lengths of 0, 6 and 16 amino acids, respectively. In each construct, the C-terminus of H was separated from the scAb by an 8 amino acid spacer including a Factor Xa cleavage site to facilitate removal of the displayed ligand. The chimeric HαCEA proteins were designated HX0, HXS and HXL accordingly.

To generate constructs in which the displayed scAb could be proteolytically cleaved away from the H protein, each scAb was PCR amplified from the pCG constructs using primers which generated a BssHII site upstream of the scAb cDNA, and which maintained the NotI site at the 3' end. These PCR products were digested with BssHII and NotI, purified and ligated with BssHII/NotI digested pCG-H-X-RGD, such that the RGD peptide in this construct was replaced with the scAb which was thus positioned 3' to the Factor Xa cleavage site (see FIG. 8A). Sequence analysis revealed all clones except the pCG-H—X—O-CEA to be correct.

Figure 9A:
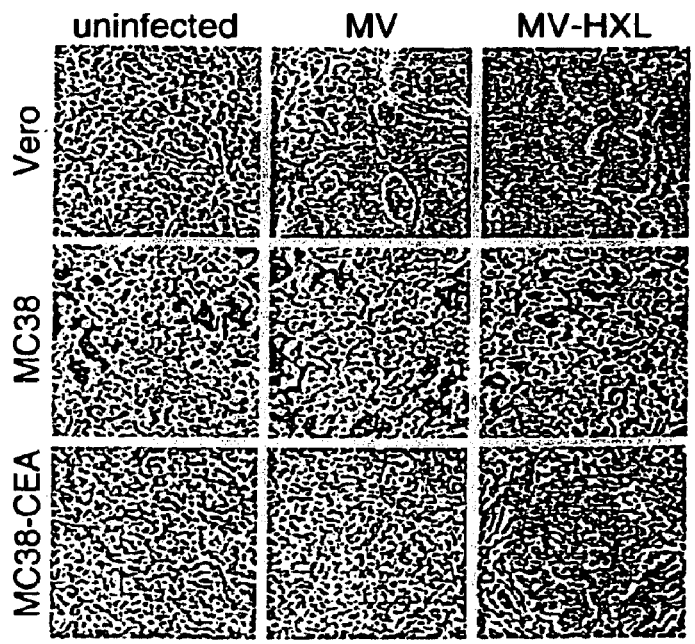
Figure 9B:
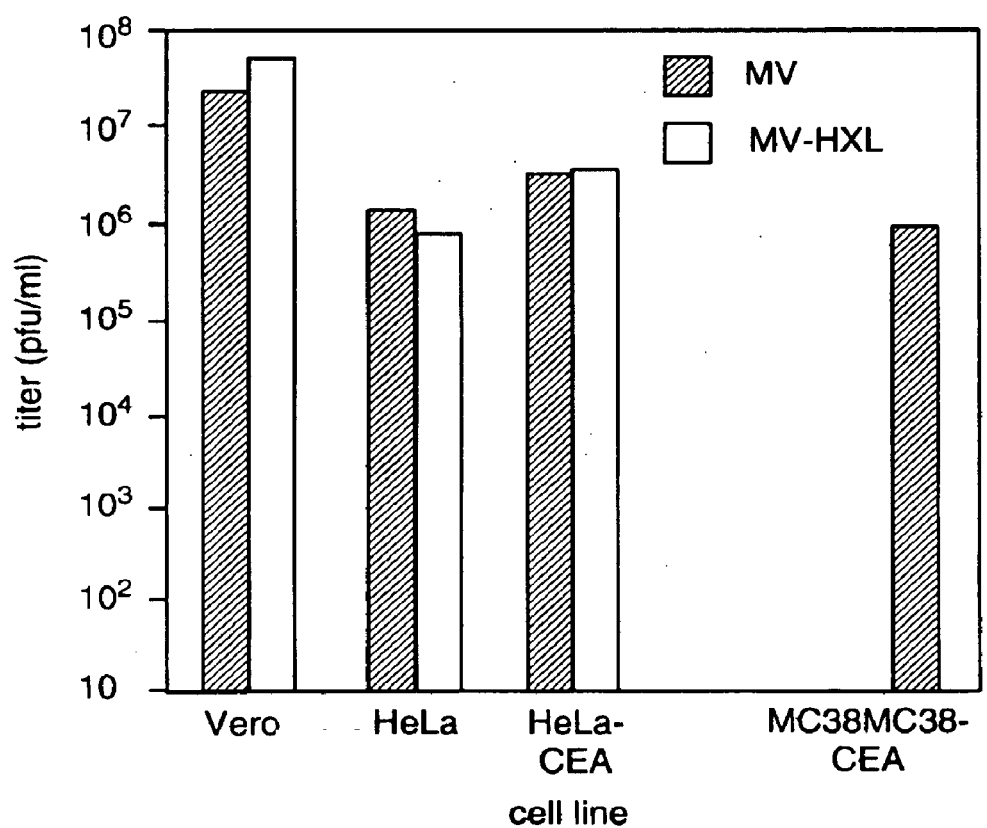

To test the ability of these chimeric H proteins to mediate fusion, and to test whether any re-directed the fusion function of H to CEA, each construct was co-transfected using Superfect (Qiagen) with the plasmid pCG-F encoding a functional MV F protein, into HeLa cells and HeLa cells overexpressing CEA. Cells were observed for syncytial formation, and numbers of syncytia were scored for each H-scAb construct (Table 2). The H protein expressing the long linker form of the scAb preferentially mediated fusion on HeLa-CEA cells (FIGS. 9A–B).

TABLE 2

Ability Of Chimeric H Proteins To Mediate Fusion On CEA Negative And Positive Cell Lines.

|  | HeLa or Vero | HeLa-CEA |
| --- | --- | --- |
| H5 + F | +++++ | +++++ |
| H5-O-CEA + F | − | − |
| H5-S-CEA or H5-X-S-CEA + F | − | + |
| H5-L-CEA or H5-X-L-CEA + F | ++ | ++++ |

To generate recombinant MV expressing a scAb directed against CEA, the cDNA encoding H—X-L-CEA was digested from the pCG construct using the enzymes PacI and SpeI, purified and ligated with PacI/SpeI digested p(+)MV-NSe, to generate the construct p(+)MV-NSe-H/X-L-CEA. Virus was recovered by calcium phosphate co-transfection of this plasmid along with pEMC-La, encoding the MV polymerase L, into 293-3–46 cells stably expressing T7 polymerase and the MV proteins N and P. Following overlay of these transfected cells onto Vero cells, observed syncytia were picked and the virus expanded by passage on fresh Vero cells.

All proteins were stable, appeared properly folded, and were transported to the cell surface, but only H displaying the long linker form of scAb (HXL) was functional in supporting cell-cell fusion. HXL induced extensive syncytia in cells expressing the normal virus receptor CD46, and also in CD46-negative cells expressing the targeted receptor, human CEA. Replication competent MV with H substituted by HXL was recovered, and was dual tropic, replicating efficiently in both CD46-positive and CD46-negative, CEA-positive cells. Thus MV not only tolerates the addition of a large scAb on its H protein, but can be engineered to infect cells via a novel interaction between a displayed scAb and its targeted receptor.

The long linker form induced extensive syncytia in both CD46-positive and CD46-negative, CEA-positive cells. A replicating MV expressing this chimeric protein in place of H was generated. Significantly, this virus replicated not only with the efficiency of unmodified MV in CD46-positive cells, but almost as efficiently in CD46-negative cells expressing CEA, which unmodified MV failed to infect.

A. Plasmid Construction and MV Recovery cDNAs encoding the three forms of the scAb were transferred to a pCH-H vector (17) containing a Factor Xa cleavage site 3' to the H ORF from retroviral expression vectors (J. Zhang, data not shown) using PCR amplification (primer sequences: 5'-GCGCGCTGGCCCAGGTG-3' (SEQ ID NO:38) and 5'-TGCGGCCGCCCGTTTC-3' (SEQ ID NO:39), BssHII and NotI sites underlined). For detection purposes, an amino-terminal Flag tag (DYKDDDDK) (SEQ ID NO:40) was inserted downstream of the ATG start codon of each H construct. DNA sequencing confirmed the integrity of all constructs. The cDNA encoding HXL was transferred from the pCG construct into a molecular clone of MV-Edmonston, p(+)MV-Nse(18). Virus was rescued as previously described (19).

B. Cell Culture and Transfection

Vero, HeLa, HeLa-CEA and MC38 cells were maintained in 10% FCS/DMEM. MC38-CEA (clone 2) cells (Robbins, et al. Cancer res. 51: 3657–3662) were maintained in 10% FCS/DMEM containing 0.5% G418. Cells were transiently transfected using Superfect (Qiagen) and analyzed 18–24 hours post-transfection. For syncytia formation assays, target cells (5×105/well, 35 mm wells) were co-transfected in duplicate with 1.5 µg DNA encoding F and 1.5 µg DNA encoding the appropriate H protein. Syncytia in 20 representative fields (20% of a 35 mm well) were counted at indicated times and the number of syncytia per well calculated.

C. MV Stocks and Infection

Preparation of MV stocks, virus propagation, purification and titration were performed as previously described (Radecke, et al., EMBO 14: 5773–5784). For infection, the appropriate MOI of cell-associated virus was adsorbed for 2 hours with target cells (5×105/well, 35 mm wells). For proteolytic digestion of the displayed domain, viruses in clarified cell extracts (MOI of 1) were pretreated with 10 µg/ml Factor Xa (New England Biolabs) for 2 hours at 23° C. prior to adsorption. For antibody adsorption of cell surface CEA, cells were pretreated with 10 ɡg/ml COL1 (LabVision Corp.) for 2 hours prior to infection with an MOI of 1. For both treatments, levels were maintained at 10 µg/ml by replacing with fresh media containing inhibitor every 12 hours.

D. Western, Pulse Chase and H Dimerization Analyses.

Western analysis of MV proteins from transfected or infected cells, pulse chase analysis of H from transfected Vero cells and analysis of hetero- and homotypic H dimerization, was performed as previously described (Plemper, et al., J. Virol. 72: 1224–34, 1998). HαCEA proteins were detected or immunoprecipitated using an αFlag Ab (M2, Sigma) and MV particles were analysed using an MV-specific goat antiserum.

E. Facs Analysis

Target cells (5×105/reaction) were incubated on ice in PBS/FCS/azide for 30 minutes, then with primary Ab for 1 hour at 4° C. Cells were washed, incubated with secondary Ab, repeatedly washed, fixed in 0.4% paraformaldehyde and analysed using a Becton-Dickinson FACSCalibur and CellQuest software. For detection of virus binding to the cell surface, cells were preincubated with virus at an MOI of 3 for 2 hours at 4° C. The 11/88 mAb (Schneider-Schaulies, et al.) J. Virol. 69: 2248–56, 1995)) was used to detect surface CD46, COL1 mAb to detect CEA, and mAb 129 (Sheshberadaran, et al. Virology 128: 341–353, 1983) to detect surface H and virus bound to the cell surface. All primary antibodies were realized using an αmouse-FITC conjugate (Jackson).

Figure 13A:
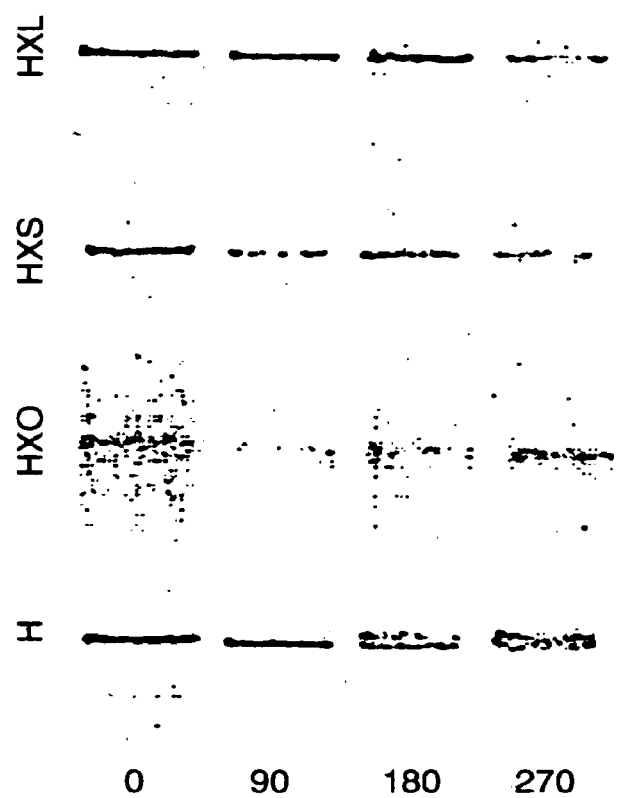

F. Expression, Stability, Oligomerisation and Cell Surface Localisation of Chimeric HαCEA Proteins Expression of HX0, HXS and HXL proteins at the expected molecular weight in all cell lines used was confirmed by Western blot analysis (shown in FIG. 8B for Vero cells, data not shown for HeLa, HeLa-CEA, MC38 and MC38-CEA cells). Furthermore, pulse chase analyses demonstrated a similar stability of expression for the chimeric HαCEA proteins as for unmodified H, with half lives for all proteins of greater than 3 hours (FIG. 13A).

Figure 13B:
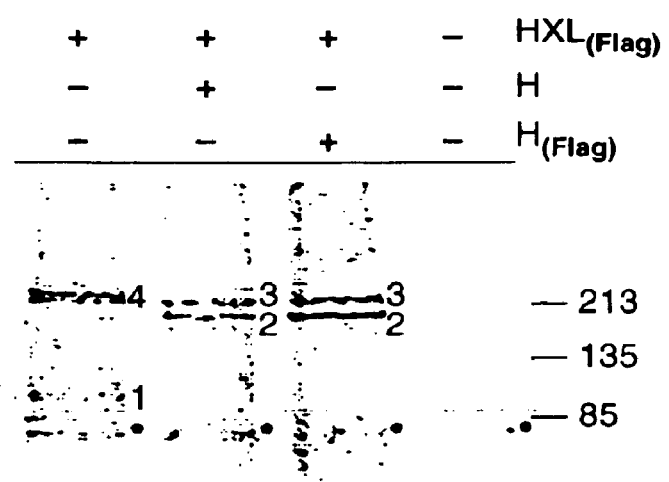

The H-like conformation of the HXL protein was verified by its ability to form covalently linked dimers with itself and with unmodified H. Following co-transfection of Flag-tagged HXL with unmodified, untagged H, or with empty plasmid or Flag-tagged H for control, cells were metabolically labelled. Using an αFlag Ab, tagged proteins and any interacting untagged H proteins were immunoprecipitated, and the dimerization status was analysed by gel electrophoresis under non-reducing conditions (FIG. 13B).

Both homotypic dimers of HXL/HXL and heterotypic dimers of HXL/H were identified. Under conditions in which both types of complex could form, the heterotypic HXL/H complex predominated, suggesting dimerization of HXL with unmodified H was more efficient than with itself The efficiency of both HXL/HXL and HXL/H complex formation was, however, reduced compared with that of H/H dimerization, thus display of the scAb on H reduces the efficiency of, but does not prevent, dimerization of the underlying H molecule.

Figures 1, 13C:
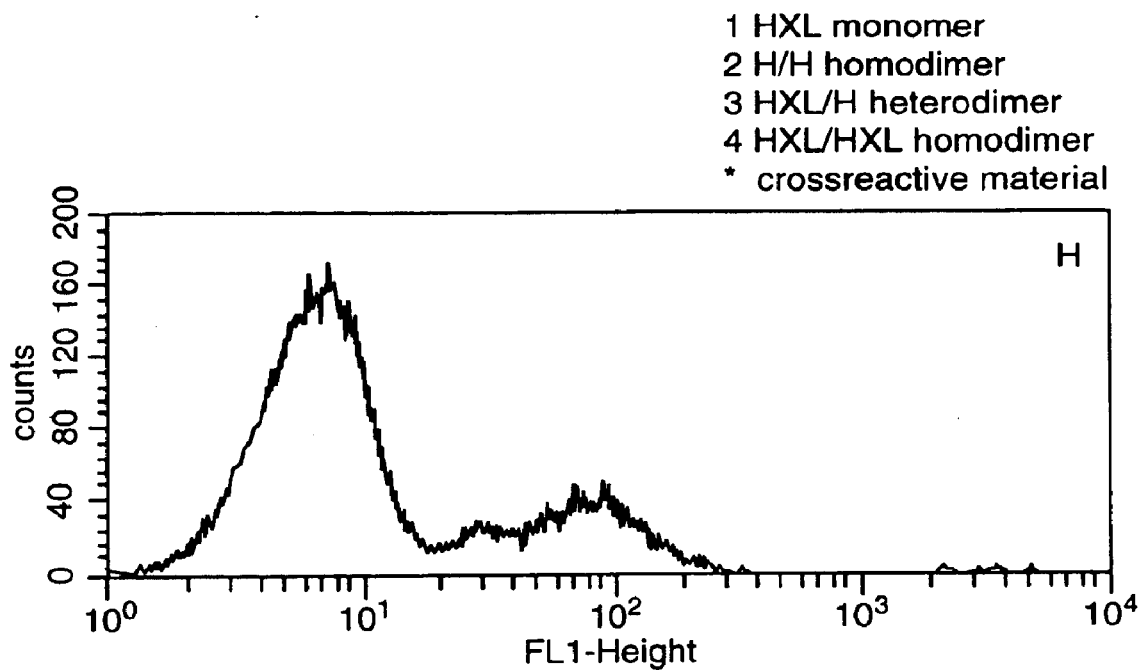
Figures 2, 13C:
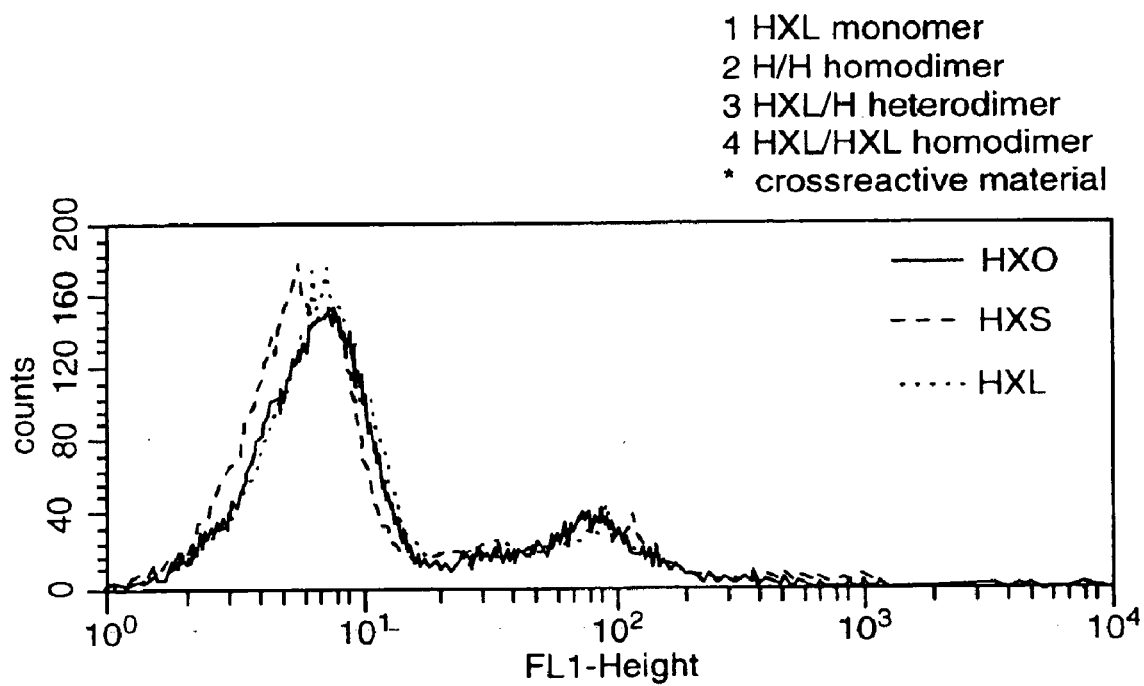

Since the formation of covalently linked dimers is a prerequisite for efficient H transport (Plemper, et al., J. Virol. 74: 6485–6493, 2000), our data suggested that the HXL protein should be efficiently transported. Indeed, cell surface expression of not only HXL but all HαCEA proteins was confirmed by FACS analysis of transfected cells to be similar to that of unmodified H (FIG. 13C), indicating efficient transport for all HαCEA proteins.

G. HXL Supports Syncytia Formation in Both CD46-Positive and CD46-Negative, CEA-Positive Cells Although display of a scAb on MV H did not affect its proper folding or transport, its receptor binding and fusion support functions may have been disrupted. We assessed the functionality of the HαCEA proteins by measuring syncytia formation following co-expression with MV F.

Figure 10A:
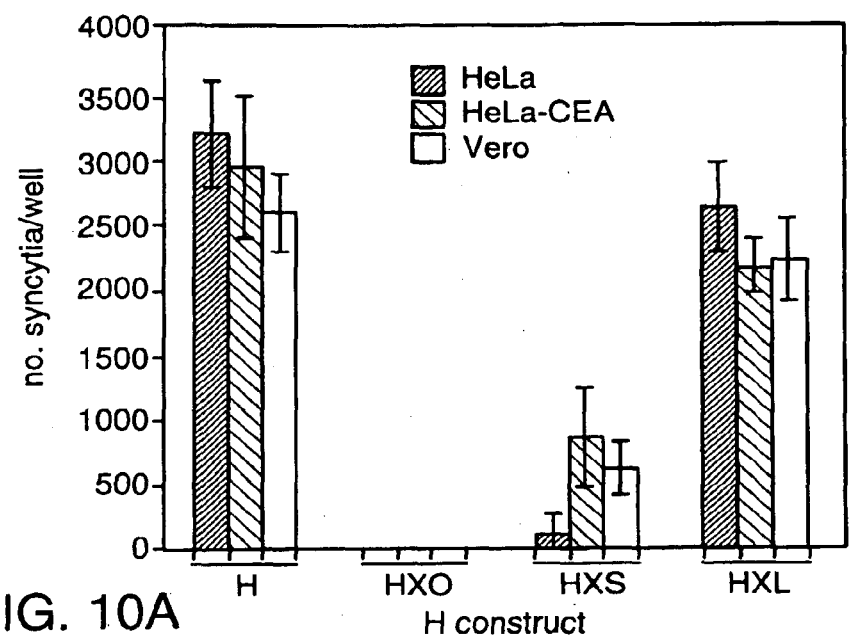
Figures 1, 10B:
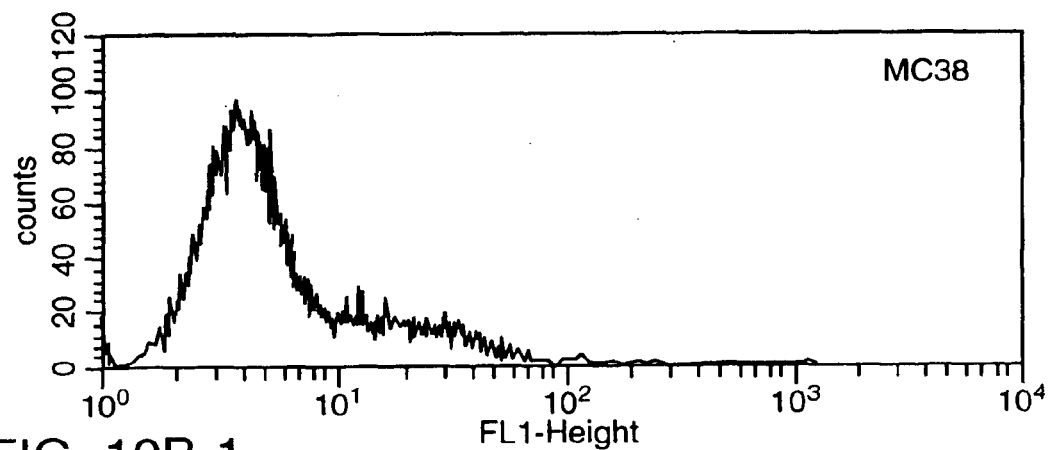
Figures 2, 10B:
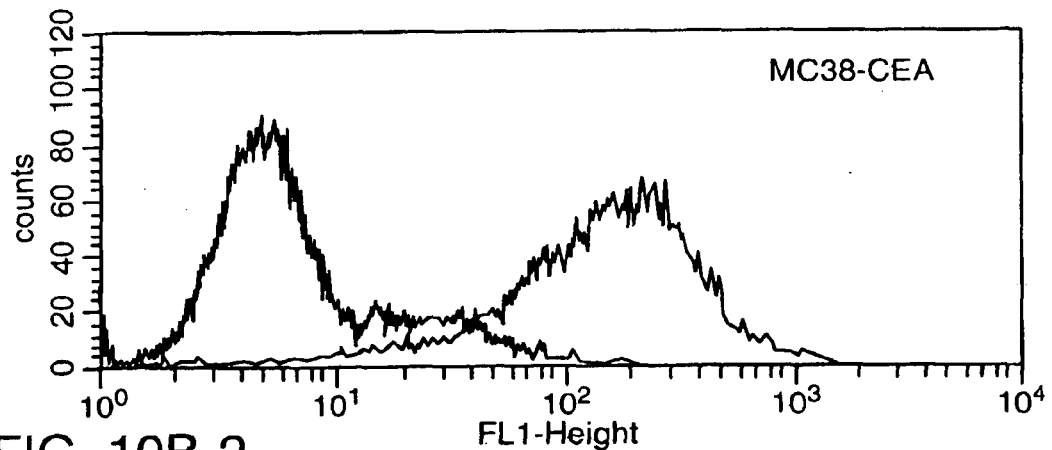
Figures 3, 10B:
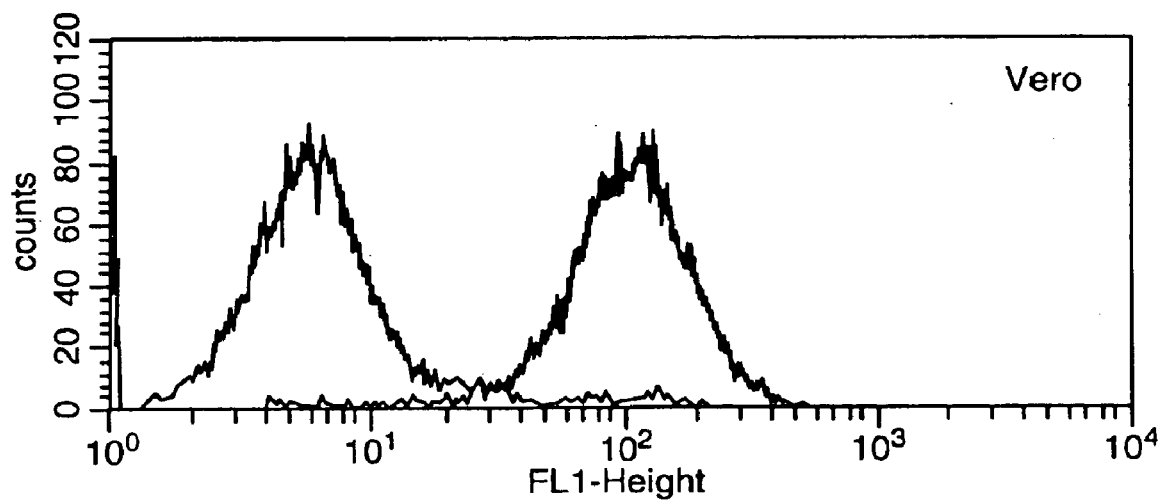
Figures 4, 10B:
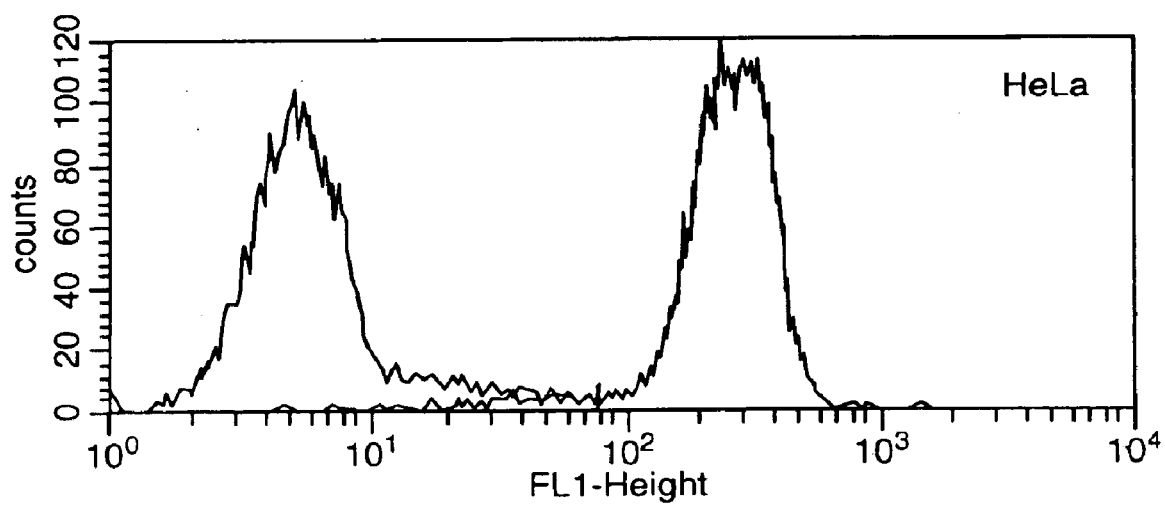
Figures 5, 10B:
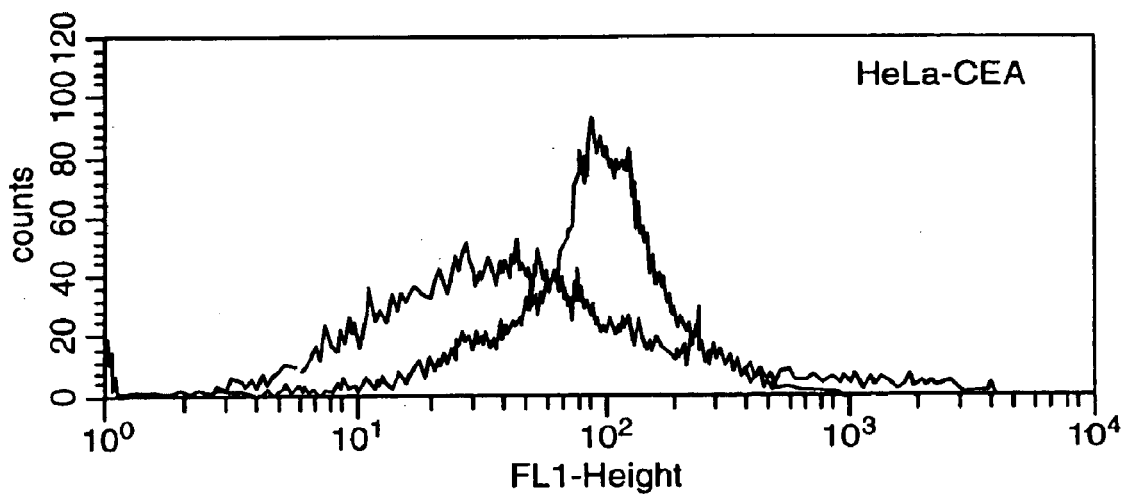

In three CD46-positive cell lines (HeLa, HeLa-CEA and Vero, FIG. 10A), expression of HXL with F induced extensive syncytia formation, to a similar degree as unmodified H. The HXS protein supported syncytia formation to a lower level, while no cell-cell fusion was observed in cells expressing HX0. No significant difference was observed in the numbers of syncytia in HeLa versus HeLa-CEA cells expressing any of the chimeric proteins. Thus addition of the long linker form of the scAb did not impair MV H-induced cell-cell fusion via CD46. To assess the contribution of the scAb-CEA interaction in the fusion process, we analysed CEA-dependent syncytia formation in a CD46-negative background. For this we used MC38-CEA cells, a mouse cell line stably expressing high levels of cell surface human CEA (Robbins, et al. supra.), and their CEA-negative parent, MC38. FACS analysis (FIG. 10B) demonstrated levels of CD46 to be similarly high on Vero, HeLa and HeLa-CEA cells, and undetectable on MC38 and MC38-CEA cells.

Figure 10C:
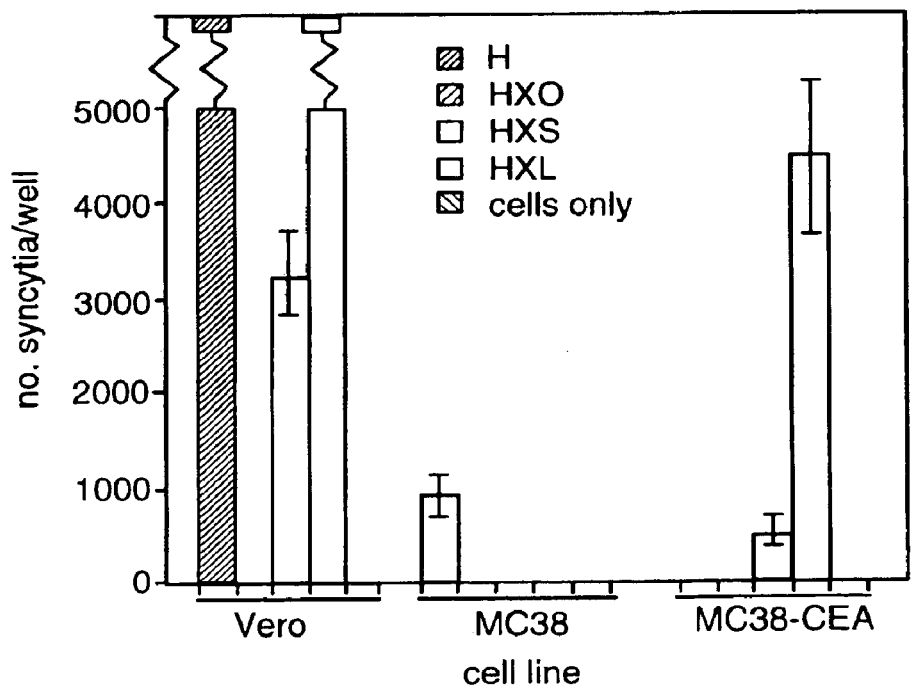
Figure 10D:
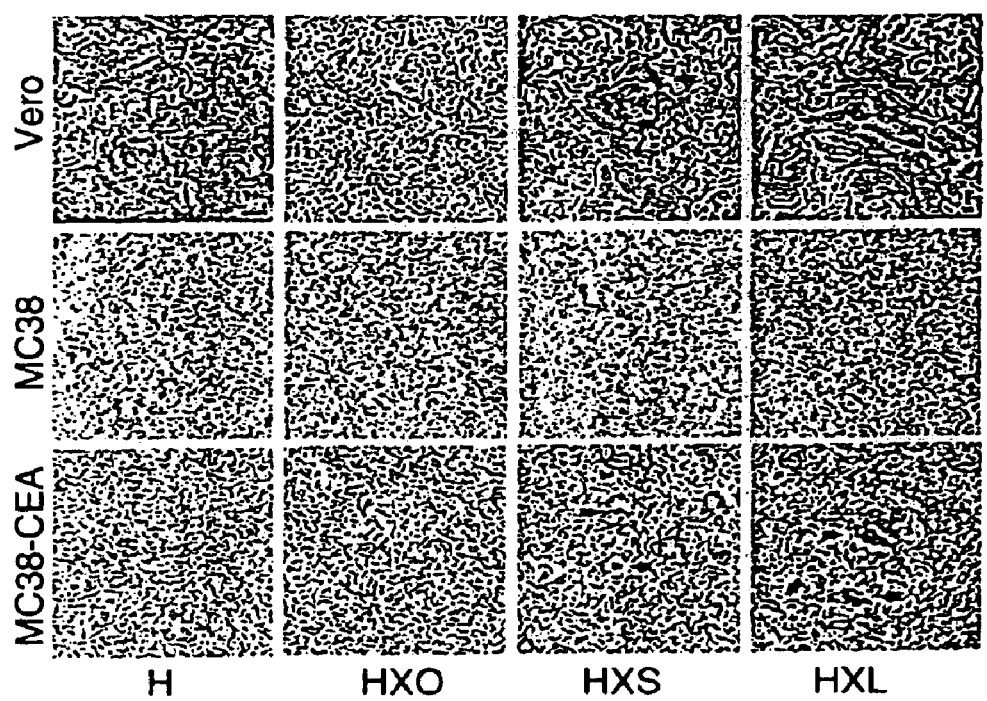

As expected, expression of CEA was high only on HeLa-CEA and MC38-CEA cells. Fusion was thus compared in MC38, MC38-CEA and Vero cells (FIGS. 10C and 10D). In MC38 and MC38-CEA cells, co-expression of F with unmodified H induced a low level of syncytia formation, presumably reflecting an inefficient, CD46-independent fusion mechanism for MV H. Strikingly, co-expression of F with chimeric HXL in MC38-CEA cells led to extensive syncytia formation. Although at a reduced level compared with that in Vero cells, numbers of syncytia were over 100-fold greater than that seen with unmodified H. The HXS protein supported a reduced level of syncytia formation in both Vero and MC38-CEA cells, while co-expression of HX0 with F yielded no detectable cell-cell fusion in any cell line. Thus MV H displaying the long linker form of the scAb initiated cell-cell fusion via a novel receptor.

H. Recovery of Replication Competent MV Containing Chimeric HXL Protein in Place of H The ability of chimeric HXL to functionally replace unmodified H in the context of replicating virus was assessed. In a full length infectious MV Edmonston cDNA, the H gene was replaced with that encoding HXL and, using the MV recovery protocol (Radecke, et al. supra)), virus was isolated from individual syncytia formed in Vero cells.

The authenticity of the recovered MV-HXL virus was confirmed by Western blot analysis of purified particles (FIG. 1A). Consistent with the sizes of transiently expressed HXL and H proteins (FIG. 8B), purified MV-HXL particles expressed an H protein of ~110 kD, in contrast to that of ~80 kD expressed from unmodified MV. Furthermore, treatment of purified MV-HXL virions with Factor Xa protease demonstrated specific cleavage of the appended scAb, generating an 80 kD protein corresponding to unmodified H (FIG. 11B). As expected, Factor Xa treatment of unmodified MV did not affect the size of the antigenic material detectable as H.

Figures 1, 11C:
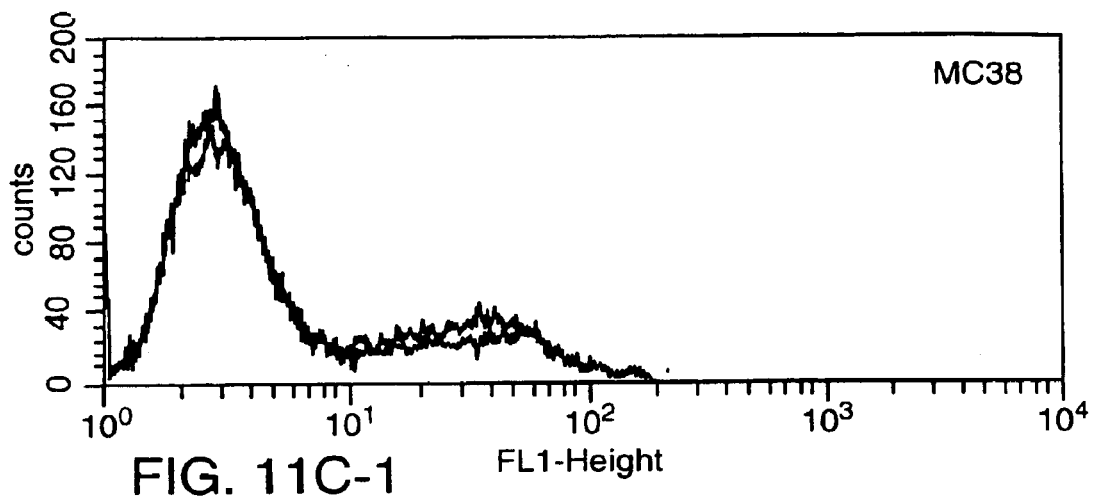
Figures 2, 11C:
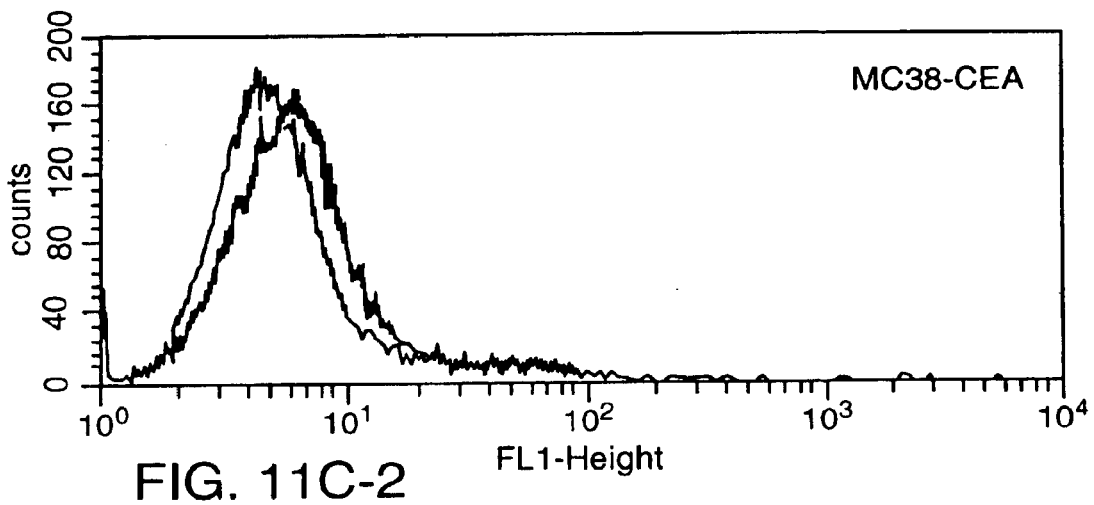
Figures 3, 11C:
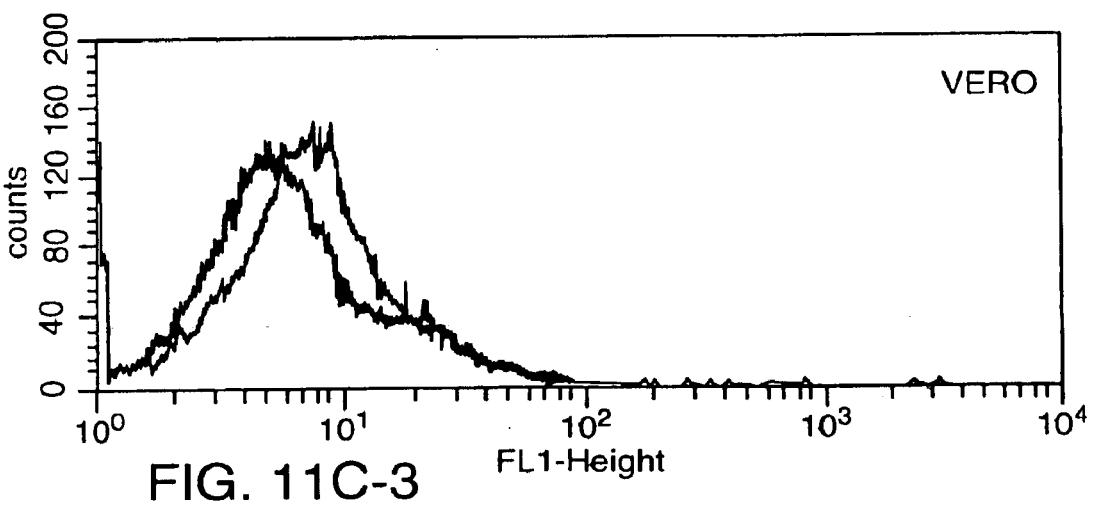

I. MV-HXL Virus Binds to the Surface of CD46-Positive and CD46-Negative, CEA-Positive Cells The ability of MV and MV-HXL to bind cells expressing either CD46or CEA at the surface was next compared by flow cytometry (FIG. 11C). Neither virus was able to bind the surface of CD46-negative, CEA-negative MC38 cells. In contrast, both viruses bound CD46-positive, CEA-negative Vero cells, with unmodified MV demonstrating a slightly higher binding ability. Thus the addition of the scAb did not negate the interaction of MV-HXL with cell surface CD46, consistent with the ability of HXL protein to induce cell-cell fusion in CD46positive cells. Importantly, the MV-HXL virus bound the surface of the CD46-negative, CEA-positive MC38-CEA cell line, while binding of unmodified Mv was negligible.

J. MV-HXL Virus Replicates in CEA-Positive Cells in the Absence of CD46

The infectivities of MV and MV-HXL for Vero, MC38 and MC38-CEA by observing syncytia formation in the inoculated cells (FIG. 9A). Consistent with previous results, Vero cells were infectable by either virus. Significantly, infection of MC38-CEA cells with MV-HXL resulted in extensive syncytia formation. In contrast, infection of MC38-CEA cells with unmodified MV, and MC38 cells with either virus was undetectable.

The replicative ability of MV-HXL was compared with that of unmodified MV by determining the viral titers achieved in Vero, HeLa, HeLa-CEA, MC38 and MC38-CEA cells by TCID50 assays using each of these cell lines as targets (FIG. 9B shows one typical example). MV-HXL replicated to titers almost indistinguishable from those obtained with unmodified MV in all three CD46-positive cell lines tested ($7 \times 10^5 - 5 \times 10^7$ pfiu/ml depending on the cell line). Thus the ability of MV-HXL to replicate in a CD46-dependent manner was not affected by display of the scAb, consistent with our previous data.

Remarkably, MV-HXL reached a similar titer on CD46-negative, CEA-positive MC38-CEA cells as on CD46-positive cells (from independent experiments, an average of $6.2 \times 10^5 +/- 1.3 \times 10^5$ pfu/ml), demonstrating that its ability to replicate in a CEA-dependent manner was about as efficient as its CD46-dependent replication. Negligible infection (titers of <$10^2$ pfu/ml) was detected in MC38-CEA cells with unmodified Mv, and in CEA-negative MC38 cells with either virus.

The infectivities of MV and MV-HXL were measured in all cell lines by infecting each with an MOI of 3 and quantifying cell-associated virus by TCID50 titration 72 hours post-infection using Vero cells as targets. Since no intrinsic differences in replication of the two viruses in Vero cells existed (FIG. 9B), no bias would be introduced using this approach. This method gave a reproducibly similar pattern of virus titers as the previous assay, but the absolute values were 1–2 logs lower, with the titer of MV-HXL on MC38-CEA cells reaching $3.1 \times 10^4 +/- 5.1 \times 10^3$ pfu/ml (data not shown). This assay was used for subsequent blocking experiments.

Figure 12:
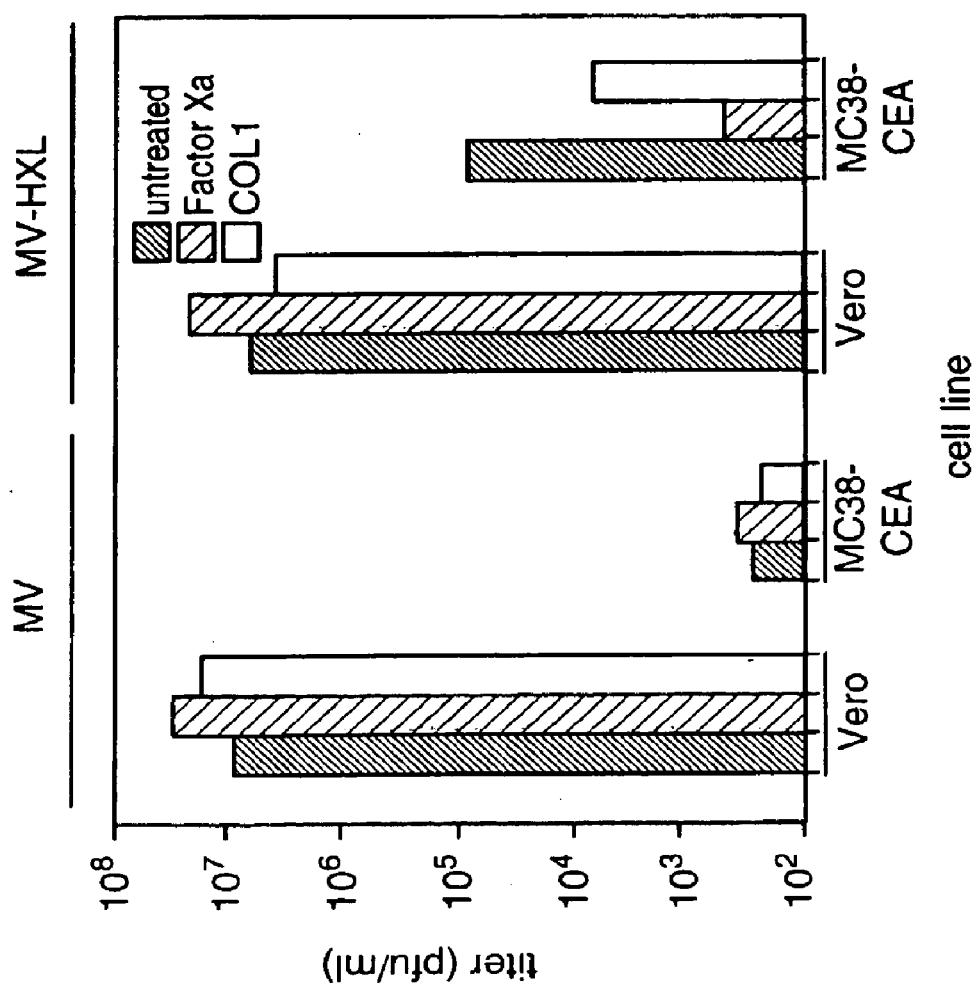

K. Replication Of MV-Hxl in CD46-Negative, CEA-Positive Cells Depends on a Specific Interaction Between the Displayed ScAb and CEA The infectivity of MV and MV-HXL for MC38-CEA and Vero cells following incubation of virus with Factor Xa protease to cleave the displayed scAb, or pretreatment of cells with an αCEA mAb (COL1) to block cell surface CEA, was examined. In both cases, virus was quantified from the cells 72 hours post-infection by TCID50 titration using Vero cells as targets (FIG. 12).

On Vero cells, neither treatment significantly affected the titer of either MV or MV-HXL; similarly, on MC38-CEA cells, the titer of unmodified MV was unaffected by either treatment. Strikingly, cleavage of the displayed scAb by Factor Xa protease reduced the titer of MV-HXL on MC38-CEA cells by greater than 100-fold (from independent experiments, an average of 177-fold+/−2-fold). Inhibition of MV-HXL by pretreating MC38-CEA cells with the αCEA mAb COL1 was less drastic but still significant, with an inhibition of greater than 10-fold. These data confirm that the ability of MV-HXL to infect CEA-positive cells independently of CD46 depends on a specific interaction between the displayed scAB and the targeted antigen.

Redirecting MV to a more clinically relevant target, CEA, establishes a precedent for the development of useful MV-based therapeutics. Moreover, given the common features of scAb structure, the ability to display one scAb suggests that MV H may tolerate the addition of many scAbs as C-terminal fusions; a property highly desirable for targeting vectors. Remarkably, the presence of two independently folding domains in these HαCEA molecules did not affect intracellular stability, suggesting their correct folding (Plemper, et al. supra.). More evidence that the conformation of the underlying H molecule was unaffected came from the ability of HXL to dimerize with itself and with unmodified H and from the similar cell surface expression of all HαCEA proteins compared with that of unmodified MV H.

Significantly, MV H displaying the long linker form of the αCEA scAb was able to initiate efficient cell-cell fusion in cells expressing CD46, and also in CEA-positive cells independently of CD46. In contrast, addition of the zero and short forms of the scAb ablated or reduced the fusogenicity of the molecule, respectively. Since the scAbs of the HX0 and HXS proteins may be oligomeric, they may sterically prevent fusion either by blocking interaction with either cellular receptor or a second factor, or by a more complex interference in the oligomerisation of H or the interaction between H and F oligomers. The HXL protein, however, is predicted to display a monomeric scAb, which apparently does not obstruct any essential complex formations.

The two appended Ig-like domains to the H protein did not appear to interfere with efficient particle assembly, despite the increase in molecular mass of the H protein by 40%. Furthermore, the displayed scAb did not impair entry and replication competence in CD46positive cells and significantly, enabled infection of cells lacking all human proteins other than the targeted receptor, human CEA, to titers similar to those achieved on CD46-positive cells. Moreover, the CD46-independent infectivity of MV-HXL for cells expressing CEA relied on a specific and inhibitable interaction between the scAb displayed on the virus and CEA.

CEA-dependent infection by MV-HXL can be described as 'positive retargeting' of MV, since binding to CEA is followed by CEA-dependent entry. These findings suggest the general applicability of MV as a vector which can be positively retargeted to many other cell surface antigens by display of appropriate scAbs. In addition to its inherent cytotoxicity, developing retargeted vectors based on the safe and effective MV-Edmonston vaccine strain supports the therapeutic use of replication competent virus. The combination of potent syncytium induction and replication competence may culminate in a more extensive spread amongst the target cell population.

EXAMPLE 8

Attenuated Measles Virus Targeting Specificity for EGF or IGF1

Hybrid proteins consisting of the epidermal growth factor (EGF) or the insulin-like growth factor-1 (IGF1) linked to the extracellular (carboxyl) terminus of the MV-Edm attachment protein hemagglutinin (H) were produced. The standard H protein gene was replaced by one coding for H/EGF or H/IGF1 in cDNA copies of the MV genome. Recombinant viruses were rescued and replicated to titers approaching those of the parental strain. MV displaying EGF or IGF1 efficiently entered CD46 negative rodent cells expressing the human EGF or the IGF1 receptor, respectively and the EGF-virus caused extensive syncytia formation, and cell death. Taking advantage of a factor Xa protease recognition site engineered in the hybrid H proteins, the displayed domain was cleaved off from virus particles, and specific entry in rodent cells was abrogated.

A. Plasmids

The parental plasmids pCG-F and pCG-H code for the F and H proteins of MV-Edmonston (9). Plasmids pCG-H/SfiI/NotI and pCG-H/XsfiI/NotI, the second including a factor Xa protease (FXa) cleavage signal before the SfiI/NotI cloning sites, were constructed and digested with SfiI and NotI to provide the backbone in which the coding regions for the displayed domains were inserted. The constructs pCG-H/hEGF, pCG-H/XhEGF, pCG-H/hIGF1 and pCG-H/XhIGF1 were made by transferring the SfiI/NotI hEGF and hIGF1 fragments from pEGF-GS1A1 (Peng, k. W., 1997, Thesis. University of Cambridge)) and pIGFNA1 (Chadwick, et al., J. Mol. Biol. 285:485–494), respectively, into SfiI/NotI-digested pCG-H/SfiI/NotI and pCG-H/XsfiI/NotI. The coding sequence of the linker region (IEGRAAQPAMA, one letter code) (SEQ ID NO:41) is 5'-ATCGAGGGAAGGGCGGCCCAGCCGGCCATG GCC-3' (SEQ ID NO:42). The four constructs were tested to verify their funtionality in cell fusion assays.

The PacI-SpeI fragments containing the hybrid H genes were corrected to comply to the rule of six (7/Calain, et al., J. Virol. 67:4822–4830, 1993)) by a PCR deleting one nucleotide between the stop codon (underlined) and the SpeI site (italics), the final sequence being 5'-TAGTAACTAGT (SEQ ID NO:43). The fragments were then inserted into PacI-SpeI digested p(+)MV-Nse (Singh, et al., J. Virol. 73:4823–4828, 1999) encoding the MV Edmonston antigenome, yielding plasmids p(+)MV-H/hEGF, p(+)MV-H/XhEGF, p(+)MV-H/hIGF1 and p(+)MV-H/XhIGF1.

Plasmids p(+)MVgreen-H/XhEGF and p(+)MVgreen-H/XhIGF1 encoding the enhanced green fluorescent protein as an additional transcription unit upstream of the N gene (Hangartner, 1997. M.Sc. Thesis. University of Zurich) were constructed using a unique SacII restriction site located within the P gene, and the SpeI site found downstream of the H coding region. The SacII/SpeI fragments from p(+)MV-H/XhEGF and p(+)MV-H/XhIGF1 containing the hybrid H genes were inserted into the SacII/SpeI opened backbone of p(+)MVgreen (Duprex, J. Virol. 73: 9568–9575, 1999)).

Construction of PCG-H/EGF and PCG-H/IGF.

Unmodified measles virus (MV) F and H proteins were encoded by the expression plasmids pCG-F and pCG-H, respectively (Cathomen et al., 1995, Virology, supra). To make the chimeric MV H expression constructs, the SfiI site in pCG-H was first deleted so that the displayed ligands could subsequently be introduced as SfiI/NotI fragments. This was achieved by digesting pCG-H with SfiI, filling in the cohesive ends by treating with the Klenow fragment of E. coli DNA polymerase and dNTPs, then re-ligating the purified, blunt-ended product. This construct, termed pCG-H(SfiI-) was tested to verify its functionality in cell fusion assays.

To introduce the SfiI/NotI cloning site at the C-terminus of the H sequence, thus enabling ligands to be inserted as SfiI/NotI fragments, oligonucleotides HXmabak (5'-CCG GGA AGA TGG AAC CAA TGC GGC CCA GCC GGC CTC AGG TTC AGC GGC CGC ATA GTA GA-3') (SEQ ID NO:44) and Hspe for (5'-CTA GTC TAC TAT GCG GCC GCT GAA CCT GAG GCC GGC TGG GCC GCA TTG GTT CCA TCT TC-3') (SEQ ID NO:45) were synthesised. When annealed, these two oligonucleotides form a DNA fragment with XmaI and SpeI cohesive ends which was ligated with XmaI/SpeI digested (pCG-H(SfiI-) backbone. The correct sequence of this construct, pCG-H-SfiI/NotI was verified by DNA sequencing.

To make the construct pCG-H-FX-SfiI/NotI, which includes a factor Xa protease (FX) cleavage signal before the SfiI/NotI cloning sites at the C-terminus of the MV H sequence, oligonucleotides HXmaFXbak (5'-CCG GGA AGA TGG AAC CAA TAT CGA GGG AAG GGC GGC CCA GCC GGC CTC AGG TTC AGC-3') (SEQ ID NO:46) and HNotFXfor (5'-GGC CGC TGA ACC TGA GGC CGG CTG GGC CGC CCT TCC CTC GAT ATT GGT TCC ATC TTC-3') (SEQ ID NO:47) were synthesised. When annealed, these two oligonucleotides form a DNA fragment with XmaI and NotI cohesive ends which was ligated with the XmaI/NotI digested pCG-H-SfiI/NotI backbone. The correct sequence of this construct was verified by DNA sequencing.

Constructs pCG-H-EGF, pCG-H—X-EGF, pCG-H-IGF and pCG-H—X-IGF were made by transferring the SfiI/NotI EGF and IGF fragments from pEGF-GS1A1 (Peng, PhD thesis, the entierty of which is incorporated by reference herein) and pIGFA1 (WO97/03357, Russell et al., the entierty of which is incorporated by reference herein) respectively into SfiI/NotI digested pCG-H-SfiI/NotI and pCG-H-FX-SfiI/NotI. FIG. 14A shows the pCG-H/(X)hEGF and pCG-H/(X)hIGF1 constructs.

B. Cells, Viruses and Infections

Cells were grown in Dulbecco's modified Eagle's medium supplemented with 5% fetal calf serum (DMEM-5) for Vero (African green monkey kidney) and A431 (human carcinoma) cells, 10% fetal calf serum (DMEM-10) for CHO (Chinese hamster ovary) cells, or DMEM-10 containing 1 mg/ml G418 for the rescue helper cell line 293-3-46 (human embryonic kidney), CHO-hEGFr, CHO-hEGF.tr and 3T3-hIGF1r (mouse fibroblasts) cells. The Edmonston B-based parental MV strain and all its recombinant derivatives were rescued, propagated and purified basically as described previously (Radecke, et al. supra.)). Viral titers were determined by 50% end point dilution assays (Cathomen, et al., J. Virol 72: 1224–1234, 1998).

Infections were generally performed in Opti-MEM I reduced serum medium (O-MEM, Gibco). One day prior to infection, $4\times10^5$ cells were seeded into a 35-mm well. Before infection, cells were washed with 2 ml O-MEM and the infection was performed in 1 ml O-MEM for 1–2 hours at 37° C. The cells were washed again in 2 ml O-MEM and overlaid with 2 ml DMEM-5 or DMEM-10 depending on the cell line infected.

C. One-Step Growth Analysis

Vero cells ($5\times10^5$) were infected with parental and recombinant MV at an MOI. of 3 for 2 hours. After infection, the cells were overlaid with 1 ml DMEM-10 and incubation was continued at 32° C. Released and cell-associated virus samples were collected at different times post infection. Cell-associated virus was subjected to one cycle of freeze/thawing and then the samples were stored at −80° C. for at least 4 hours prior to titration. Before titration, the samples were centrifuged in a table-top centrifuge (Spectrafuge 16M, Labnet) for 2 min at 8000 rpm to remove cell debris.

D. Purification of Viral Particles

For each virus two T175 bottles (Falcon) with Vero cells of 80% confluency ($2\times10^7$) were infected at an MOI of 0.1 for 2 hours at 37° C. The infection solution was replaced by 20 ml DMEM-5 and cells were incubated at 32° C. until 80–100% of all nuclei were found in syncytia. Supernatants were collected in 36-ml polypropylene tubes (Sorvall) and clarified by 30 min centrifugation at 8000 rpm in a Surespin 630 rotor (Sorvall). Clarified supernatants were transferred into new 36-ml tubes and pelleted by velocity centrifugation (2 hours at 28000 rpm) through 20% sucrose onto a 60% sucrose cushion prepared in TNE buffer (10 mM Tris-HCl [pH 7.5], 100 mM NaCl, 1 mM EDTA [pH 7.5]). The fraction containing the virus was harvested, diluted by addition of TNE and pelleted at the bottom of the tube by 2 hours centrifugation at 28000 rpm. After careful removal of all liquid, viruses were dissolved in 200 $\mu$l phosphate-buffered saline (PBS, Gibco) and stored at −80° C.

E. Receptor Saturation Assays

Vero, CHO-hEGFr and 3T3-hIGFr cells ($5\times10^5$) were incubated in 0.5 ml O-MEM containing either HEGF or hIGF1 (R&D Systems, 236-EG and 291-GI) for 30 min at 37° C. For infection, another 0.5 ml O-MEM containing the virus was added to each well, yielding final hEGF and hIGF1 concentrations of 0.25 and 1 $\mu$M or 0.05 and 0.2 $\mu$M, respectively, in 1 ml of O-MEM. Infection was allowed to continue for 3 hours at 37° C. The cells were washed with 2 ml O-MEM and overlaid with DMEM-10 without HEGF or hIGF1.

F. Factor Xa Protease Pretreatment of Viral Particles

Virus stocks were diluted in O-MEM to a concentration of $10^4$ pfu in 20 $\mu$l. Forty $\mu$l of diluted virus were incubated with either 0.2 μg or 2 μg FXa protease, yielding a concentration of 5 and 50 μg/ml FXa, respectively. After 1 hour incubation at 37° C., 2 ml O-MEM were added to each virus sample. Cells were infected with 1 ml virus sample per 35 mm well as described above.

G. Immunoblotting

Approximately 5000 plaque-forming units (pfu) of purified virus in 10 μl of PBS were lysed by addition of 9 μl lysis buffer (50 mM Tris [pH 8.0], 62.5 mM EDTA, 1% IGEPAL CA-630 (former NP-40), 0.4% deoxycholate). Lysed virus samples were adjusted to a volume of 20 μl with either 1 μl of PBS or with 1 μl of a 1 μg/μl FXa protease solution (New England Biolabs), incubated for 1 hour at room temperature and subjected to sodium dodecylsulfate polyacrylamide gel electrophoresis (SDS-PAGE).

The gels were blotted onto polyvinylidene difluoride membranes (Millipore). The membranes were blocked with 5% bovine serum albumin, 5% skim milk powder in TBST (10 mM Tris [pH 8.0], 150 mM NaCl, 0.05% Tween 20) for 1.5 hours at room temperature. They were then incubated with either goat anti-MV antiserum diluted 1:1000 (courtesy of S. Udem) or rabbit anti-H cytoplasmic tail antiserum diluted 1:2500 (10). After intense washing the proteins were visualized by incubation with peroxidase-conjugated goat anti-rabbit IgG (Jackson Immuno Research, 111-035-003) and peroxidase-conjugated rabbit anti-goat IgG (Calbiochem, 401504), respectively, for 1 hour at room temperature and subsequent treatment with chemiluminescent substrate (Pierce, 34080ZZ).

H. ELISA

ELISA plates were coated with 100 μl of 1 μg/ml dilutions of monoclonal anti-hEGF and anti-hIGF1 antibodies (R&D Systems, MAB236 and MAB291) for 2 hours at 37° C. and blocked by incubation with 200 μl of 1% blocking reagent (Boehringer Mannheim, 1 096 176) in TBS (10 mM Tris [pH 8.0], 150 mM NaCl). The plates were incubated with 100 μl recombinant MV diluted in 1% blocking solution overnight at 4° C.

Plates were washed three times with 200 μl TBS and bound virus was detected by incubation with 100 μl of a rabbit anti-Heterm specific antiserum diluted 1:100 in 1% blocking solution for 2 hours at 4° C. The Heterm antiserum was raised in rabbits against a peptide coresponding to the 12H-protein carboxy-terminal amino acids (NH2-CTVTREDGTNRR) (SEQ ID NO:48) linked to keyhole limpet hemocyanin through the naturally occurring cysteine (C). For detection, peroxidase-conjugated goat anti-rabbit IgG (Jackson Immuno Research, 111-035-003) diluted 1:5000 in 1% blocking solution was added for 1 hour at 4° C. and after intense washing the color reaction was performed using the POD substrate from Boehringer Mannheim (1 363 727).

I. FACScan Analysis

Expression levels of CD46, hEGFr and hIGR1r were determined by inoculating 5×105 cells in 50 μl PBS with 1:100 dilutions of monoclonal anti-CD46 clone 11/88 (courtesy of J. Schneider-Schaulies), monoclonal anti-hEGFr clone 528 (Santa Cruz, sc-120) and monoclonal anti-hIGF1r clone 33255.111 (R&D Systems, MAB391) for 1 hour on ice. After washing, the cells were incubated with a 1:50 dilution of a fluorescein-conjugated donkey anti-mouse IgG (Jackson Immuno Research, 715-095-151) for 30 min on ice, washed again, fixed in PBS containing 1% paraformaldehyde and analyzed.

To analyze virus binding, 105 CHO-hEGFr and 3T3-hIGF1r cells in a total volume of 50 μl PBS were incubated with 104 pfu of purified Edmonston or recombinant MV for 2 hours on ice. The samples were washed once in 3.5 ml PBS with 2% FCS and incubated in 50 μl PBS containing a 1:100 dilution of the monoclonal anti-H antibody 141 (Sheshberadaran, et al. Virology 128: 341–353, 1983) for 1.5 hours on ice. Subsequent incubations were performed as described above.

Figure 14A:
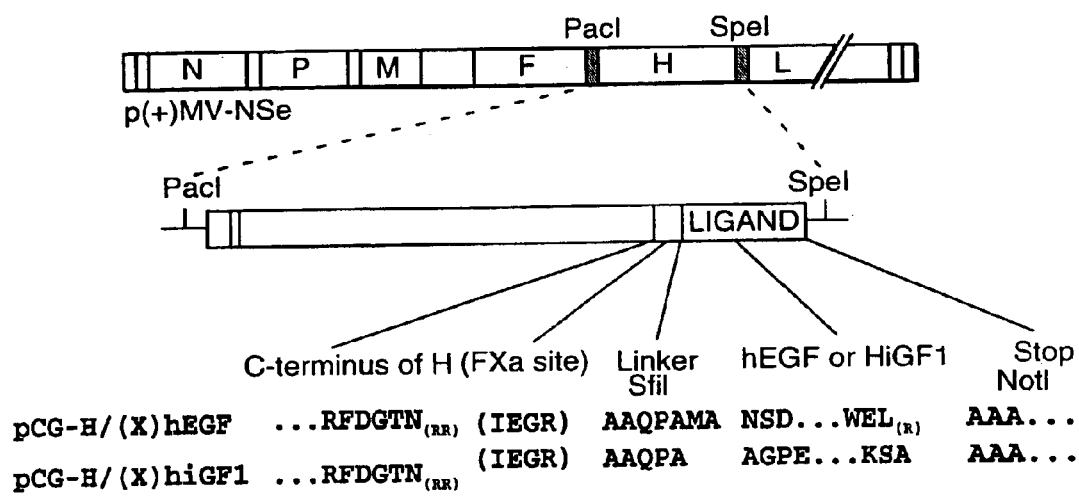

J. H Proteins Displaying a Specificity Domain Functionally Replace Standard H Protein The human epidermal growth factor (hEGF, 53 amino acids) were used to generate a hybrid protein in which the HEGF coding region ws fused in frame with the H coding region, but eliminating the last two arginine residues, to aviod the possibility of introducing an undesired furin cleavage site (H/hEGF, FIG. 14A, second line from bottom). A flexible linker region (AAQPAMA) (SEQ ID NO:49) was added between the domains to increase the probility of independent folding function. In another embodiment, the human insulin-like growth factor-1 (hIGF1, 70 amino acids) was fused to the H protein. A factor Xa protease cleavage site (IEGR; SEQ ID NO:37) was added before the linker region (H/XhEGF, FIG. 14A, second line from bottom). Hybrid H/hIGF1 and H/XhIGF1 proteins were constructed (FIG. 14A, bottom line). When the hybrid proteins were co-expressed with a MV F protein, H/hEGF and H/XhEGF retained the same level of fusogenicitiy as parental H, whereas fusogenicity of H/hIGF1 and H/XhIGF1 was reduced but remained clearly over background.

The hybrid H proteins functionally substitute for H in viral particles. In one experiment, the H gene of an infectious MV cDNA was cloned in p(+)MV-Nse (Singh, et al. J. Virol 73: 4823–4828) with genes coding for the hybrid proteins. Helper cells (Radecke, et al. supra) were transfected with those plasmids. Three to four days after transfection with p(+)MV-NSe, p(+)MV-H/hEGF and p(+)MV-H/XhEGF, and five to seven days after transfection with p(+)MV-H/hIGF and p(+)MV-H/XhIGF, syncytia were detected, indicating virus rescue. Infectivity was passaged in Vero cells, the African green monkey cell line routinely used to grow and titrate MV, and the recombinant viruses reached titers in a range similar to that of the parental virus (see below).

Figure 14D:
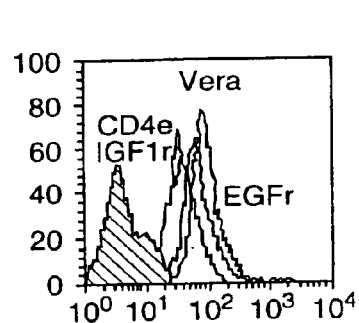
Figures 1, 14E:
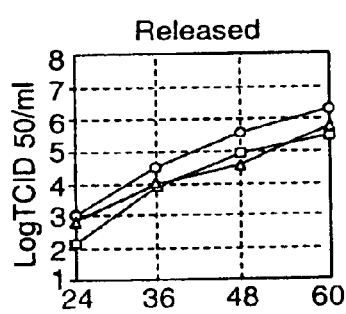
Figures 2, 14E:
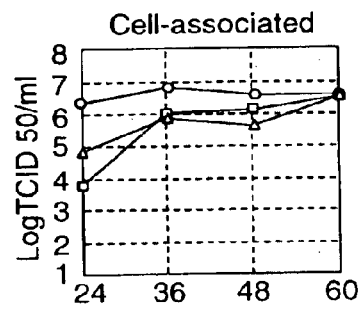
Figure 14B:
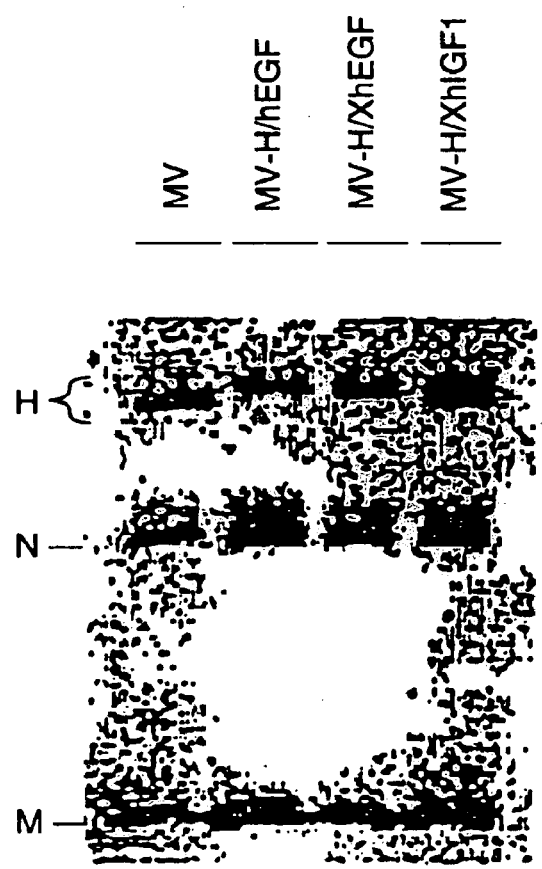

As shown in FIG. 14B, purified particles from the MV-H/hEGF, MV-H/XhEGF and MV-H/XhIGF1 viruses contained a similar amount of H protein as parental MV, but more N and M proteins. These results suggest that the hybrid H proteins are incorporated slightly less efficiently than H in particles, and that the particle to infectivity ratio of the recombinant MV is slightly higher than for the parental strain.

Figure 14C:
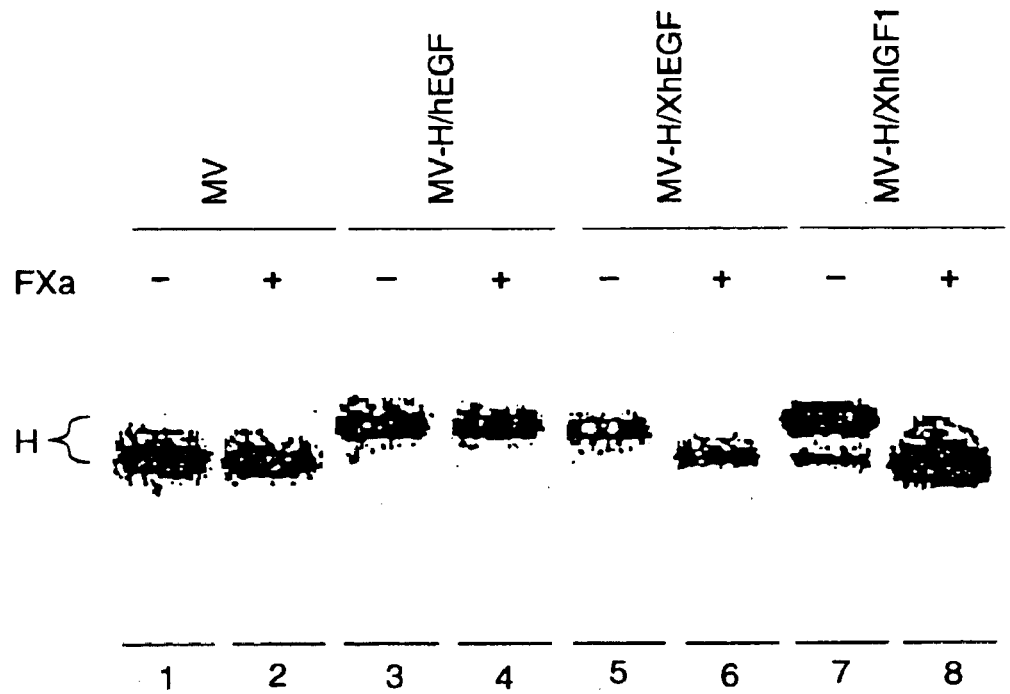

The specific proteolytic cleavage of the displayed domain from purified virus particles occurred. In FIG. 14C, it is shown that factor Xa (FXa) protease specifically cleaves off the displayed domain from the H protein of MV-H/XhEGF (lane 6) and MV-H/XhIGF1 (lane 8), but not from the control viruses MV (lane 2) and MV-H/hEGF (lane 4).

The levels of expression of CD46 and of the targeted receptors in Vero cells was determined by FACs analysis, as shown in FIG. 14D. The EGF receptor (hEGFr, continuous line), IGF receptor (hIGF1r, dotted line), and CD46 (interrupted line) were all expressed. For one step growth analysis Vero cells were infected in parallel with a MOI of 3 of either MV-H/XhEGF, MV-H/XhIGF1, or the parental MV strain. Released and cell-associated virus were harvested at 12 hour intervals and titrated on Vero cells.

Results spanning the times from 24 to 60 hours post-infection are shown in FIG. 14E. Cell-associated titers of MV-H/XhEGF (squares) rose slower than those of the parental strain (diamonds), whereas those of MV-H/XhIGF1 (triangles) were intermediate, but all viruses reached similar maximum titers of about 5×106/ml (FIG. 14E, left panel). Release of infectious virus in the supernatant followed slower kinetics, as expected and peaked at 1.7×106 for the parental strain, and at 3.5 and 6.3 times lower levels (FIG. 14E, left panel), for MV-H/XhIGF1 and MV-H/XhEGF, respectively. These results indicate that in Vero cells replication and intracellular assembly of the two recombinant viruses is slower than that of the parental strain. Nevertheless, the maximum titers of cell-associated virus are similar for all three strains. Release of the two recombinant viruses is slightly less efficient than that of parental MV.

Figures 1, 2, 15A:
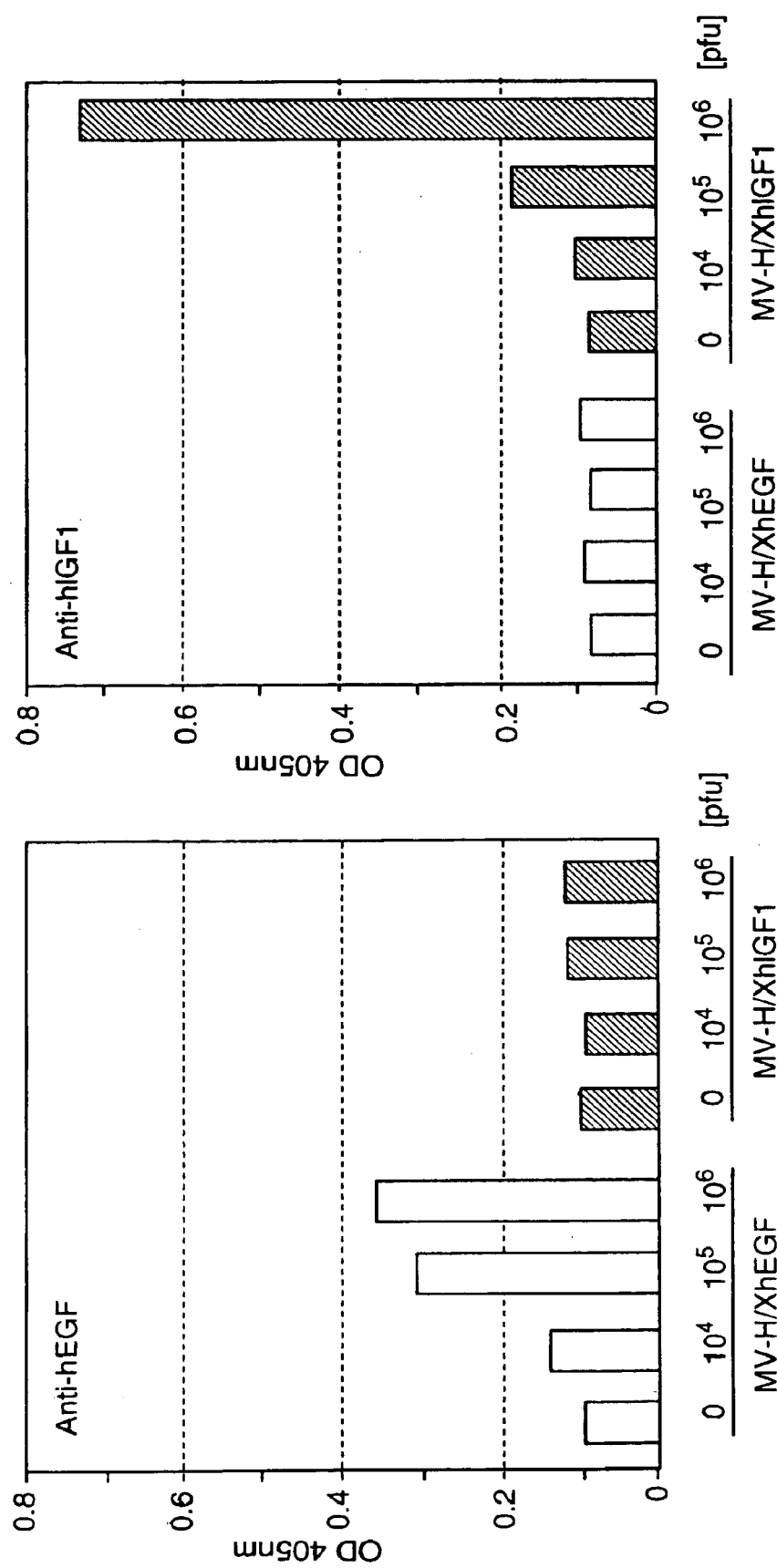

The displayed domains are accessible for binding by antibodies. FIG. 15A shows that plates coated with an anti-hEGF monoclonal antibody incubated with increasing amounts of MV-H/XhEGF retained increasing amounts of virus (left panel, white columns), whereas on plates coated with anti-hIGF1 only background retention levels were detected (right panel, white columns). The opposite was the case for the MV-H/XhIGF1 virus, which was selectively retained by the anti-hIGF1 monoclonal antibody (black columns on right panel).

K. MV Displaying a Specificity Domain Bind to, Infect, and Fuse, Rodent Cells Expressing the Cognate Receptor.

Edmonston MV-derived strains are expected to bind CD46, which is expressed on the surface of all cell types from most primates. To verify if the displayed hEGF and hIGF1 domains did confer attachment to their cognate receptors, we relied on CD46 negative rodent cells: Chinese hamster ovary cells stable expressing the HEGF receptor and mouse NIH-3T3 cells stable expressing the hIGF1 receptor 3T3-hIGF1r (Lammers, et al. EMBO 8: 1369–1375).

Figures 4, 15B:
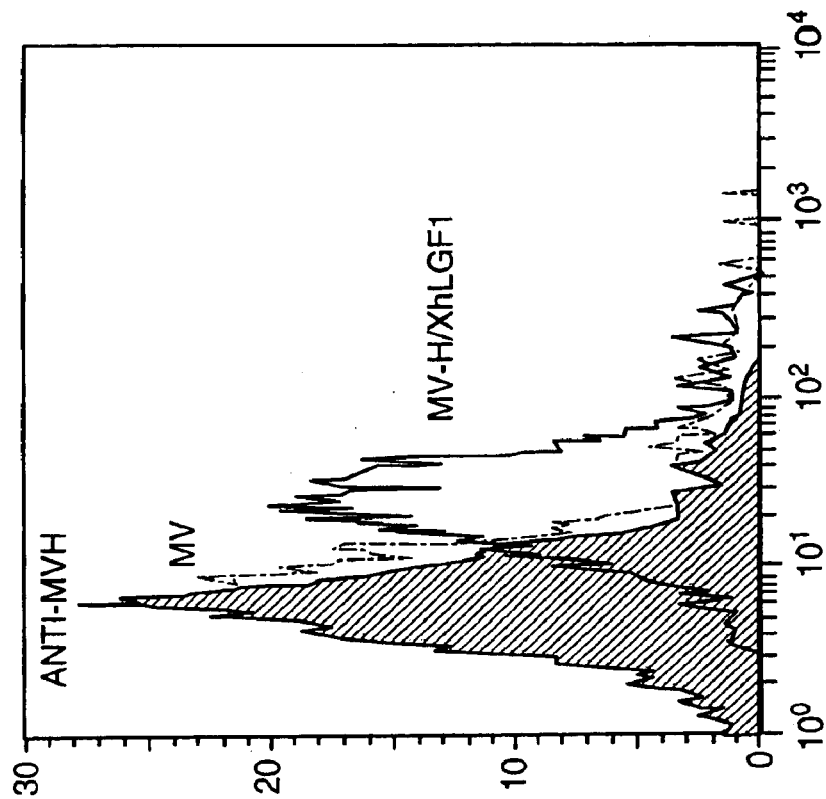
Figures 3, 15B:
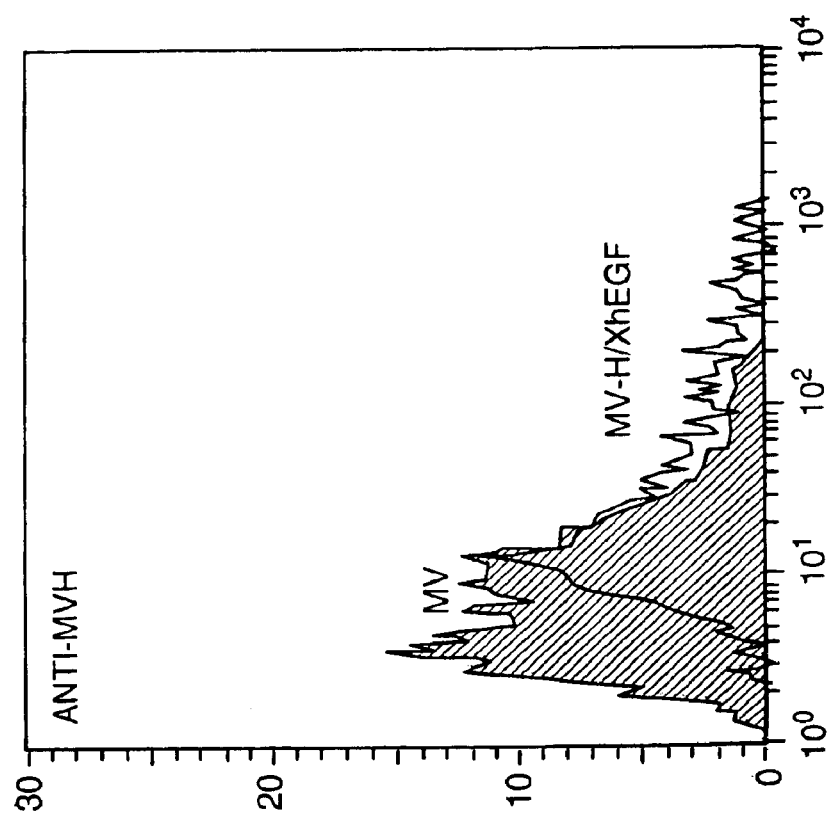
Figure 16:
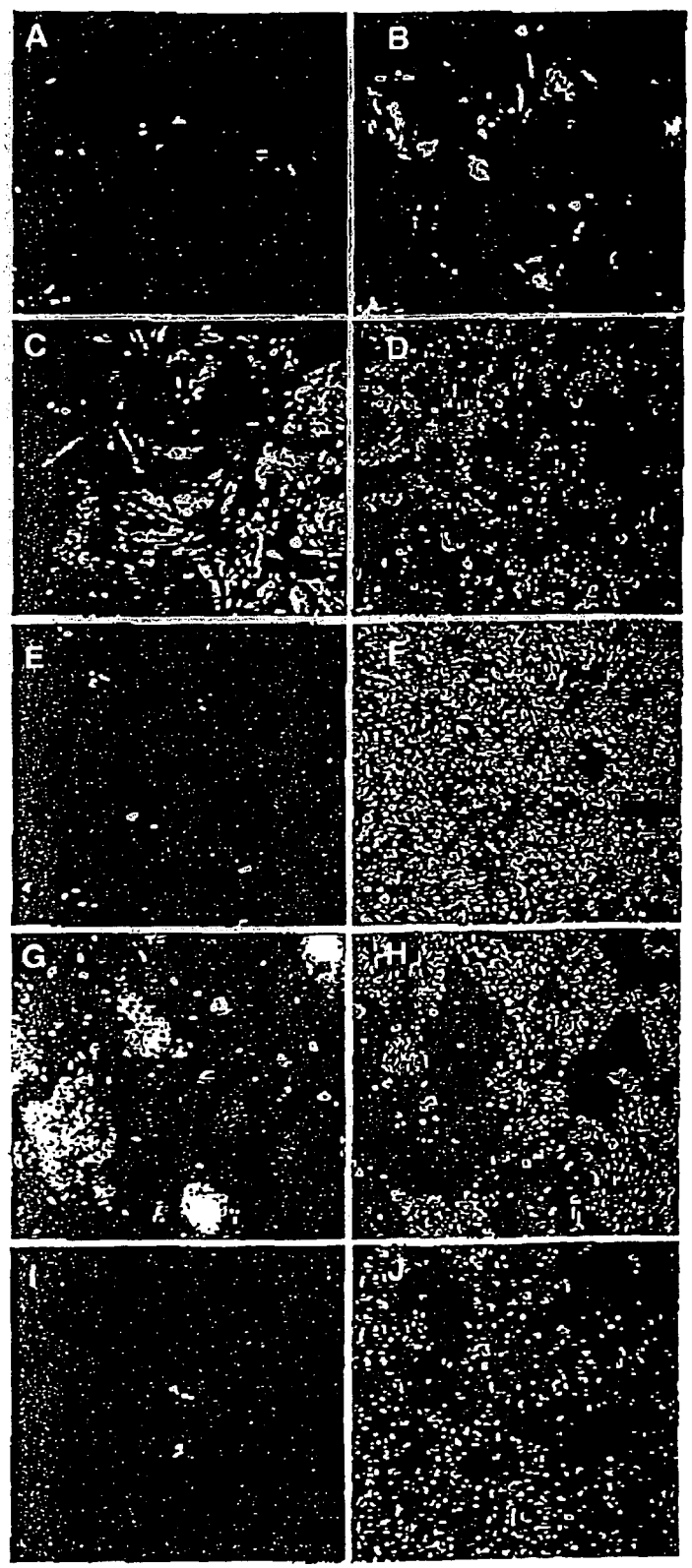
Figure 17:
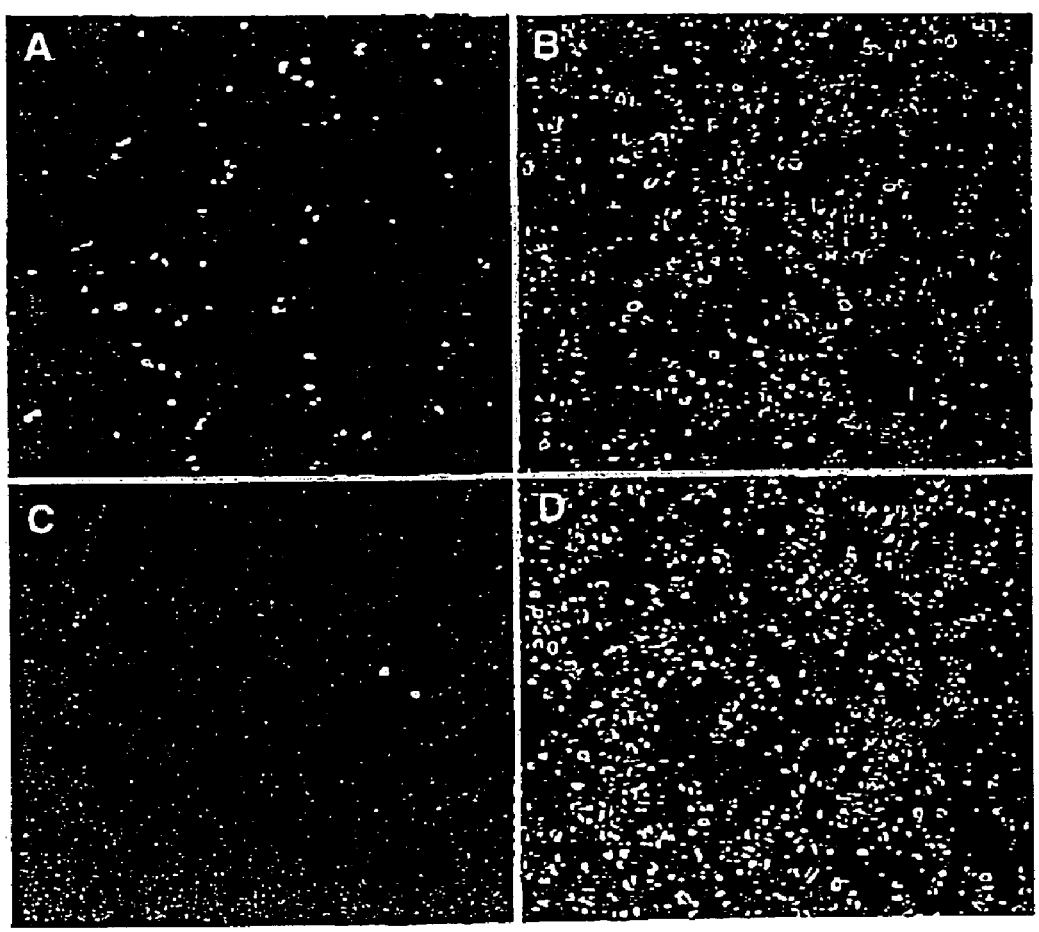

FIG. 15B presents a fluorescence-activated cell sorter (FACS) analysis confirming that CHO-hEGFr cells (upper left panel) and 3T3-hIGF1r (upper right panel) express the corresponding human protein on their surface. When these cells were incubated with MV-H/XhEGF (lower left panel) or MV-H/XhIGF1 (lower right panel), respectively, and virus binding was detected with an anti-H monoclonal antibody (thick line), a shift in the number of strongly fluorescent cells from background antibody binding (gray area) and from binding of control MV (thin lines) was shown in both cell lines.

To detect viral gene expression early after entry, viruses expressing high levels of the enhanced green fluorescent protein (eGFP) were constructed (5 Yang, et al. NAR 24: 4592–4593, 1996). For this, a MV genomic plasmid containing an eGFP transcription unit (Duprex, et al. supra) was combined with p(+)MV-H/XhEGF and p(+)MV-H/XhIGF1. The new viruses were rescued and named MVgreen-H/XhEGF and MVgreen-H/XhIGF1.

FIGS. 16A–J present three time points (24, 48 and 72 hours post infection, p.i.) of an infection of CHO-hEGFr cells with MVgreen-H/XhEGF at a multiplicity of infection (m.o.i.) of 1. At 24 hours p.i. (panel A) fluorescence was detected in single cells; at 48 hours p.i. (panel B) a large fraction of the cells showed a strong signal and, remarkably, several fused cells were registered; at 72 hours p.i. the majority of the cells had fused in large syncytia (panel D) which were fluorescent (panel C). In controls CHO-hEGFr cells infected with MVgreen no fluorescence was detected 24 hours p.i. and few positive cells 72 hours p.i. (panel E). The same was true for another negative control, CHO cells infected with MVgreen-H/XhEGF (panel I shown 72 hours after infection).

The few small syncytia detected in MVgreen infected CHO-hEGFr cells and MVgreen-H/hEGF infected CHO cells (panel F and J) were not fluorescent (panels E and 1, respectively) and thus were due to spontaneous fusion at high cell density. On the other hand CHO-hEGFr.tr cells, expressing a hEGF receptor with a truncated cytoplasmic tail supported efficient MVgreen-H/XhEGF infection, which resulted in cell fusion (panels G and H, shown 72 hours after infection). Thus, CHO cells expressing the human EGF receptor, or a mutant receptor without the cytoplasmic tail, support efficient, CD46-independent cell entry of MVgreen-H/XhEGF, indicating that internalization or intracellular signaling do not affect MV entry. Strikingly, in these cells the MV infection results in extensive syncytia formation.

FIGS. 17A–D present 3T3-hIGF1r cells 24 hours after infection with a MOI of 3 of MVgreen-H/XhIGF1 (panels A and B) and MVgreen (panels C and D), respectively. Many cells infected with MVgreen-H/XhIGF1 were strongly fluorescent (panel A), whereas only rare fluorescent cells were detected after MVgreen infection (panel C). To gain some information on the relative efficiency of entry of MVgreen-H/XhIGF1 and MVgreen in 3T3-hIGF1r cells, these cells were infected with either one of the viruses at a MOI of 3, 0.3 or 0.03. In a 35 mm dish, 735 positive cells infected with MVgreen-H/XhIGF1 at an MOI of 0.03 were counted, and 87 positive cells infected with MVgreen at an MOI of 3. Thus, about 1000 times more infectious particles of MVgreen than of MVgreen-H/XhIGF1 were needed to elicit detectable eGFP expression in the same number of 3T3-hIGF1r cells. Even late in infection of 3T3-hIGF1r cells with MVgreen-H/XhIGF 1 fusion was limited, in line with the limited fusion of primate Vero cells (data not shown).

Figures 1, 18A:
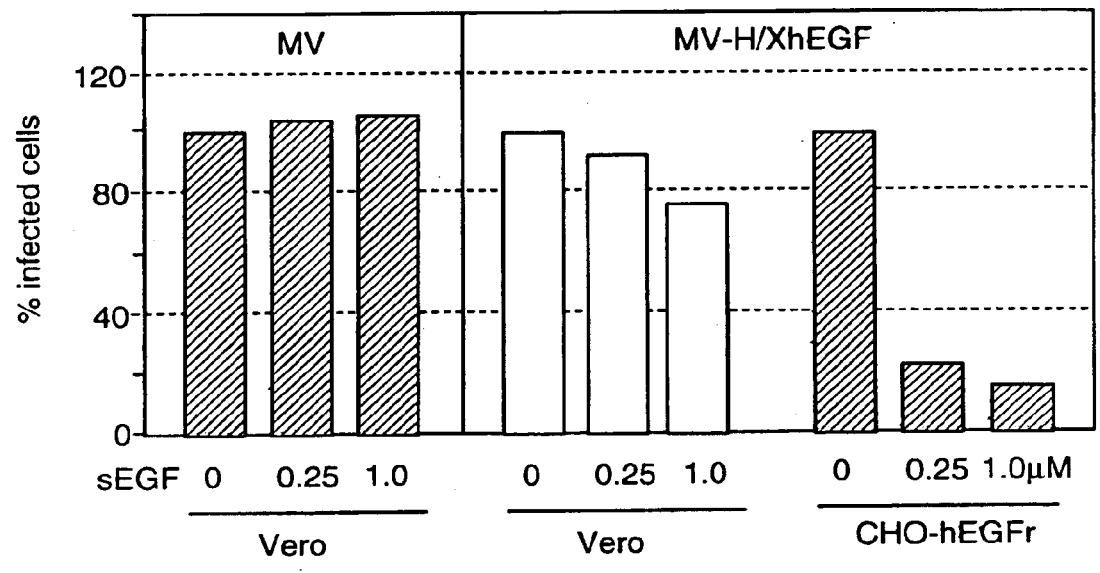
Figures 2, 18A:
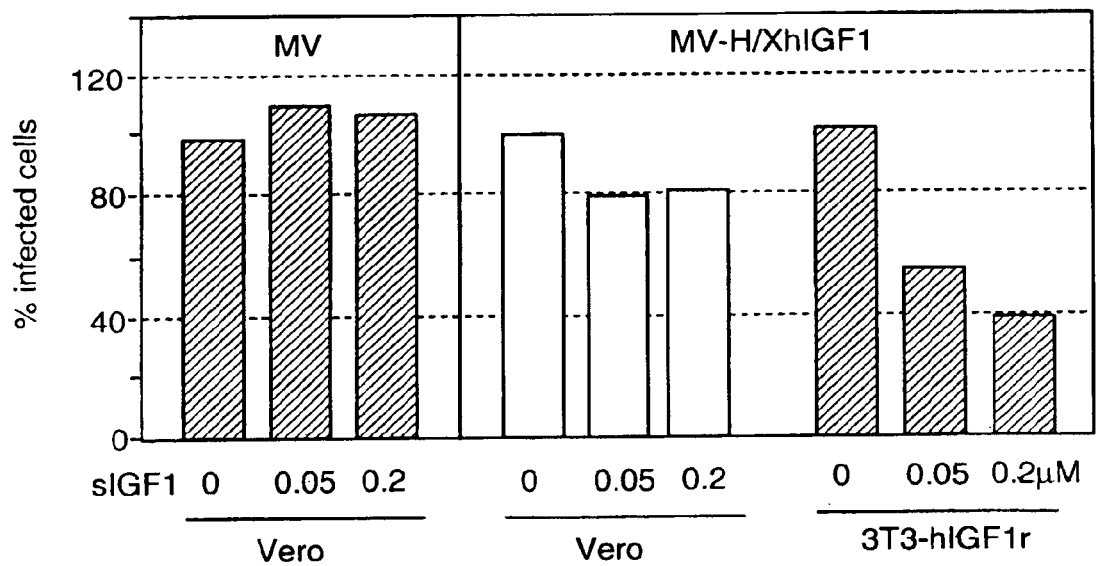

The interaction of the displayed domains with their receptor mediates virus entry. As shown in FIG. 18A, top panel, black columns, the addition of 0.25 or 1 $\mu$M soluble human EGF to the medium of CHO-hEGFr cells reduced the number of cells infected with MVgreen-H/XhEGF approximately 5–6 times. There was no inhibition of the MVgreen infection of Vero cells by 1 $\mu$M soluble EGF (FIG. 18A, top panel, gray columns), but interestingly there was a small but reproducible effect of soluble EGF in inhibiting the MVgreen-H/XhEGF infection of those cells (FIG. 18A, top panel, white columns). Analogously, soluble human IGF interfered selectively with the infection of MVgreen-H/XhIGF1, more strongly on 3T3-hIGFr cells than on Vero cells (FIG. 18A, lower panel). These results indicated that entry of MVgreen-H/XhEGF or MVgreen-H/XhIGF1 could be competed by the addition of a soluble form of HEGF or hIGF1, respectively to the medium.

Figure 18B:
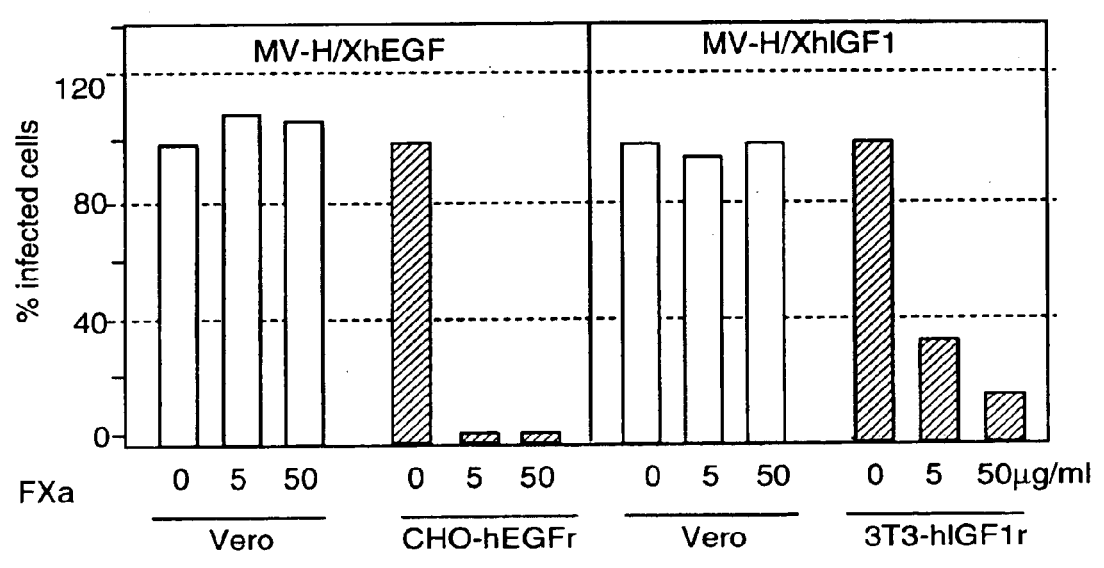

When MV-H/XhEGF particles were treated with 5 or 50 $\mu$g/ml of factor Xa protease for one hour, the number of green fluorescent CHO-hEGFr cells diminished by almost two orders of magnitude (FIG. 18B, left panel, black column), whereas factor Xa treatment did not significantly change the infectivity of these particles on Vero cells (FIG. 18B, left panel, white columns). Analogously, proteolytic cleavage of MV-H/XhIGF1 virus particles with factor Xa protease resulted in loss of more than 80% of the infectivity selectively in 3T3-hIGF1r cells (FIG. 18B, right panel, compare black and white columns). Thus, by two different approaches, competition with a soluble form of the displayed domain, and proteolytic cleavage of that domain from viral particles, it was confirmed that entry of recombinant MV in rodent cells depends on the interaction of the specificity domain with the cognate receptor.

Other embodiments will be evident to those of skill in the art. It should be understood that the foregoing detailed description is provided for clarity only and is merely exemplary. The spirit and scope of the present invention are not limited to the above examples, but are encompassed by the following claims.

What is claimed is:

1. A method of monitoring gene expression of virally encoded nucleic acid from virus infected cells within a patient, said method comprising:

(a) administering a measles virus to said patient, wherein said measles virus comprises a nucleic acid sequence encoding a heterologous polypeptide, wherein said nucleic acid sequence is upstream of a nucleic acid encoding a viral polypeptide, and wherein said heterologous polypeptide is released from infected cells into a biological fluid of said patient when expressed, and (b) detecting the amount of said heterologous polypeptide in said biological fluid, thereby providing an indication of the amount of said gene expression.

2. The method of claim 1, wherein said heterologous polypeptide is biologically inactive in said patient.

3. The method of claim 1, wherein the molecular weight of said heterologous polypeptide is below 10 kilodaltons.

4. The method of claim 1, wherein said heterologous polypeptide is a tumor antigen.

5. The method of claim 1, wherein said heterologous polypeptide is a carcinoembryonic antigen.

6. The method of claim 1, wherein said heterologous polypeptide is a beta subunit of human chorionic gonadotrophin.

7. The method of claim 1, wherein said nucleic acid sequence encodes a fusion protein, wherein said fusion protein comprises said heterologous polypeptide fused to an endogenous polypeptide.

8. The method of claim 7, wherein said endogenous polypeptide is an H protein.

9. The method of claim 7, wherein said fusion protein comprises an amino acid linker sequence between said heterologous polypeptide and said endogenous polypeptide, and wherein said amino acid linker sequence comprises a protease cleavage site.

10. The method of claim 9, wherein said protease cleavage site is a furin cleavage site.

11. The method of claim 1, wherein said measles virus is replication-competent.

12. A measles virus comprising a nucleic acid sequence encoding a heterologous polypeptide, wherein said measles virus infects cells of a patient when administered to said patient, wherein said nucleic acid sequence is upstream of a nucleic acid encoding a viral polypeptide, and wherein said heterologous polypeptide is released from said infected cells into a biological fluid of said organism when expressed, said released heterologous polypeptide being detectable in said biological fluid, and wherein said heterologous polypeptide is biologically inactive in said patient.

13. The measles virus of claim 12, wherein the molecular weight of said heterologous polypeptide is below 10 kilodaltons.

14. The measles virus of claim 12, wherein said heterologous polypeptide is a tumor antigen.

15. The measles virus of claim 12, wherein said heterologous polypeptide is a carcinoembryonic antigen.

16. The measles virus of claim 12, wherein said heterologous polypeptide is a beta subunit of human chorionic gonadotrophin.

17. The measles virus of claim 12, wherein said nucleic acid sequence encodes a fusion protein, wherein said fusion protein comprises said heterologous polypeptide fused to an endogenous polypeptide.

18. The measles virus of claim 17, wherein said endogenous polypeptide is an H protein.

19. The measles virus of claim 17, wherein said fusion protein comprises an amino acid linker sequence between said heterologous polypeptide and said endogenous polypeptide, and wherein said amino acid linker sequence comprises a protease cleavage site.

20. The measles virus of claim 19, wherein said protease cleavage site is a furin cleavage site.

21. The measles virus of claim 12, wherein said measles virus is replication-competent.

* * * * *

UNITED STATES PATENT AND TRADEMARK OFFICE
CERTIFICATE OF CORRECTION

| | |
|---|---|
| PATENT NO. | : 6,896,881 B1 |
| APPLICATION NO. | : 09/667947 |
| DATED | : May 24, 2005 |
| INVENTOR(S) | : Kah-Whye Peng and Stephen J. Russell |

It is certified that error appears in the above-identified patent and that said Letters Patent is hereby corrected as shown below:

Title Page (Page 2), References Cited, Other Publications, delete Bennett et al., Kirn et al., Lorence et al., and Sinkovics et al. references are all missing titles of the articles;

Insert:
Lorence, et al., Complete Regression of Human Neuroblastoma Xenografts in Athymic Mice After Local Newcastle Disease Virus Therapy, Journal of the National Cancer Institute, 17 August 1994, Vol. 86, No. 16, pages 1228-1233.

Title Page (Page 2), References Cited, Other Publications, Galanis et al. reference, please delete "Glycorproteins" and insert --Glycoproteins--therefor;

Title Page (Page 3), References Cited, Other Publications, Mitus et al. reference, please delete "Childred" and insert --Children--therefor;

Title Page (Page 3), References Cited, Other Publications, Nemunaitis et al. reference, please delete "173" and insert --375--therefor;

Title Page (Page 3), References Cited, Other Publications, Ohara et al. reference, please delete "Determintion" and insert --Determination--therefor;

Title Page (Page 3), References Cited, Other Publications, Peavear et al. reference, please delete "Peavear" and insert --Pevear--therefor;

Title Page (Page 3), References Cited, Other Publications, Russell et al. reference, please delete "Glycroproteins" and insert --Glycoproteins--therefor;

Title Page (Page 3), References Cited, Other Publications, Schattner et al. reference, please delete "Cell," and insert --Cell.--therefor;

Title Page (Page 3), References Cited, Other Publications, Segni and Curro reference, please delete "Malatti" and insert --Malattie--therefor;

Title Page (Page 4), References Cited, Other Publications, Thornberry et al. reference, please delete "Specificies" and insert --Specificities--therefor;

UNITED STATES PATENT AND TRADEMARK OFFICE
CERTIFICATE OF CORRECTION

PATENT NO. : 6,896,881 B1
APPLICATION NO. : 09/667947
DATED : May 24, 2005
INVENTOR(S) : Kah-Whye Peng, Stephen J. Russell, and It is certified that error appears in the above-identified patent and that said Letters Patent is hereby corrected as shown below:

Title Page, References Cited, Other Publications, please insert --

Schirrmacher et al., "Human tumor cell modification by virus infection: and efficient and safe way to produce cancer vaccine with pleiotropic immune stimulatory properties when using Newcastle disease virus," Gene Ther., 1999, 6:63-73--.

Signed and Sealed this

First Day of August, 2006

JON W. DUDAS
*Director of the United States Patent and Trademark Office*

SEQUENCE LISTING

<160> NUMBER OF SEQ ID NOS: 49

<210> SEQ ID NO 1
<211> LENGTH: 4
<212> TYPE: PRT
<213> ORGANISM: Artificial Sequence
<220> FEATURE:
<223> OTHER INFORMATION: Factor Xa cleavage site

<400> SEQUENCE: 1

Ile Glu Gly Arg
 1

<210> SEQ ID NO 2
<211> LENGTH: 4
<212> TYPE: PRT
<213> ORGANISM: Artificial Sequence
<220> FEATURE:
<223> OTHER INFORMATION: Furin cleavage site
<220> FEATURE:
<221> NAME/KEY: VARIANT
<222> LOCATION: 2
<223> OTHER INFORMATION: Xaa = Any 20 amino acids

<400> SEQUENCE: 2

Arg Xaa Lys Arg
 1

<210> SEQ ID NO 3
<211> LENGTH: 6
<212> TYPE: PRT
<213> ORGANISM: Artificial Sequence
<220> FEATURE:
<223> OTHER INFORMATION: MMP cleavage site

<400> SEQUENCE: 3

Pro Leu Gly Leu Trp Ala
 1               5

<210> SEQ ID NO 4
<211> LENGTH: 6
<212> TYPE: PRT
<213> ORGANISM: Artificial Sequence
<220> FEATURE:
<223> OTHER INFORMATION: Caspase-1 cleavage site

<400> SEQUENCE: 4

Tyr Glu Val Asp Gly Trp
 1               5

<210> SEQ ID NO 5
<211> LENGTH: 7
<212> TYPE: PRT
<213> ORGANISM: Artificial Sequence
<220> FEATURE:
<223> OTHER INFORMATION: Caspase-2 cleavage site

<400> SEQUENCE: 5

Val Asp Val Ala Asp Gly Trp
 1               5

<210> SEQ ID NO 6
<211> LENGTH: 7
<212> TYPE: PRT
<213> ORGANISM: Artificial Sequence
<220> FEATURE:

<223> OTHER INFORMATION: Caspase-3 cleavage site

<400> SEQUENCE: 6

Val Asp Gln Met Asp Gly Trp
 1               5

<210> SEQ ID NO 7
<211> LENGTH: 6
<212> TYPE: PRT
<213> ORGANISM: Artificial Sequence
<220> FEATURE:
<223> OTHER INFORMATION: Caspase-4 cleavage site

<400> SEQUENCE: 7

Leu Glu Val Asp Gly Trp
 1               5

<210> SEQ ID NO 8
<211> LENGTH: 6
<212> TYPE: PRT
<213> ORGANISM: Artificial Sequence
<220> FEATURE:
<223> OTHER INFORMATION: Caspase-6 cleavage site

<400> SEQUENCE: 8

Val Gln Val Asp Gly Trp
 1               5

<210> SEQ ID NO 9
<211> LENGTH: 7
<212> TYPE: PRT
<213> ORGANISM: Artificial Sequence
<220> FEATURE:
<223> OTHER INFORMATION: Caspase-7 cleavage site

<400> SEQUENCE: 9

Val Asp Gln Val Asp Gly Trp
 1               5

<210> SEQ ID NO 10
<211> LENGTH: 4
<212> TYPE: PRT
<213> ORGANISM: Artificial Sequence
<220> FEATURE:
<223> OTHER INFORMATION: Proprotein convertase cleavage site

<400> SEQUENCE: 10

Arg Gly Leu Thr
 1

<210> SEQ ID NO 11
<211> LENGTH: 17
<212> TYPE: PRT
<213> ORGANISM: Artificial Sequence
<220> FEATURE:
<223> OTHER INFORMATION: FMDV protease 2A cleavage site

<400> SEQUENCE: 11

Asn Phe Asp Leu Leu Lys Leu Ala Gly Asp Val Glu Ser Asn Pro Gly
 1               5                  10                  15

Pro

<210> SEQ ID NO 12
<211> LENGTH: 34
<212> TYPE: PRT
<213> ORGANISM: Paramyxoviridae

```
<220> FEATURE:
<223> OTHER INFORMATION: H protein cytoplasmic tail

<400> SEQUENCE: 12

Met Ser Pro Gln Arg Asp Arg Ile Asn Ala Phe Tyr Lys Asp Asn Pro
 1               5                   10                  15

His Pro Lys Gly Ser Arg Ile Val Ile Asn Arg Glu His Leu Met Ile
            20                  25                  30

Asp Arg

<210> SEQ ID NO 13
<211> LENGTH: 33
<212> TYPE: PRT
<213> ORGANISM: Paramyxoviridae
<220> FEATURE:
<223> OTHER INFORMATION: F protein cytoplasmic tail

<400> SEQUENCE: 13

Arg Gly Arg Cys Asn Lys Lys Gly Glu Gln Val Gly Met Ser Arg Pro
 1               5                   10                  15

Gly Leu Lys Pro Asp Leu Thr Gly Thr Ser Lys Ser Tyr Val Arg Ser
            20                  25                  30

Leu

<210> SEQ ID NO 14
<211> LENGTH: 5
<212> TYPE: PRT
<213> ORGANISM: Artificial Sequence
<220> FEATURE:
<223> OTHER INFORMATION: Furin cleavage site

<400> SEQUENCE: 14

Arg Arg His Lys Arg
 1               5

<210> SEQ ID NO 15
<211> LENGTH: 4
<212> TYPE: PRT
<213> ORGANISM: Artificial Sequence
<220> FEATURE:
<223> OTHER INFORMATION: Furin cleavage site

<400> SEQUENCE: 15

Arg His Lys Arg
 1

<210> SEQ ID NO 16
<211> LENGTH: 47
<212> TYPE: DNA
<213> ORGANISM: Artificial Sequence
<220> FEATURE:
<223> OTHER INFORMATION: Primer

<400> SEQUENCE: 16
ttttcctttt gcggccgctt tcatcaacgc ttctgcaggg acccctc                47

<210> SEQ ID NO 17
<211> LENGTH: 56
<212> TYPE: DNA
<213> ORGANISM: Artificial Sequence
<220> FEATURE:
<223> OTHER INFORMATION: Primer

<400> SEQUENCE: 17
```

```
gtccatgcgg cccagccggc ccgattaaag agagaggcag aggacctgca ggtggg          56
```

<210> SEQ ID NO 18
<211> LENGTH: 18
<212> TYPE: PRT
<213> ORGANISM: Artificial Sequence
<220> FEATURE:
<223> OTHER INFORMATION: Amino acid sequence coded for by primer

<400> SEQUENCE: 18

Val His Ala Ala Gln Pro Ala Arg Leu Lys Arg Glu Ala Glu Asp Leu
 1               5                  10                  15

Gln Val

<210> SEQ ID NO 19
<211> LENGTH: 50
<212> TYPE: DNA
<213> ORGANISM: Artificial Sequence
<220> FEATURE:
<223> OTHER INFORMATION: Primer

<400> SEQUENCE: 19

```
ttttcctttt gcggccgctt tcatcatcaa cgcttctgca gggacccctc               50
```

<210> SEQ ID NO 20
<211> LENGTH: 59
<212> TYPE: DNA
<213> ORGANISM: Artificial Sequence
<220> FEATURE:
<223> OTHER INFORMATION: Primer

<400> SEQUENCE: 20

```
gtccatgcgg cccagccggc cggtggaggc ggttcagagg cagaggacct gcaggtggg     59
```

<210> SEQ ID NO 21
<211> LENGTH: 19
<212> TYPE: PRT
<213> ORGANISM: Artificial Sequence
<220> FEATURE:
<223> OTHER INFORMATION: Amino acid sequence coded for by primer

<400> SEQUENCE: 21

Val His Ala Ala Gln Pro Ala Gly Gly Gly Gly Ser Glu Ala Glu Asp
 1               5                  10                  15

Leu Gln Val

<210> SEQ ID NO 22
<211> LENGTH: 16
<212> TYPE: PRT
<213> ORGANISM: Paramyxoviridae
<220> FEATURE:
<223> OTHER INFORMATION: F protein cytoplasmic tail

<400> SEQUENCE: 22

Arg Gly Arg Cys Asn Lys Lys Gly Glu Gln Gly Met Ser Arg Pro Gly
1 5 10 15

<210> SEQ ID NO 23
<211> LENGTH: 9
<212> TYPE: PRT
<213> ORGANISM: Paramyxoviridae
<220> FEATURE:
<223> OTHER INFORMATION: Cytoplasmic tail of Fc(24 mutant

<400> SEQUENCE: 23

```
Arg Gly Arg Cys Asn Lys Lys Gly Glu
  1               5
```

<210> SEQ ID NO 24
<211> LENGTH: 26
<212> TYPE: DNA
<213> ORGANISM: Artificial Sequence
<220> FEATURE:
<223> OTHER INFORMATION: Primer

<400> SEQUENCE: 24
aaaactgcag actcaaaggt caatgc                                26

<210> SEQ ID NO 25
<211> LENGTH: 30
<212> TYPE: DNA
<213> ORGANISM: Artificial Sequence
<220> FEATURE:
<223> OTHER INFORMATION: Primer

<400> SEQUENCE: 25
cccttaatta atatacagat ctcaacggat                            30

<210> SEQ ID NO 26
<211> LENGTH: 31
<212> TYPE: DNA
<213> ORGANISM: Artificial Sequence
<220> FEATURE:
<223> OTHER INFORMATION: Primer

<400> SEQUENCE: 26
ccatcgataa tggccttcta caaagataac c                          31

<210> SEQ ID NO 27
<211> LENGTH: 33
<212> TYPE: DNA
<213> ORGANISM: Artificial Sequence
<220> FEATURE:
<223> OTHER INFORMATION: Primer

<400> SEQUENCE: 27
ccatcgataa tgagccatcc caagggaagt agg                        33

<210> SEQ ID NO 28
<211> LENGTH: 33
<212> TYPE: DNA
<213> ORGANISM: Artificial Sequence
<220> FEATURE:
<223> OTHER INFORMATION: Primer

<400> SEQUENCE: 28
ccatcgataa tgaacagaga acatcttatg att                        33

<210> SEQ ID NO 29
<211> LENGTH: 29
<212> TYPE: DNA
<213> ORGANISM: Artificial Sequence
<220> FEATURE:
<223> OTHER INFORMATION: Primer

<400> SEQUENCE: 29
ccatcgataa tcatggatgg tgatagggg                             29

<210> SEQ ID NO 30
<211> LENGTH: 31
<212> TYPE: DNA

-continued

```
<213> ORGANISM: Artificial Sequence
<220> FEATURE:
<223> OTHER INFORMATION: Primer

<400> SEQUENCE: 30
gcaaaacata agggtgtca actttacttg a                                    31

<210> SEQ ID NO 31
<211> LENGTH: 23
<212> TYPE: DNA
<213> ORGANISM: Artificial Sequence
<220> FEATURE:
<223> OTHER INFORMATION: Primer

<400> SEQUENCE: 31
gacacccctt atgttttgct ggc                                            23

<210> SEQ ID NO 32
<211> LENGTH: 32
<212> TYPE: DNA
<213> ORGANISM: Artificial Sequence
<220> FEATURE:
<223> OTHER INFORMATION: Primer

<400> SEQUENCE: 32
gcttcaagta ggaaccacaa cagatttgcg gg                                  32

<210> SEQ ID NO 33
<211> LENGTH: 32
<212> TYPE: DNA
<213> ORGANISM: Artificial Sequence
<220> FEATURE:
<223> OTHER INFORMATION: Primer

<400> SEQUENCE: 33
cccgcaaatc tgttgtggtt cctacttgaa gc                                  32

<210> SEQ ID NO 34
<211> LENGTH: 7
<212> TYPE: PRT
<213> ORGANISM: Artificial Sequence
<220> FEATURE:
<223> OTHER INFORMATION: Furin cleavage site
<220> FEATURE:
<223> OTHER INFORMATION: Primer

<400> SEQUENCE: 34

Arg His Lys Arg Phe Ala Gly
  1               5

<210> SEQ ID NO 35
<211> LENGTH: 7
<212> TYPE: PRT
<213> ORGANISM: Artificial Sequence
<220> FEATURE:
<223> OTHER INFORMATION: Furin cleavage site
<220> FEATURE:
<221> NAME/KEY: VARIANT
<222> LOCATION: 5
<223> OTHER INFORMATION: Xaa = Phe or Leu
<220> FEATURE:
<221> NAME/KEY: VARIANT
<222> LOCATION: 6
<223> OTHER INFORMATION: Xaa = Ala or Ile
<220> FEATURE:
<221> NAME/KEY: VARIANT
<222> LOCATION: 7
<223> OTHER INFORMATION: Xaa = Gly or Ala
```

```
<400> SEQUENCE: 35

Arg His Lys Arg Xaa Xaa Xaa
 1               5

<210> SEQ ID NO 36
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: VARIANT
<222> LOCATION: 1
<223> OTHER INFORMATION: n = A, T, C, or G
<220> FEATURE:
<221> NAME/KEY: VARIANT
<222> LOCATION: 2
<223> OTHER INFORMATION: n = A, C, or T
<220> FEATURE:
<221> NAME/KEY: VARIANT
<222> LOCATION: 3
<223> OTHER INFORMATION: n = T or C
<220> FEATURE:
<221> NAME/KEY: VARIANT
<222> LOCATION: 4
<223> OTHER INFORMATION: n = A, T, C, or G
<220> FEATURE:
<221> NAME/KEY: VARIANT
<222> LOCATION: 5
<223> OTHER INFORMATION: n = A, C, or T
<220> FEATURE:
<221> NAME/KEY: VARIANT
<222> LOCATION: 6
<223> OTHER INFORMATION: n = T or C
<220> FEATURE:
<221> NAME/KEY: VARIANT
<222> LOCATION: 7
<223> OTHER INFORMATION: n = A, T, C, or G
<220> FEATURE:
<221> NAME/KEY: VARIANT
<222> LOCATION: 8
<223> OTHER INFORMATION: n = A, C, or T
<220> FEATURE:
<221> NAME/KEY: VARIANT
<222> LOCATION: 9
<223> OTHER INFORMATION: n = T or C
<220> FEATURE:
<221> NAME/KEY: VARIANT
<222> LOCATION: 10, 11, 12
<223> OTHER INFORMATION: n = A, T, C, or G
<220> FEATURE:
<221> NAME/KEY: VARIANT
<222> LOCATION: 15
<223> OTHER INFORMATION: n = A or C
<220> FEATURE:
<221> NAME/KEY: VARIANT
<222> LOCATION: 16
<223> OTHER INFORMATION: n = A or G
<220> FEATURE:
<221> NAME/KEY: VARIANT
<222> LOCATION: 17
<223> OTHER INFORMATION: n = C or T
<220> FEATURE:
<221> NAME/KEY: VARIANT
<222> LOCATION: 20
<223> OTHER INFORMATION: n = G or C

<400> SEQUENCE: 36 nnnnnnnnnnnnttnnnagnt                                             21

<210> SEQ ID NO 37
<211> LENGTH: 4
<212> TYPE: PRT
<213> ORGANISM: Artificial Sequence
<220> FEATURE:
```

-continued

<223> OTHER INFORMATION: Factor Xa cleavage site

<400> SEQUENCE: 37

Ile Glu Gly Arg
1

<210> SEQ ID NO 38
<211> LENGTH: 17
<212> TYPE: DNA
<213> ORGANISM: Artificial Sequence
<220> FEATURE:
<223> OTHER INFORMATION: Primer

<400> SEQUENCE: 38
gcgcgctggc ccaggtg                                                17

<210> SEQ ID NO 39
<211> LENGTH: 16
<212> TYPE: DNA
<213> ORGANISM: Artificial Sequence
<220> FEATURE:
<223> OTHER INFORMATION: Primer

<400> SEQUENCE: 39
tgcggccgcc cgtttc                                                 16

<210> SEQ ID NO 40
<211> LENGTH: 8
<212> TYPE: PRT
<213> ORGANISM: Artificial Sequence
<220> FEATURE:
<223> OTHER INFORMATION: Epitope tag

<400> SEQUENCE: 40

Asp Tyr Lys Asp Asp Asp Asp Lys
1               5

<210> SEQ ID NO 41
<211> LENGTH: 11
<212> TYPE: PRT
<213> ORGANISM: Artificial Sequence
<220> FEATURE:
<223> OTHER INFORMATION: Sequence of linker region

<400> SEQUENCE: 41

Ile Glu Gly Arg Ala Ala Gln Pro Ala Met Ala
1               5                   10

<210> SEQ ID NO 42
<211> LENGTH: 33
<212> TYPE: DNA
<213> ORGANISM: Artificial Sequence
<220> FEATURE:
<223> OTHER INFORMATION: Fragment

<400> SEQUENCE: 42
atcgagggaa gggcggccca gccggccatg gcc                              33

<210> SEQ ID NO 43
<211> LENGTH: 11
<212> TYPE: DNA
<213> ORGANISM: Artificial Sequence
<220> FEATURE:
<223> OTHER INFORMATION: Synthetic

<400> SEQUENCE: 43
tagtaactag t                                                    11

<210> SEQ ID NO 44
<211> LENGTH: 59
<212> TYPE: DNA
<213> ORGANISM: Artificial Sequence
<220> FEATURE:
<223> OTHER INFORMATION: Synthetic

<400> SEQUENCE: 44
ccgggaagat ggaaccaatg cggcccagcc ggcctcaggt tcagcggccg catagtaga    59

<210> SEQ ID NO 45
<211> LENGTH: 59
<212> TYPE: DNA
<213> ORGANISM: Artificial Sequence
<220> FEATURE:
<223> OTHER INFORMATION: Synthetic

<400> SEQUENCE: 45
ctagtctact atgcggccgc tgaacctgag gccggctggg ccgcattggt tccatcttc    59

<210> SEQ ID NO 46
<211> LENGTH: 57
<212> TYPE: DNA
<213> ORGANISM: Artificial Sequence
<220> FEATURE:
<223> OTHER INFORMATION: Synthetic

<400> SEQUENCE: 46
ccgggaagat ggaaccaata tcgagggaag ggcggcccag ccggcctcag gttcagc      57

<210> SEQ ID NO 47
<211> LENGTH: 57
<212> TYPE: DNA
<213> ORGANISM: Artificial Sequence
<220> FEATURE:
<223> OTHER INFORMATION: Synthetic

<400> SEQUENCE: 47
ggccgctgaa cctgaggccg gctgggccgc ccttccctcg atattggttc catcttc      57

<210> SEQ ID NO 48
<211> LENGTH: 12
<212> TYPE: PRT
<213> ORGANISM: Paramyxoviridae
<220> FEATURE:
<223> OTHER INFORMATION: C-terminal amino acids of H protein

<400> SEQUENCE: 48

Cys Thr Val Thr Arg Glu Asp Gly Thr Asn Arg Arg
1 5 10

<210> SEQ ID NO 49
<211> LENGTH: 7
<212> TYPE: PRT
<213> ORGANISM: Artificial Sequence
<220> FEATURE:
<223> OTHER INFORMATION: Sequence of linker region

<400> SEQUENCE: 49

Ala Ala Gln Pro Ala Met Ala
1 5